US007363171B2

(12) United States Patent
Woods, Jr. et al.

(10) Patent No.: US 7,363,171 B2
(45) Date of Patent: Apr. 22, 2008

(54) ENHANCED METHODS FOR CRYSTALLOGRAPHIC STRUCTURE DETERMINATION EMPLOYING HYDROGEN EXCHANGE ANALYSIS

(75) Inventors: Virgil L. Woods, Jr., San Diego, CA (US); Scott Lesley, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 358 days.

(21) Appl. No.: 10/997,436

(22) Filed: Nov. 24, 2004

(65) Prior Publication Data

US 2006/0166273 A1 Jul. 27, 2006

Related U.S. Application Data

(60) Provisional application No. 60/525,614, filed on Nov. 26, 2003.

(51) Int. Cl.
*G01N 31/00* (2006.01)
(52) U.S. Cl. ..................................... 702/27
(58) Field of Classification Search .............. 702/27
See application file for complete search history.

(56) References Cited

U.S. PATENT DOCUMENTS

| | | | |
|---|---|---|---|
| 4,762,785 A | 8/1988 | Comai | |
| 5,451,513 A | 9/1995 | Maliga et al. | |
| 5,545,817 A | 8/1996 | McBride et al. | |
| 5,658,739 A | 8/1997 | Woods, Jr. | |
| 6,291,189 B1 | 9/2001 | Woods, Jr. | |
| 6,331,400 B1 | 12/2001 | Woods, Jr. | |
| 6,599,707 B1 | 7/2003 | Woods, Jr. | |
| 6,658,739 B1 | 12/2003 | Huang | |

OTHER PUBLICATIONS

McPherson, A. Current Approaches to Macromolecular Crystallization. European Journal of Biochemistry. 1990. vol. 189, pp. 1-23.*
Kundrot, C.E. Which Strategy for a Protein Crystallization Project? Cellular Molecular Life Science. 2004. vol. 61, pp. 525-536.*
Cudney R. Protein Crystallization and Dumb Luck. The Rigaku Journal. 1999. vol. 16, No. 1, pp. 1-7.*
Dale et al. The Protein as a Variable in Protein Crystallization. Journal of Structural Biology. 2003. vol. 142, pp. 88-97.*
Englander et al. Hydrogen-Tritium Exchange. Methods in Enzymology. 1972. vol. 26, pp.*
Englander et al. Hydrogen Exchange Studies of Respiratory Proteins. Journal of Biological Chemistry. 1973. vol. 248, pp. 4852-4861.*
Rosa et al. An Experimental Procedure for Increasing the Structural Resolution of Chemical Hydrogen-exchange Measurements on Proteins: Application to Ribonuclease S Peptie. Journal of Molecular Biology, 1979. vol. 133, pp. 399-416.*

Engen, et al., "Investigating Protein Structure and Dynamics by Hydrogen Exchange MS" *Analytical Chemistry* 73:256A-265A (2001).
Englander, et al., "Protein Structure Change Studied by Hydrogen-Deuterium Exchange, Functional Labeling, and Mass Spectrometry" *Proc. Nat. Acad. Sci.* 100:7057-7062 (2003).
Englander, et al., "Hydrogen Exchange: The Modern Legacy of Linderstrøm-Lang" *Protein Science* 6:1101-1109 (1997).
Hamuro, et al., "Phosphorylation Driven Motions in the COOH-Terminal Src Kinase, Csk, Revealed Through Enhanced Hydrogen-Deuterium Exchange and Mass Spectrometry (DXMS)" *J. Mol. Biol.* 323:871-881 (2002).
Hamuro, et al., "Dynamics of cAPK Type IIβ Activation Revealed by Enhanced Amide H/$^2$H Exchange Mass Spectrometry (DXMS)" *J. Mol. Biol.* 327:1065-1076 (2003).
Hamuro, et al., "Domain Organization of D-AKAP2 Revealed by Enhanced Deuterium Exchange-Mass Spectrometry (DXMS)" *J. Mol. Biol.* 321(4):703-714 (2002).
Hoofnagle, et al., "Changes in Protein Conformational Mobility Upon Activation of Extracellular Regulated Protein Kinase-2 as Detected by Hydrogen Exchange" *PNAS* 98:956-961 (2001).
Kim, et al., "Intramolecular Interactions in Chemically Modified *Escherichia coli* Thioredoxin Monitored by Hydrogen/Deuterium Exchange and Electrospray Ionization Mass Spectrometry" *Biochemistry* 40:14413-14421 (2001).
Kim, et al., "Site-Specific Amide Hydrogen/Deuterium Exchange in *E. coli* Thioredoxins Measured by Electrospray Ionization Mass Spectrometry" *J. Am. Chem. Soc.* 123:9860-9866 (2001).
Kim, et al., "Conformational Changes in Chemically Modified *Escherichia coli* Thioredoxin Monitored by H/D Exchange and Electrospray Ionization Mass Spectrometry" *Protein Science* 11:1320-1329 (2002).
Lesley, et al., "Structural Genomics of the *Thermotoga maritima* Proteome Implemented in a High-Throughput Structure Determination Pipeline" *Proc Natl Acad Sci USA* 99:11664-11669 (2002).

(Continued)

*Primary Examiner*—David J. Steadman
*Assistant Examiner*—Suzanne M. Noakes
(74) *Attorney, Agent, or Firm*—Foley & Lardner LLP; Stephen E. Reiter

(57) ABSTRACT

The present invention provides methods for crystallographic structure determination employing hydrogen exchange analysis. Hydrogen exchange analysis is used to identify unstructured regions of a protein, and then hydrogen exchange analysis repeated after the protein is admixed with candidate agents and/or conditions that may induce structure in said identified unstructured regions. Agents that induce desired structure in the protein are then employed, admixed with the protein, in co-crystallization studies for structure determination. Hydrogen exchange analysis is performed by determining the quantity of isotope and/or rate of exchange of peptide amide hydrogen(s) with isotope on a labeled protein. Proteins with agent-induced decreases in unstructured regions, and thus improved hydrogen exchange structural maps, are optimal for high quality crystallization and structure determination.

40 Claims, 19 Drawing Sheets

OTHER PUBLICATIONS

Mandell, et al., "Measurement of Amide Hydrogen Exchange by MALDI-TOF Mass Spectrometry" *Anal. Chem.* 70:3987-3995 (1998).

Mandell, et al., "Solvent Accessibility of the Thrombin-Thrombomodulin Interface" *J. Mol. Biol.* 306:575-589 (2001).

Mandell, et al., "Identification of Protein-Protein Interfaces by Decreased Amide Proton Solvent Accessibility" *Proc Natl Acad Sci USA* 95:14705-14710 (1998).

McCloskey, J., "Introduction of Deuterium by Exchange for Measurement by Mass Spectrometry" *Meth. in Enzymol.* 193:329-338 (1990).

Peterson, et al., "Mass-Spectrometry Analysis of Agonist-Induced Retinoic Acid Receptor γ Conformational Change" *Biochem. J.* 362:173-181 (2002).

Resing, et al., "Modeling Deuterium Exchange Behavior of ERK2 Using Pepsin Mapping to Probe Secondary Structure" *J. Am Soc Mass Spectrom* 10:685-702 (1999).

Smith, et al., "Probing the Non-Covalent Structure of Proteins by Amide Hydrogen Exchange and Mass Spectrometry" *J. Mass Spectrometry* 32:135-146 (1997).

Spraggon, et al., "Computational Analysis of Crystallization Trials" *Acta. Cryst. D.* 58:1915-1923 (2002).

Wong, et al., "Dynamic Coupling Between the SH2 Domain and Active Site of the COOH Terminal Src Kinase, Csk" *J. Mol. Biol.* 341:93-106 (2004).

Woods, et al., "High Resolution, High-Throughput Amide Deuterium Exchange-Mass Spectrometry (DXMS) Determination of Protein Binding Site Structure and Dynamics: Utility in Pharmaceutical Design" *Journal of Cellular Biochemistry Supplement* 37:89-98 (2001).

Yan, et al., "Hydrogen/Deuterium Exchange and Mass Spectrometric Analysis of a Protein Containing Multiple Disulfide Bonds: Solution Structure of Recombinant Macrophage Colony Stimulating Factor-Beta (rhM-CSFβ)" *Protein Sci* 11:2113-2124 (2002).

Zawadzki et al., "Dissecting Interdomain Communication Within cAPK Regulatory Subunit Type IIβ Using Enhanced Amide Hydrogen/Deuterium Exchange Mass Spectrometry (DXMS)" *Protein Sci.* 12:1980-1990 (2003).

Zhang and Smith, "Determination of Amide Hydrogen Exchange by Mass Spectrometry: A New Toof for Protein Structure Elucidation" *Prot. Sci.* 2:522-531 (1993).

Zhang, et al., "Structural Comparison of Recombinant Human Macrophage Colony Stimulating Factor β and a Partially Reduced Derivative Using Hydrogen Deuterium Exchange and Electrospray Ionization Mass Spectrometry" *Protein Sci* 10:2336-2345 (2001).

\* cited by examiner

The binding of GroES to GroEL is mediated by regions of the GroES subunit that exchange very rapidly in the unbound subunit, suggesting that they are unstructured before they bind to GroEL to form the GroELS complex.

SEQUENCE LISTING

```
<160> NUMBER OF SEQ ID NOS: 22

<210> SEQ ID NO 1
<211> LENGTH: 232
<212> TYPE: PRT
<213> ORGANISM: Thermotoga maritima
<220> FEATURE:
<221> NAME/KEY: PEPTIDE
<222> LOCATION: (1)..(232)

<400> SEQUENCE: 1

Met Gly Ser Asp Lys Ile His His His His His Met Lys Ile Asp
1               5                   10                  15

Ile Leu Asp Lys Gly Phe Val Glu Leu Val Asp Val Met Gly Asn Asp
                20                  25                  30

Leu Ser Ala Val Arg Ala Ala Arg Val Ser Phe Asp Met Gly Leu Lys
                35                  40                  45

Asp Glu Glu Arg Asp Arg His Leu Ile Glu Tyr Leu Met Lys His Gly
            50                  55                  60

His Glu Thr Pro Phe Glu His Ile Val Phe Thr Phe His Val Lys Ala
65                  70                  75                  80

Pro Ile Phe Val Ala Arg Gln Trp Phe Arg His Arg Ile Ala Ser Tyr
                85                  90                  95

Asn Glu Leu Ser Gly Arg Tyr Ser Lys Leu Ser Tyr Glu Phe Tyr Ile
                100                 105                 110

Pro Ser Pro Glu Arg Leu Glu Gly Tyr Lys Thr Thr Ile Pro Pro Glu
            115                 120                 125

Arg Val Thr Glu Lys Ile Ser Glu Ile Val Asp Lys Ala Tyr Arg Thr
        130                 135                 140

Tyr Leu Glu Leu Ile Glu Ser Gly Val Pro Arg Glu Val Ala Arg Ile
145                 150                 155                 160

Val Leu Pro Leu Asn Leu Tyr Thr Arg Phe Phe Trp Thr Val Asn Ala
                165                 170                 175

Arg Ser Leu Met Asn Phe Leu Asn Leu Arg Ala Asp Ser His Ala Gln
                180                 185                 190

Trp Glu Ile Gln Gln Tyr Ala Leu Ala Ile Ala Arg Ile Phe Lys Glu
            195                 200                 205

Lys Cys Pro Trp Thr Phe Glu Ala Phe Leu Lys Tyr Ala Tyr Lys Gly
    210                 215                 220

Asp Ile Leu Lys Glu Val Gln Val
225                 230

<210> SEQ ID NO 2
<211> LENGTH: 303
<212> TYPE: PRT
<213> ORGANISM: Thermotoga maritima
<220> FEATURE:
<221> NAME/KEY: PEPTIDE
<222> LOCATION: (1)..(303)
```

```
<400> SEQUENCE: 2

Met Gly Ser Asp Lys Ile His His His His His Met Met Glu Arg
1               5                   10                  15

Leu Ile Gly Ser Thr Pro Ile Val Arg Leu Asp Ser Ile Asp Ser Arg
            20                  25                  30

Ile Phe Leu Lys Leu Glu Lys Asn Asn Pro Gly Gly Ser Val Lys Asp
        35                  40                  45

Arg Pro Ala Leu Phe Met Ile Leu Asp Ala Glu Lys Arg Gly Leu Leu
    50                  55                  60

Lys Asn Gly Ile Val Glu Pro Thr Ser Gly Asn Met Gly Ile Ala Ile
65                  70                  75                  80

Ala Met Ile Gly Ala Lys Arg Gly His Arg Val Ile Leu Thr Met Pro
                85                  90                  95

Glu Thr Met Ser Val Glu Arg Arg Lys Val Leu Lys Met Leu Gly Ala
            100                 105                 110

Glu Leu Val Leu Thr Pro Gly Glu Leu Gly Met Lys Gly Ala Val Glu
        115                 120                 125

Lys Ala Leu Glu Ile Ser Arg Glu Thr Gly Ala His Met Leu Asn Gln
    130                 135                 140

Phe Glu Asn Pro Tyr Asn Val Tyr Ser His Gln Phe Thr Thr Gly Pro
145                 150                 155                 160

Glu Ile Leu Lys Gln Met Asp Tyr Gln Ile Asp Ala Phe Val Ala Gly
                165                 170                 175

Val Gly Thr Gly Gly Thr Ile Ser Gly Val Gly Arg Val Leu Lys Gly
            180                 185                 190

Phe Phe Gly Asn Gly Val Lys Ile Val Ala Val Glu Pro Ala Lys Ser
        195                 200                 205

Pro Val Leu Ser Gly Gly Gln Pro Gly Lys His Ala Ile Gln Gly Ile
    210                 215                 220

Gly Ala Gly Phe Val Pro Lys Ile Leu Asp Arg Ser Val Ile Asp Glu
225                 230                 235                 240

Val Ile Thr Val Glu Asp Glu Glu Ala Tyr Glu Met Ala Arg Tyr Leu
                245                 250                 255

Ala Lys Lys Glu Gly Leu Leu Val Gly Ile Ser Ser Gly Ala Asn Val
            260                 265                 270

Ala Ala Ala Leu Lys Val Ala Gln Lys Leu Gly Pro Asp Ala Arg Val
        275                 280                 285

Val Thr Val Ala Pro Asp His Ala Glu Arg Tyr Leu Ser Ile Leu
    290                 295                 300

<210> SEQ ID NO 3
<211> LENGTH: 113
<212> TYPE: PRT
<213> ORGANISM: Thermotoga maritima
<220> FEATURE:
<221> NAME/KEY: PEPTIDE
<222> LOCATION: (1)..(113)

<400> SEQUENCE: 3

Met Gly Ser Asp Lys Ile His His His His His Met Ile Leu Val
1               5                   10                  15

Tyr Ser Thr Phe Pro Asn Glu Glu Lys Ala Leu Glu Ile Gly Arg Lys
            20                  25                  30

Leu Leu Glu Lys Arg Leu Ile Ala Cys Phe Asn Ala Phe Glu Ile Arg
        35                  40                  45
```

```
Ser Gly Tyr Trp Trp Lys Gly Glu Ile Val Gln Asp Lys Glu Trp Ala
    50                  55                  60

Ala Ile Phe Lys Thr Thr Glu Glu Lys Glu Lys Glu Leu Tyr Glu Glu
 65              70                  75                  80

Leu Arg Lys Leu His Pro Tyr Glu Thr Pro Ala Ile Phe Thr Leu Lys
                 85                  90                  95

Val Glu Asn Val Leu Thr Glu Tyr Met Asn Trp Leu Arg Glu Ser Val
            100                 105                 110

Leu
```

<210> SEQ ID NO 4
<211> LENGTH: 388
<212> TYPE: PRT
<213> ORGANISM: Thermotoga maritima
<220> FEATURE:
<221> NAME/KEY: PEPTIDE
<222> LOCATION: (1)..(388)

<400> SEQUENCE: 4

```
Met Gly Ser Asp Lys Ile His His His His His Met Asp Ala Leu
 1               5                  10                  15

Glu Ile His Arg Phe Leu Lys Gly Lys Ile Arg Thr Ala Leu Pro Val
                20                  25                  30

Glu Lys Val Asp Arg Glu Thr Leu Ser Leu Leu Tyr Thr Pro Gly Val
            35                  40                  45

Ala Asp Val Ala Arg Ala Cys Ala Glu Asp Pro Glu Lys Thr Tyr Val
 50                  55                  60

Tyr Thr Ser Arg Trp Asn Thr Val Ala Val Ser Asp Gly Ser Ala
 65                  70                  75                  80

Val Leu Gly Leu Gly Asn Ile Gly Pro Tyr Gly Ala Leu Pro Val Met
                 85                  90                  95

Glu Gly Lys Ala Phe Leu Phe Lys Ala Phe Ala Asp Ile Asp Ala Phe
            100                 105                 110

Pro Ile Cys Leu Ser Glu Ser Glu Glu Lys Ile Ile Ser Ile Val
                115                 120                 125

Lys Ser Leu Glu Pro Ser Phe Gly Gly Ile Asn Leu Glu Asp Ile Gly
130                 135                 140

Ala Pro Lys Cys Phe Arg Ile Leu Gln Arg Leu Ser Glu Glu Met Asn
145                 150                 155                 160

Ile Pro Val Phe His Asp Asp Gln Gln Gly Thr Ala Val Val Val Ser
                165                 170                 175

Ala Ala Phe Leu Asn Ala Leu Lys Leu Thr Glu Lys Lys Ile Glu Glu
            180                 185                 190

Val Lys Val Val Val Asn Gly Ile Gly Ala Ala Gly Tyr Asn Ile Val
        195                 200                 205

Lys Phe Leu Leu Asp Leu Gly Val Lys Asn Val Ala Val Asp Arg
210                 215                 220

Lys Gly Ile Leu Asn Glu Asn Asp Pro Glu Thr Cys Leu Asn Glu Tyr
225                 230                 235                 240

His Leu Glu Ile Ala Arg Ile Thr Asn Pro Glu Arg Leu Ser Gly Asp
                245                 250                 255

Leu Glu Thr Ala Leu Glu Gly Ala Asp Phe Phe Ile Gly Val Ser Arg
            260                 265                 270

Gly Asn Ile Leu Lys Pro Glu Trp Ile Lys Lys Met Ser Arg Lys Pro
        275                 280                 285
```

-continued

```
Val Ile Phe Ala Leu Ala Asn Pro Val Pro Glu Ile Asp Pro Glu Leu
    290                 295                 300

Ala Arg Glu Ala Gly Ala Phe Ile Val Ala Thr Gly Arg Ser Asp His
305                 310                 315                 320

Pro Asn Gln Val Asn Asn Leu Leu Ala Phe Pro Gly Ile Met Lys Gly
                325                 330                 335

Ala Val Glu Lys Arg Ser Lys Ile Thr Lys Asn Met Leu Leu Ser Ala
            340                 345                 350

Val Glu Ala Ile Ala Arg Ser Cys Glu Pro Glu Pro Glu Arg Ile Ile
        355                 360                 365

Pro Glu Ala Phe Asp Met Lys Val His Leu Asn Val Tyr Thr Ala Val
    370                 375                 380

Lys Gly Ser Ala
385

<210> SEQ ID NO 5
<211> LENGTH: 463
<212> TYPE: PRT
<213> ORGANISM: Thermotoga maritima
<220> FEATURE:
<221> NAME/KEY: PEPTIDE
<222> LOCATION: (1)..(463)

<400> SEQUENCE: 5

Met Gly Ser Asp Lys Ile His His His His His His Met Phe Leu Gly
1               5                   10                  15

Glu Asp Tyr Leu Leu Thr Asn Arg Ala Ala Val Arg Leu Phe Asn Glu
            20                  25                  30

Val Lys Asp Leu Pro Ile Val Asp Pro His Asn His Leu Asp Ala Lys
        35                  40                  45

Asp Ile Val Glu Asn Lys Pro Trp Asn Asp Ile Trp Glu Val Glu Gly
    50                  55                  60

Ala Thr Asp His Tyr Val Trp Glu Leu Met Arg Arg Cys Gly Val Ser
65                  70                  75                  80

Glu Glu Tyr Ile Thr Gly Ser Arg Ser Asn Lys Glu Lys Trp Leu Ala
                85                  90                  95

Leu Ala Lys Val Phe Pro Arg Phe Val Gly Asn Pro Thr Tyr Glu Trp
            100                 105                 110

Ile His Leu Asp Leu Trp Arg Arg Phe Asn Ile Lys Lys Val Ile Ser
        115                 120                 125

Glu Glu Thr Ala Glu Glu Ile Trp Glu Glu Thr Lys Lys Lys Leu Pro
    130                 135                 140

Glu Met Thr Pro Gln Lys Leu Leu Arg Asp Met Lys Val Glu Ile Leu
145                 150                 155                 160

Cys Thr Thr Asp Asp Pro Val Ser Thr Leu Glu His His Arg Lys Ala
                165                 170                 175

Lys Glu Ala Val Glu Gly Val Thr Ile Leu Pro Thr Trp Arg Pro Asp
            180                 185                 190

Arg Ala Met Asn Val Asp Lys Glu Gly Trp Arg Glu Tyr Val Glu Lys
        195                 200                 205

Met Gly Glu Arg Tyr Gly Glu Asp Thr Ser Thr Leu Asp Gly Phe Leu
    210                 215                 220

Asn Ala Leu Trp Lys Ser His Glu His Phe Lys Glu His Gly Cys Val
225                 230                 235                 240

Ala Ser Asp His Ala Leu Leu Glu Pro Ser Val Tyr Tyr Val Asp Glu
                245                 250                 255
```

```
Asn Arg Ala Arg Ala Val His Glu Lys Ala Phe Ser Gly Glu Lys Leu
            260                 265                 270

Thr Gln Asp Glu Ile Asn Asp Tyr Lys Ala Phe Met Met Val Gln Phe
            275                 280                 285

Gly Lys Met Asn Gln Glu Thr Asn Trp Val Thr Gln Leu His Ile Gly
            290                 295                 300

Ala Leu Arg Asp Tyr Arg Asp Ser Leu Phe Lys Thr Leu Gly Pro Asp
305                 310                 315                 320

Ser Gly Gly Asp Ile Ser Thr Asn Phe Leu Arg Ile Ala Glu Gly Leu
                    325                 330                 335

Arg Tyr Phe Leu Asn Glu Phe Asp Gly Lys Leu Lys Ile Val Leu Tyr
                340                 345                 350

Val Leu Asp Pro Thr His Leu Pro Thr Ile Ser Thr Ile Ala Arg Ala
                355                 360                 365

Phe Pro Asn Val Tyr Val Gly Ala Pro Trp Trp Phe Asn Asp Ser Pro
            370                 375                 380

Phe Gly Met Glu Met His Leu Lys Tyr Leu Ala Ser Val Asp Leu Leu
385                 390                 395                 400

Tyr Asn Leu Ala Gly Met Val Thr Asp Ser Arg Lys Leu Leu Ser Phe
                    405                 410                 415

Gly Ser Arg Thr Glu Met Phe Arg Val Leu Ser Asn Val Val Gly
                420                 425                 430

Glu Met Val Glu Lys Gly Gln Ile Pro Ile Lys Glu Ala Arg Glu Leu
                435                 440                 445

Val Lys His Val Ser Tyr Asp Gly Pro Lys Ala Leu Phe Phe Gly
        450                 455                 460

<210> SEQ ID NO 6
<211> LENGTH: 214
<212> TYPE: PRT
<213> ORGANISM: Thermotoga maritima
<220> FEATURE:
<221> NAME/KEY: PEPTIDE
<222> LOCATION: (1)..(214)

<400> SEQUENCE: 6

Met Gly Ser Asp Lys Ile His His His His His His Met Pro Lys Val
1               5                   10                  15

Glu Ile Ala Pro Ser Glu Ile Lys Ile Pro Asp Asn Val Leu Lys Ala
            20                  25                  30

Lys Leu Gly Phe Gly Gly Ala Glu Glu Ile Pro Glu Glu Phe Arg Lys
        35                  40                  45

Thr Val Asn Arg Ala Tyr Glu Glu Leu Leu Asp Ala Ala Lys Pro Val
    50                  55                  60

Val Leu Trp Arg Asp Phe Glu Val Asp Gly Ser Leu Ser Phe Asp Asp
65                  70                  75                  80

Met Arg Leu Thr Gly Glu Leu Ala Thr Lys His Leu Ser Gly Ser Lys
                85                  90                  95

Ile Ile Thr Val Phe Leu Ala Thr Leu Gly Lys Lys Val Asp Glu Lys
            100                 105                 110

Ile Glu Glu Tyr Phe Arg Lys Gly Glu Asp Leu Leu Ala Phe Phe Ile
        115                 120                 125

Asp Gly Ile Ala Ser Glu Met Val Glu Tyr Ala Leu Arg Lys Val Asp
    130                 135                 140

Ala Glu Leu Arg Met Lys Arg Ser Asn Leu Glu Gly Ser Phe Arg Ile
```

```
                    145                 150                 155                 160
Ser Pro Gly Tyr Gly Asp Leu Pro Leu Ser Leu Asn Lys Lys Ile Ala
                165                 170                 175

Glu Ile Phe Lys Glu Glu Val Asp Val Asn Val Ile Glu Asp Ser Tyr
            180                 185                 190

Val Leu Val Pro Arg Lys Thr Ile Thr Ala Phe Val Gly Trp Arg Glu
        195                 200                 205

Lys Asn Glu Lys Gln Thr
    210

<210> SEQ ID NO 7
<211> LENGTH: 443
<212> TYPE: PRT
<213> ORGANISM: Thermotoga maritima
<220> FEATURE:
<221> NAME/KEY: PEPTIDE
<222> LOCATION: (1)..(443)

<400> SEQUENCE: 7

Met Gly Ser Asp Lys Ile His His His His His Met Gln Met Phe
1               5                   10                  15

Cys Tyr Gln Cys Ser Gln Thr Ala Asn Gly Thr Gly Cys Thr Glu Tyr
                20                  25                  30

Gly Val Cys Gly Lys Ser Pro Thr Val Ala Arg Leu Gln Asp Asn Leu
            35                  40                  45

Val Phe Ala Ile Lys Gly Ile Ser Ala Tyr Tyr His Ala Arg Glu
        50                  55                  60

Leu Gly Tyr Asp Asp Pro Glu Ile Ala Gly Phe Leu Asp Glu Ala Leu
65                  70                  75                  80

Tyr Ser Thr Leu Thr Asn Val Asn Phe Asp Ala Gln Ser Phe Val Glu
                85                  90                  95

Tyr Ala Leu Glu Ala Gly Arg Met Asn Leu Lys Ala Met Gln Leu Leu
            100                 105                 110

Lys Lys Ala His Ile Glu Thr Tyr Gly Glu Pro Thr Pro Val Glu Val
        115                 120                 125

Glu Thr Gly Thr Lys Lys Gly Lys Gly Ile Ile Val Thr Gly His Asn
    130                 135                 140

Leu Lys Ala Leu Glu Leu Leu Lys Gln Val Glu Gly Thr Asn Val
145                 150                 155                 160

Tyr Val Tyr Thr His Ser Glu Met Leu Pro Ala His Gly Tyr Pro Gly
                165                 170                 175

Leu Arg Lys Tyr Lys Asn Leu Ile Gly Asn Leu Gly Lys Ala Trp Tyr
            180                 185                 190

Asp Gln Arg Lys Leu Phe Ala Glu Tyr Pro Val Ala Ile Leu Gly Thr
        195                 200                 205

Ser Asn Cys Val Leu Ile Pro Ser Glu Ser Tyr Arg Asp Arg Met Phe
    210                 215                 220

Thr Thr Ser Ile Ala Arg Leu Pro Gly Val Lys His Ile Asp Gly Tyr
225                 230                 235                 240

Asp Tyr Thr Glu Val Ile Glu Lys Ala Lys Ser Leu Pro Asp Leu Glu
                245                 250                 255

Glu Lys Pro Gly Ser Tyr Lys Leu Arg Thr Gly Phe Ser Thr Ser Val
            260                 265                 270

Val Val Ser Leu Ala Asp Lys Ile Lys Glu Leu Val Glu Ala Gly Lys
        275                 280                 285
```

-continued

Ile Lys His Phe Leu Val Val Gly Gly Cys Asp Val Pro Phe Lys Arg
            290                 295                 300

Asn Glu Tyr Tyr Arg Glu Phe Val Gln Lys Leu Pro Lys Glu Thr Val
305                 310                 315                 320

Val Ile Thr Leu Ala Cys Gly Lys Phe Arg Ile Asn Asp Leu Asp Leu
                325                 330                 335

Gly Asp Ile Asp Gly Ile Pro Arg Leu Ile Asp Val Gly Gln Cys Asn
                340                 345                 350

Asp Thr Ile Val Ala Ile Glu Ile Ala Gln Ala Leu Ala Lys Val Phe
                355                 360                 365

Gly Val Glu Val Thr Glu Leu Pro Leu Thr Leu Val Leu Thr Trp Met
            370                 375                 380

Glu Gln Lys Ala Val Ala Ile Leu Trp Thr Leu Leu Ala Leu Gly Leu
385                 390                 395                 400

Lys Asn Ile Tyr Val Gly Pro Val Leu Pro Ala Trp Val Asn Glu Asp
                405                 410                 415

Ile Leu Lys Val Leu Thr Ala Glu Phe Gly Leu Lys Thr Ile Ser Glu
                420                 425                 430

Pro Glu Lys Asp Ile Lys Glu Ile Leu Lys Val
                435                 440

<210> SEQ ID NO 8
<211> LENGTH: 213
<212> TYPE: PRT
<213> ORGANISM: Thermotoga maritima
<220> FEATURE:
<221> NAME/KEY: PEPTIDE
<222> LOCATION: (1)..(213)

<400> SEQUENCE: 8

Met Gly Ser Asp Lys Ile His His His His His Met Asp Leu Lys
1               5                   10                  15

Lys Leu Leu Pro Cys Gly Lys Val Ile Val Phe Arg Lys Gly Glu Ile
                20                  25                  30

Val Lys His Gln Asp Asp Pro Ile Glu Asp Val Leu Ile Leu Leu Glu
            35                  40                  45

Gly Thr Leu Lys Thr Glu His Val Ser Glu Asn Gly Lys Thr Leu Glu
        50                  55                  60

Ile Asp Glu Ile Lys Pro Val Gln Ile Ile Ala Ser Gly Phe Ile Phe
65                  70                  75                  80

Ser Ser Glu Pro Arg Phe Pro Val Asn Val Val Ala Gly Glu Asn Ser
                85                  90                  95

Lys Ile Leu Ser Ile Pro Lys Glu Val Phe Leu Asp Leu Leu Met Lys
                100                 105                 110

Asp Arg Glu Leu Leu Leu Phe Phe Leu Lys Asp Val Ser Glu His Phe
            115                 120                 125

Arg Val Val Ser Glu Lys Leu Phe Phe Leu Thr Thr Lys Thr Leu Arg
        130                 135                 140

Glu Lys Leu Met Asn Phe Leu Val Arg His Met Asn Glu Lys Arg Glu
145                 150                 155                 160

Leu Thr Leu Pro Val Thr Leu Glu Glu Leu Ser Arg Leu Phe Gly Cys
                165                 170                 175

Ala Arg Pro Ala Leu Ser Arg Val Phe Gln Glu Leu Glu Arg Glu Gly
                180                 185                 190

Tyr Ile Glu Lys His Gly Arg Arg Ile Lys Val Leu Lys Asn Pro Phe
            195                 200                 205

Glu His Asp Arg Ile
    210

<210> SEQ ID NO 9
<211> LENGTH: 193
<212> TYPE: PRT
<213> ORGANISM: Thermotoga maritima
<220> FEATURE:
<221> NAME/KEY: PEPTIDE
<222> LOCATION: (1)..(193)

<400> SEQUENCE: 9

Met Gly Ser Asp Lys Ile His His His His His Met Arg Lys Ala
1               5                   10                  15

Trp Val Lys Thr Leu Ala Leu Asp Arg Val Ser Asn Thr Pro Val Val
                20                  25                  30

Ile Leu Gly Ile Glu Gly Thr Asn Arg Val Leu Pro Ile Trp Ile Gly
            35                  40                  45

Ala Cys Glu Gly His Ala Leu Ala Leu Ala Met Glu Lys Met Glu Phe
    50                  55                  60

Pro Arg Pro Leu Thr His Asp Leu Leu Leu Ser Val Leu Glu Ser Leu
65                  70                  75                  80

Glu Ala Arg Val Asp Lys Val Ile Ile His Ser Leu Lys Asp Asn Thr
                85                  90                  95

Phe Tyr Ala Thr Leu Val Ile Arg Asp Leu Thr Tyr Thr Asp Glu Glu
            100                 105                 110

Asp Glu Glu Ala Ala Leu Ile Asp Ile Asp Ser Arg Pro Ser Asp Ala
        115                 120                 125

Ile Ile Leu Ala Val Lys Thr Gly Ala Pro Ile Phe Val Ser Asp Asn
130                 135                 140

Leu Val Glu Lys His Ser Ile Glu Leu Glu Val Asn Glu Thr Gln Asp
145                 150                 155                 160

Glu Glu Glu Glu Phe Lys Lys Phe Val Glu Asn Leu Asn Ile Asp Thr
                165                 170                 175

Phe Lys Gln Met Ile Glu Lys Lys Arg Glu Glu Asp Glu Glu Gly Glu
            180                 185                 190

Ser

<210> SEQ ID NO 10
<211> LENGTH: 104
<212> TYPE: PRT
<213> ORGANISM: Thermotoga maritima
<220> FEATURE:
<221> NAME/KEY: PEPTIDE
<222> LOCATION: (1)..(104)

<400> SEQUENCE: 10

Met Gly Ser Asp Lys Ile His His His His His Met Met Lys Val
1               5                   10                  15

Ile Pro Leu Gly Glu Arg Leu Leu Ile Lys Pro Ile Lys Glu Glu Lys
                20                  25                  30

Lys Thr Glu Gly Gly Ile Val Leu Pro Asp Ser Ala Lys Glu Lys Pro
            35                  40                  45

Met Lys Ala Glu Val Val Ala Val Gly Lys Ile Asp Asp Glu Lys
    50                  55                  60

Phe Asp Ile Lys Val Gly Asp Lys Val Ile Tyr Ser Lys Tyr Ala Gly
65                  70                  75                  80

```
Thr Glu Ile Lys Ile Asp Asp Glu Asp Tyr Ile Ile Asp Val Asn
                85                  90                  95
Asp Ile Leu Ala Lys Ile Glu Glu
            100

<210> SEQ ID NO 11
<211> LENGTH: 104
<212> TYPE: PRT
<213> ORGANISM: Thermotoga maritima
<220> FEATURE:
<221> NAME/KEY: PEPTIDE
<222> LOCATION: (1)..(104)

<400> SEQUENCE: 11

Met Gly Ser Asp Lys Ile His His His His His Met Met Lys Val
1               5                   10                  15

Ile Pro Leu Gly Glu Arg Leu Leu Ile Lys Pro Ile Lys Glu Lys
                20                  25                  30

Lys Thr Glu Gly Gly Ile Val Leu Pro Asp Ser Ala Lys Glu Pro
                35                  40                  45

Met Lys Ala Glu Val Val Ala Val Gly Lys Ile Asp Asp Glu Lys
            50                  55                  60

Phe Asp Ile Lys Val Gly Asp Lys Val Ile Tyr Ser Lys Tyr Ala Gly
65                  70                  75                  80

Thr Glu Ile Lys Ile Asp Asp Glu Asp Tyr Ile Ile Asp Val Asn
                85                  90                  95

Asp Ile Leu Ala Lys Ile Glu Glu
            100

<210> SEQ ID NO 12
<211> LENGTH: 168
<212> TYPE: PRT
<213> ORGANISM: Thermotoga maritima
<220> FEATURE:
<221> NAME/KEY: PEPTIDE
<222> LOCATION: (1)..(168)

<400> SEQUENCE: 12

Met Gly Ser Asp Lys Ile His His His His His Met Lys Lys Val
1               5                   10                  15

Arg Leu Thr Arg Glu Gly Tyr Glu Lys Leu Lys Lys Glu Leu Glu Asp
                20                  25                  30

Leu Lys Arg Lys Phe Met Tyr Glu Ile Ser Glu Arg Ile Lys Glu Ala
            35                  40                  45

Arg Glu Leu Gly Asp Leu Ser Glu Asn Ser Glu Tyr Glu Ala Ala Lys
        50                  55                  60

Asn Glu Gln Gly Arg Val Gly Ser Arg Ile Met Glu Ile Glu Gln Ile
65                  70                  75                  80

Leu Ser Asn Ala Glu Ile Ile Gly Asp Ser Glu Ser Asp Glu Val
                85                  90                  95

Thr Leu Gly Lys Trp Val Val Ile Lys Asn Leu Asp Thr Gly Glu Glu
            100                 105                 110

His Lys Phe Arg Ile Val Thr Pro Gln Glu Ala Asp Phe Phe Ala Gln
            115                 120                 125

Lys Leu Ser Ser Asp Ser Pro Leu Gly Lys Ser Leu Leu Gly Arg Lys
        130                 135                 140

Val Gly Asp Val Val Lys Val Lys Ala Pro Ser Gly Val Gln Arg Tyr
145                 150                 155                 160
```

Gln Val Ile Ala Val Met Asn Lys
              165

<210> SEQ ID NO 13
<211> LENGTH: 270
<212> TYPE: PRT
<213> ORGANISM: Thermotoga maritima
<220> FEATURE:
<221> NAME/KEY: PEPTIDE
<222> LOCATION: (1)..(270)

<400> SEQUENCE: 13

Met Gly Ser Asp Lys Ile His His His His His Met Lys Ile Ala
1               5                   10                  15

Ile Leu Tyr Arg Glu Glu Arg Glu Lys Glu Gly Glu Phe Leu Lys Glu
                20                  25                  30

Lys Ile Ser Lys Glu His Glu Val Ile Glu Phe Gly Glu Ala Asn Ala
                35                  40                  45

Pro Gly Arg Val Thr Ala Asp Leu Ile Val Val Gly Gly Asp Gly
        50                  55                  60

Thr Val Leu Lys Ala Ala Lys Lys Ala Ala Asp Gly Thr Pro Met Val
65                  70                  75                  80

Gly Phe Lys Ala Gly Arg Leu Gly Phe Leu Thr Ser Tyr Thr Leu Asp
                    85                  90                  95

Glu Ile Asp Arg Phe Leu Glu Asp Leu Arg Asn Trp Asn Phe Arg Glu
                100                 105                 110

Glu Thr Arg Trp Phe Ile Gln Ile Glu Ser Glu Leu Gly Asn His Leu
            115                 120                 125

Ala Leu Asn Asp Val Thr Leu Glu Arg Asp Leu Ser Gly Lys Met Val
130                 135                 140

Glu Ile Glu Val Glu Val Glu His His Ser Ser Met Trp Phe Phe Ala
145                 150                 155                 160

Asp Gly Val Val Ile Ser Thr Pro Thr Gly Ser Thr Ala Tyr Ser Leu
                    165                 170                 175

Ser Ile Gly Gly Pro Ile Ile Phe Pro Glu Cys Glu Val Leu Glu Ile
                180                 185                 190

Ser Pro Ile Ala Pro Gln Phe Phe Leu Thr Arg Ser Val Val Ile Pro
            195                 200                 205

Ser Asn Phe Lys Val Val Val Glu Ser Gln Arg Asp Ile Asn Met Leu
210                 215                 220

Val Asp Gly Val Leu Thr Gly Lys Thr Lys Arg Ile Glu Val Lys Lys
225                 230                 235                 240

Ser Arg Arg Tyr Val Arg Ile Leu Arg Pro Pro Glu Tyr Asp Tyr Val
                245                 250                 255

Thr Val Ile Arg Asp Lys Leu Gly Tyr Gly Arg Arg Ile Glu
                260                 265                 270

<210> SEQ ID NO 14
<211> LENGTH: 276
<212> TYPE: PRT
<213> ORGANISM: Thermotoga maritima
<220> FEATURE:
<221> NAME/KEY: PEPTIDE
<222> LOCATION: (1)..(276)

<400> SEQUENCE: 14

Met Gly Ser Asp Lys Ile His His His His His Met Arg Phe Lys
1               5                   10                  15

```
Glu Leu Ile Leu Pro Leu Lys Ile Glu Glu Glu Leu Val Glu Lys
         20                  25                  30

Phe Tyr Glu Glu Gly Phe Phe Asn Phe Ala Ile Glu Glu Asp Lys Lys
             35                  40                  45

Gly Lys Lys Val Leu Lys Ile Tyr Leu Arg Glu Gly Pro Leu Pro
 50                  55                  60

Asp Phe Leu Lys Asp Trp Glu Ile Val Asp Glu Lys Ile Thr Thr Pro
 65                  70                  75                  80

Lys Asp Trp Ile Val Glu Leu Glu Pro Phe Glu Ile Val Glu Gly Ile
                 85                  90                  95

Phe Ile Asp Pro Thr Glu Lys Ile Asn Arg Arg Asp Ala Ile Val Ile
             100                 105                 110

Lys Leu Ser Pro Gly Val Ala Phe Gly Thr Gly Leu His Pro Thr Thr
         115                 120                 125

Arg Met Ser Val Phe Phe Leu Lys Lys Tyr Leu Lys Glu Gly Asn Thr
130                 135                 140

Val Leu Asp Val Gly Cys Gly Thr Gly Ile Leu Ala Ile Ala Ala Lys
145                 150                 155                 160

Lys Leu Gly Ala Ser Arg Val Val Ala Val Asp Val Asp Glu Gln Ala
                 165                 170                 175

Val Glu Val Ala Glu Glu Asn Val Arg Lys Asn Asp Val Asp Val Leu
             180                 185                 190

Val Lys Trp Ser Asp Leu Leu Ser Glu Val Glu Gly Thr Phe Asp Ile
         195                 200                 205

Val Val Ser Asn Ile Leu Ala Glu Ile His Val Lys Leu Leu Glu Asp
     210                 215                 220

Val Asn Arg Val Thr His Arg Asp Ser Met Leu Ile Leu Ser Gly Ile
225                 230                 235                 240

Val Asp Arg Lys Glu Asp Met Val Lys Arg Lys Ala Ser Glu His Gly
                 245                 250                 255

Trp Asn Val Leu Glu Arg Lys Gln Glu Arg Glu Trp Val Thr Leu Val
             260                 265                 270

Met Lys Arg Ser
        275

<210> SEQ ID NO 15
<211> LENGTH: 267
<212> TYPE: PRT
<213> ORGANISM: Thermotoga maritima
<220> FEATURE:
<221> NAME/KEY: PEPTIDE
<222> LOCATION: (1)..(267)

<400> SEQUENCE: 15

Met Gly Ser Asp Lys Ile His His His His His Met Lys Glu Ala
 1               5                  10                  15

Gly Ile Leu Phe Glu Glu Leu Val Ser Ile Met Glu Lys Leu Arg Ser
             20                  25                  30

Pro Glu Gly Cys Glu Trp Asp Arg Lys Gln Thr His Glu Ser Leu Lys
         35                  40                  45

Pro Tyr Leu Ile Glu Glu Cys Tyr Glu Leu Ile Glu Ala Ile Asp Glu
     50                  55                  60

Lys Asn Asp Asp Met Met Lys Glu Glu Leu Gly Asp Val Leu Leu Gln
65                  70                  75                  80

Val Val Phe His Ala Gln Ile Ala Arg Glu Arg Gly Ala Phe Thr Ile
                 85                  90                  95
```

-continued

```
Glu Asp Val Ile Arg Thr Leu Asn Glu Lys Leu Ile Arg Arg His Pro
            100                 105                 110
His Val Phe Gly Asp Ser Pro Gly Tyr Ser Tyr Lys Gln Trp Glu Asp
            115                 120                 125
Ile Lys Ala Gln Glu Lys Gly Lys Lys Ser Ser Arg Ile Gly Glu
            130                 135                 140
Ile Asn Pro Leu Val Pro Ala Leu Ser Met Ala Arg Arg Ile Gln Glu
145                 150                 155                 160
Asn Ala Ser Gln Val Gly Phe Asp Trp Lys Asp Pro Glu Gly Val Tyr
                165                 170                 175
Glu Lys Ile Glu Glu Glu Leu Lys Glu Leu Lys Glu Ala Lys Asp Pro
            180                 185                 190
Arg Glu Leu Glu Glu Glu Phe Gly Asp Leu Leu Phe Ser Ile Val Asn
            195                 200                 205
Leu Ser Arg Phe Leu Asn Val Asp Pro Glu Ser Ala Leu Arg Lys Ala
            210                 215                 220
Thr Arg Lys Phe Val Glu Arg Phe Lys Lys Met Glu Glu Leu Ile Glu
225                 230                 235                 240
Lys Asp Gly Leu Val Leu Glu Glu Leu Pro Ile Glu Lys Leu Asp Glu
                245                 250                 255
Tyr Trp Glu Lys Ala Lys Gly Gly Asp Glu Thr
            260                 265

<210> SEQ ID NO 16
<211> LENGTH: 239
<212> TYPE: PRT
<213> ORGANISM: Thermotoga maritima
<220> FEATURE:
<221> NAME/KEY: PEPTIDE
<222> LOCATION: (1)..(239)

<400> SEQUENCE: 16

Met Gly Ser Asp Lys Ile His His His His His Met Arg Val Leu
1               5                   10                  15
Ala Ile Arg His Val Glu Ile Glu Asp Leu Gly Met Met Glu Asp Ile
            20                  25                  30
Phe Arg Glu Lys Asn Trp Ser Phe Asp Tyr Leu Asp Thr Pro Lys Gly
        35                  40                  45
Glu Lys Leu Glu Arg Pro Leu Glu Glu Tyr Ser Leu Val Val Leu Leu
    50                  55                  60
Gly Gly Tyr Met Gly Ala Tyr Glu Glu Glu Lys Tyr Pro Phe Leu Lys
65                  70                  75                  80
Tyr Glu Phe Gln Leu Ile Glu Glu Ile Leu Lys Lys Glu Ile Pro Phe
                85                  90                  95
Leu Gly Ile Cys Leu Gly Ser Gln Met Leu Ala Lys Val Leu Gly Ala
            100                 105                 110
Ser Val Tyr Arg Gly Lys Asn Gly Glu Glu Ile Gly Trp Tyr Phe Val
            115                 120                 125
Glu Lys Val Ser Asp Asn Lys Phe Phe Arg Glu Phe Pro Asp Arg Leu
        130                 135                 140
Arg Val Phe Gln Trp His Gly Asp Thr Phe Asp Leu Pro Arg Arg Ala
145                 150                 155                 160
Thr Arg Val Phe Thr Ser Glu Lys Tyr Glu Asn Gln Gly Phe Val Tyr
                165                 170                 175
Gly Lys Ala Val Gly Leu Gln Phe His Ile Glu Val Gly Ala Arg Thr
```

```
                    180                 185                 190
Met Lys Arg Trp Ile Glu Ala Tyr Lys Asp Glu Leu Glu Lys Lys
            195                 200                 205

Ile Asp Pro Arg Leu Leu Glu Thr Ala Glu Arg Glu Glu Lys Val
        210                 215                 220

Leu Lys Gly Leu Leu Arg Ser Leu Leu Glu Arg Met Val Glu Ser
225                 230                 235

<210> SEQ ID NO 17
<211> LENGTH: 136
<212> TYPE: PRT
<213> ORGANISM: Thermotoga maritima
<220> FEATURE:
<221> NAME/KEY: PEPTIDE
<222> LOCATION: (1)..(136)

<400> SEQUENCE: 17

Met Gly Ser Asp Lys Ile His His His His His Met Lys Met Lys
1               5                   10                  15

Lys Tyr Thr Lys Thr His Glu Trp Val Ser Ile Glu Asp Lys Val Ala
            20                  25                  30

Thr Val Gly Ile Thr Asn His Ala Gln Glu Gln Leu Gly Asp Val Val
        35                  40                  45

Tyr Val Asp Leu Pro Glu Val Gly Arg Glu Val Lys Lys Gly Glu Val
    50                  55                  60

Val Ala Ser Ile Glu Ser Val Lys Ala Ala Asp Val Tyr Ala Pro
65                  70                  75                  80

Leu Ser Gly Lys Ile Val Glu Val Asn Glu Lys Leu Asp Thr Glu Pro
                85                  90                  95

Glu Leu Ile Asn Lys Asp Pro Glu Gly Gly Trp Leu Phe Lys Met
            100                 105                 110

Glu Ile Ser Asp Glu Gly Glu Leu Glu Asp Leu Leu Asp Glu Gln Ala
        115                 120                 125

Tyr Gln Glu Phe Cys Ala Gln Glu
    130                 135

<210> SEQ ID NO 18
<211> LENGTH: 79
<212> TYPE: PRT
<213> ORGANISM: Thermotoga maritima
<220> FEATURE:
<221> NAME/KEY: PEPTIDE
<222> LOCATION: (1)..(79)

<400> SEQUENCE: 18

Met Gly Ser Asp Lys Ile His His His His His Met Arg Tyr Val
1               5                   10                  15

Leu Tyr Val Pro Asp Ile Ser Cys Asn His Cys Lys Met Arg Ile Ser
            20                  25                  30

Lys Ala Leu Glu Glu Leu Gly Val Lys Asn Tyr Glu Val Ser Val Glu
        35                  40                  45

Glu Lys Lys Val Val Val Glu Thr Glu Asn Leu Asp Ser Val Leu Lys
    50                  55                  60

Lys Leu Glu Glu Ile Asp Tyr Pro Val Glu Ser Tyr Gln Glu Val
65                  70                  75

<210> SEQ ID NO 19
<211> LENGTH: 155
<212> TYPE: PRT
```

```
<213> ORGANISM: Thermotoga maritima
<220> FEATURE:
<221> NAME/KEY: PEPTIDE
<222> LOCATION: (1)..(155)

<400> SEQUENCE: 19

Met Gly Ser Asp Lys Ile His His His His His Met Lys Ile Ala
1               5                   10                  15

Ile Ala Ser Asp His Ala Ala Phe Glu Leu Lys Glu Lys Val Lys Asn
            20                  25                  30

Tyr Leu Leu Gly Lys Gly Ile Glu Val Glu Asp His Gly Thr Tyr Ser
            35                  40                  45

Glu Glu Ser Val Asp Tyr Pro Asp Tyr Ala Lys Lys Val Val Gln Ser
        50                  55                  60

Ile Leu Ser Asn Glu Ala Asp Phe Gly Ile Leu Leu Cys Gly Thr Gly
65                  70                  75                  80

Leu Gly Met Ser Ile Ala Ala Asn Arg Tyr Arg Gly Ile Arg Ala Ala
                85                  90                  95

Leu Cys Leu Phe Pro Asp Met Ala Arg Leu Ala Arg Ser His Asn Asn
            100                 105                 110

Ala Asn Ile Leu Val Leu Pro Gly Arg Leu Ile Gly Ala Glu Leu Ala
            115                 120                 125

Phe Trp Ile Val Asp Thr Phe Leu Ser Thr Pro Phe Asp Gly Gly Arg
        130                 135                 140

His Glu Arg Arg Ile Arg Lys Ile Asp Glu Val
145                 150                 155

<210> SEQ ID NO 20
<211> LENGTH: 297
<212> TYPE: PRT
<213> ORGANISM: Thermotoga maritima
<220> FEATURE:
<221> NAME/KEY: PEPTIDE
<222> LOCATION: (1)..(297)

<400> SEQUENCE: 20

Met Gly Ser Asp Lys Ile His His His His His Met Ile Ile Glu
1               5                   10                  15

Ser Arg Ile Glu Lys Gly Lys Pro Val Val Gly Met Glu Thr Thr Val
            20                  25                  30

Phe Val His Gly Leu Pro Arg Lys Glu Ala Ile Glu Leu Phe Arg Arg
            35                  40                  45

Ala Lys Glu Ile Ser Arg Glu Lys Gly Phe Gln Leu Ala Val Ile Gly
        50                  55                  60

Ile Leu Lys Gly Lys Ile Val Ala Gly Met Ser Glu Glu Glu Leu Glu
65                  70                  75                  80

Ala Met Met Arg Glu Gly Ala Asp Lys Val Gly Thr Arg Glu Ile Pro
                85                  90                  95

Ile Val Val Ala Glu Gly Lys Asn Ala Ala Thr Thr Val Ser Ala Thr
            100                 105                 110

Ile Phe Leu Ser Arg Arg Ile Gly Ile Glu Val Val Val Thr Gly Gly
            115                 120                 125

Thr Gly Gly Val His Pro Gly Arg Val Asp Val Ser Gln Asp Leu Thr
        130                 135                 140

Glu Met Ser Ser Arg Ala Val Leu Val Ser Ser Gly Ile Lys Ser
145                 150                 155                 160

Ile Leu Asp Val Glu Ala Thr Phe Glu Met Leu Glu Thr Leu Glu Ile
```

-continued

```
                165                 170                 175
Pro Leu Val Gly Phe Arg Thr Asn Glu Phe Pro Leu Phe Phe Ser Arg
            180                 185                 190

Lys Ser Gly Arg Arg Val Pro Arg Ile Glu Asn Val Glu Glu Val Leu
        195                 200                 205

Lys Ile Tyr Glu Ser Met Lys Glu Met Glu Leu Glu Lys Thr Leu Met
    210                 215                 220

Val Leu Asn Pro Val Pro Glu Glu Tyr Glu Ile Pro His Asp Glu Ile
225                 230                 235                 240

Glu Arg Leu Leu Glu Lys Ile Glu Leu Glu Val Glu Gly Lys Glu Val
                245                 250                 255

Thr Pro Phe Leu Leu Lys Lys Leu Val Glu Met Thr Asn Gly Arg Thr
            260                 265                 270

Leu Lys Ala Asn Leu Ala Leu Leu Glu Glu Asn Val Lys Leu Ala Gly
        275                 280                 285

Glu Ile Ala Val Lys Leu Lys Arg Ser
    290                 295

<210> SEQ ID NO 21
<211> LENGTH: 106
<212> TYPE: PRT
<213> ORGANISM: Thermotoga maritima
<220> FEATURE:
<221> NAME/KEY: PEPTIDE
<222> LOCATION: (1)..(106)

<400> SEQUENCE: 21

Met Gly Ser Asp Lys Ile His His His His His Met Pro Lys Val
1               5                   10                  15

Thr Val Ser Ile Lys Val Val Pro Ala Val Glu Asp Gly Arg Leu His
                20                  25                  30

Glu Val Ile Asp Arg Ala Ile Glu Lys Ile Ser Ser Trp Gly Met Lys
            35                  40                  45

Tyr Glu Val Gly Pro Ser Asn Thr Thr Val Glu Gly Glu Phe Glu Glu
        50                  55                  60

Ile Met Asp Arg Val Lys Glu Leu Ala Arg Tyr Leu Glu Gln Phe Ala
65                  70                  75                  80

Lys Arg Phe Val Leu Gln Leu Asp Ile Asp Tyr Lys Ala Gly Gly Ile
                85                  90                  95

Thr Ile Glu Glu Lys Val Ser Lys Tyr Arg
            100                 105

<210> SEQ ID NO 22
<211> LENGTH: 213
<212> TYPE: PRT
<213> ORGANISM: Gallus sp.
<220> FEATURE:
<221> NAME/KEY: REPEAT
<222> LOCATION: (1)..(213)

<400> SEQUENCE: 22

Met Val His Gln Phe Phe Arg Asp Met Asp Asp Glu Glu Ser Trp Ile
1               5                   10                  15

Lys Glu Lys Lys Leu Leu Val Ser Ser Glu Asp Tyr Gly Arg Asp Leu
                20                  25                  30

Thr Gly Val Gln Asn Leu Arg Lys Lys His Lys Arg Leu Glu Ala Glu
            35                  40                  45

Leu Ala Ala His Glu Pro Ala Ile Gln Ser Val Leu Asp Thr Gly Lys
```

-continued

```
              50                    55                    60
Lys Leu Ser Asp Asp Asn Thr Ile Gly Lys Glu Glu Ile Gln Gln Arg
65                      70                  75                  80

Leu Ala Gln Phe Val Asp His Trp Lys Glu Leu Lys Gln Leu Ala Ala
                85                  90                  95

Ala Arg Gly Gln Arg Leu Glu Glu Ala Leu Glu Tyr Gln Gln Phe Val
            100                 105                 110

Ala Asn Val Glu Glu Glu Ala Trp Ile Asn Glu Lys Met Thr Leu
        115                 120                 125

Val Ala Ser Glu Asp Tyr Gly Asp Thr Leu Ala Ala Ile Gln Gly Leu
        130                 135                 140

Leu Lys Lys His Glu Ala Phe Glu Thr Asp Phe Thr Val His Lys Asp
145                 150                 155                 160

Arg Val Asn Asp Val Cys Ala Asn Gly Glu Asp Leu Ile Lys Lys Asn
                165                 170                 175

Asn His His Val Glu Asn Ile Thr Ala Lys Met Lys Gly Leu Lys Gly
            180                 185                 190

Lys Val Ser Asp Leu Glu Lys Ala Ala Ala Gln Arg Lys Ala Lys Leu
        195                 200                 205

Asp Glu Asn Ser Ala
        210
```

ENHANCED METHODS FOR CRYSTALLOGRAPHIC STRUCTURE DETERMINATION EMPLOYING HYDROGEN EXCHANGE ANALYSIS

RELATED APPLICATION

This application claims priority from U.S. application Ser. No. 60/525,614 filed Nov. 26, 2003, the entire contents of which is hereby incorporated by reference herein.

FIELD OF THE INVENTION

The present invention relates to methods for determining polypeptide structure using crystallography. In a particular aspect, the invention relates to methods for crystallographic structure determination that employ hydrogen exchange analysis to identify agents and conditions that can be used to induce 3-dimensional structure in otherwise unstructured regions of proteins and enhance crystallography.

BACKGROUND OF THE INVENTION

Determination of high-resolution structures is required for fundamental understanding of how particular protein modifications promote or cause disease processes, e.g., cancer. A critical shortcoming of present high-throughput (HT) crystallographic structure determination efforts is that they fail to produce crystals for more than 80% of the target proteins. Floppy, unstructured regions of proteins can play a dominant role in this problem; the energetics and kinetics of crystallization are often less favorable than for fully structured proteins, and these regions are often more susceptible to degradation during purification than are structured regions, thus promoting sample heterogeneity. There is considerable advantage in producing proteins in forms that contain the structured regions in their native conformation, but with the unstructured regions otherwise stabilized. Unfortunately, no robust technique exists to discern structured vs. unstructured regions of target proteins at the pace required for HT efforts, nor is there a general and robust method to effect the stabilization of unstructured regions within proteins that are to be subjected to crystallographic structure determination efforts.

Measurement of the exchange rates of peptide amide hydrogens within a protein can report its stability at the individual amino acid scale. Ranking and comparison of the exchange rates of a protein's amide hydrogens therefore allows direct identification and localization of structured vs. unstructured regions of the protein. Despite the utility of such exchange data, the methods used to obtain it have remained labor intensive and time consuming, with substantial limitations in throughput, comprehensiveness and resolution. A number of enhancements to amide hydrogen/deuterium exchange-mass spectrometry (DXMS technology) that have substantially overcome these limitations have recently been developed and integrated. The instant invention employs this technology to guide design of superior protein constructs for crystallographic analysis at a HT pace.

As described herein, DXMS is used to precisely define the disordered regions in 21 *Thermotoga maritima* proteins in a total of two weeks time. The data demonstrates that this approach to defining unstructured regions of proteins works well, and at a high throughput pace and resolution, furthermore it demonstrates that hydrogen exchange analysis can identify a protein binding partner that can induce structure in previously unstructured regions of a target protein, and that co-crystallization of protein and binding partner can be accomplished.

High-resolution structures are required for a fundamental understanding of how modifications of cancer-implicated proteins can promote oncogenesis and metastasis and can provide a dramatically effective guide to the rational design of therapeutics to clinically important targets. The pressing need for this information in a timely manner contrasts with the agonizingly slow pace of present high-resolution structure determination methods. Access to these important structures will be facilitated by novel high-throughput (HT) protein structure determination approaches and improvements to conventional crystallographic methods. Despite the availability of many enhancements that facilitate such efforts, high throughput production of stable protein constructs that suitably crystallize continues to be a serious bottleneck. While definition of successful constructs has long been a problem for conventional crystallography, the inadequacies of current approaches are particularly acute and costly for structural genomics efforts that presently show only a 5-20% success rate in target crystallization. Bacterial genomes are currently the focus of many of the structural genomics efforts. However the switch to higher eukaryotes, such as mouse and human, will entail even lower success rates, due in part to more complex and higher molecular weight proteins. A critical need, therefore, exists for robust techniques that can efficiently define protein domain boundaries, the location of floppy regions between domains, as well as disordered regions within single-domain proteins.

Need for HT Methods to Reliably Define Structured/Unstructured Regions of Crystallographic Targets Many, if not the majority, of proteins, contain unstructured regions (see, e.g., Wright and Dyson, *J. Mol. Biol.* 293:321-331, 1999). It is thought that such regions are induced to form specific, functionally important structures when the proteins bind to and otherwise interact with physiologic binding partners, including other proteins, carbohydrates, lipids, co-actors, etc. that are present in the protein's normal cellular milieu.

Unfortunately, while such unstructured regions may serve a function within the protein when it is interacting with binding partners in the normal cellular environment, such unstructured regions can inhibit or prevent crystallization of the entire protein when it is purified away from and therefore not bound to its structure-forming binding partners. Present structure determination efforts and methods are almost always preceded by the isolation and purification of proteins to be studied, in most cases removing from the environs of the protein these elements that can induce structure in the normal milieu. This is usually a necessity for protein crystallization, as crystallization is usually markedly inhibited within mixtures of proteins, and there is usually no a priori knowledge of the nature or identity of agents that if added to the purified protein would improve its crystallization success, nor are there facile assays for same. The approach therefore is almost always to highly purify the protein prior to crystallization trials.

This unstructured protein subregion problem has been apparent for years, but its full extent is difficult to discern from the published literature. In some instances, proteins may crystallize with some floppy regions, either at their ends or within short internal stretches. In many other instances, it is not known why a particular protein does not crystallize, even with seemingly pure protein. Using the methods of the present invention, crystallographic structure determination is facilitated by the ability to rapidly and precisely define structured and unstructured regions of a target protein, and then rapidly identify a minimal set of protein binding partner(s), small molecule co-factors, or modified chemical conditions (pH, salts, salt concentration) herein collectively termed structure-inducing agents or conditions, or abbreviated "agents", that can be selectively admixed with the protein for subsequent co-crystallization studies to produce agent-perturbed protein-co-crystals with superior properties for diffraction analysis.

This capability to define structured and unstructured region of a protein of interest can enhance crystallographic structure determination through several mechanisms. It can increase the homogeneity of protein preparations. Moreover, unstructured regions of proteins are particularly susceptible to inadvertent degradation by contaminating cellular proteases in the course of purification and storage. The energetics and kinetics of protein crystallization are facilitated by removal or structuring of unstructured sequences (see, e.g., Kwong et al., *J. Biol. Chem.* 274:4115-4123, 1999).

Shortcomings of Present Methods to Localize Structured/Unstructured Regions

A number of approaches to obtain this information, ranging from stability-dependent protein expression screens, to computation of stability from primary structure (Dunker, et al. Pac. Symp. Biocomput. 3:473-484 1998, Garner, et al. Genome Inform. 9:201-214 1998, Romero, et al. Pac. Symp. Biocomput. 3:437-448 1998) have been reported and used, but each has requirements that limit utility. With NMR spectroscopy, protein quantity, concentration, time needed, and size are limiting. Limited proteolysis coupled to mass spectrometry is presently one of the preferred approaches to refining construct definition for conventional crystallographic efforts. (Cohen, et al. Protein Science 4:1088-1099 1995). As such its use is time consuming, frequently requiring that multiple proteolytic reactions be refined for optimal cleavage. Interpretation of limited proteolysis results is confounded by the possibility that proteolysis may clip internal loops, leading to destabilization and subsequent further proteolytic degradation of what was actually a structured region. Often it is known in advance that a particular protein is likely made up of several domains that are connected by flexible linkers. Examples of this are DNA binding proteins such as the lambda repressor C-terminal (Bell, et al. J. Mol. Biol. 314:1127-1136 2001) and the TRHF dimerization domain of the human telomeric protein (Fairall, et al. Mol. Cell. 8:351-361 2001). Unfortunately, the experimental definition of domain boundaries, even when they are anticipated, is often problematic, as it was for these proteins, and is usually addressed through trial and error, by making many constructs and testing the outcome as far as expression, solubility and crystallization. As provided herein, studies indicate that measurement of peptide amide hydrogen exchange rates can provide precisely the information needed to define and localize disordered regions of proteins, and to systematically identify agents that induce structure in such subregions, and that the advanced hydrogen exchange data acquisition methods herein have the throughput and robustness needed for HT crystallography.

Peptide Amide Hydrogen Exchange Measurements Precisely and Directly Report Protein Structural Stability For more than 40 years, peptide amide hydrogen-exchange techniques have been employed to study the thermodynamics of protein conformational change and the mechanisms of protein folding (Englander, et al. Methods Enzymol. 232:26-42 1994, Bai, et al. Methods Enzymol. 259:344 1995). More recently, they have proven to be increasingly powerful methods by which protein dynamics, domain structure, regional stability and function can be studied (Englander, et al. Protein Science 6:1101-9 1997, Engen, et al. Analytical Chemistry 73:256A-265A 2001). Peptide amide hydrogens are not permanently attached to a protein, but continuously and reversibly interchange with hydrogen present in water. The chemical mechanisms of the exchange reactions are understood, and several well-defined factors can profoundly alter exchange rates. (Englander, et al. Methods Enzymol. 232:26-42 1994, Englander, et al. Anal. Biochem. 147:234-244 1985, Englander, et al. Methods Enzymol. 26:406-413 1972, Englander, et al. Methods Enzymol. 49G:24-39 1978) One of these factors is the extent to which a particular exchangeable hydrogen is exposed (accessible) to water.

In a completely unstructured polypeptide chain, all peptide amide hydrogens are freely accessible to water and exchange at their maximal possible rate, with a half-life of exchange of approximately one second at 0° C. and pH 7.0. One of the factors that determines the rate of exchange is the extent to which a particular exchangeable hydrogen is exposed (accessible) to water. The exchange reaction proceeds efficiently only when a particular peptide amide hydrogen is fully exposed to solvent. In a completely unstructured polypeptide chain, all peptide amide hydrogens are maximally accessible to water and exchange at their maximal possible rate, which is approximately (within a factor of 30) the same for all amides; a half-life of exchange in the range of one second at 0° C. and pH 7.0. Exact exchange rates expected for particular amide hydrogens in fully unstructured segments can be reliably calculated from knowledge of the temperature, pH and primary amino acid sequence involved (Molday, et al. Biochemistry 11:150 1972, Bai, et al. Proteins: Structure, Function, and Genetics 17:74-86 1993).

In structured regions of a protein, most peptide amide hydrogens exchange much slower (up to $10^{\wedge 9}$ fold slower) than this maximal exchange rate, as they are not efficiently exposed to solvent. The ratio of exchange rates for a particular amide hydrogen, structured vs. unstructured, is referred to as the exchange protection factor, and directly reflects the free energy change in the atomic environment of that particular hydrogen in the structured state. In this sense, amide hydrogens can be treated as atomic scale sensors of highly localized free energy change throughout a protein and the magnitude of free energy change reported from each of a protein's amides in a folded vs. unfolded state is precisely equal to -RT ln (protection factor) (Bai, et al. Methods Enzymol. 259:344 1995). In effect, each peptide amide's exchange rate in a folded protein directly and precisely reports the protein's thermodynamic stability at the individual amino acid scale. Ranking and comparison of the exchange rates of a protein's amides therefore allows direct and unambiguous identification and localization of structured/unstructured regions of the protein: unstructured regions are those where substantial contiguous stretches of primary sequence exhibit the fastest possible exchange rates, indicative of complete and continuous solvation of the amide hydrogens in such segments, (Englander, et al. Methods Enzymol. 232:26-42 1994, Bai, et al. Methods Enzymol. 259:344 1995). In structured regions, the occasional peptide amide will happen to be fully solvated, and exchange rapidly. However, the typical turn in stable protein structure is accomplished in three or less amino acids, and therefore stretches of four or more continuous rapidly exchanging amides is likely indicative of disorder.

Development of High Resolution, High Throughput Peptide Amide Hydrogen/Deuterium Exchange—Mass Spectrometry (DXMS)

Deuterium exchange methodologies coupled with Liquid Chromatography Mass Spectrometry (LCMS), developed over the past 10 years, presently provide the most effective approach to study proteins larger than 30 kDa in size (Engen, et al. Analytical Chemistry 73:256A-265A 2001). Proteolytic and/or collision-induced dissociation (CID) fragmentation methods allow exchange behavior to be mapped to subregions of the protein (Engen, et al. Analytical Chemistry 73:256A-265A 2001, Hoofnagle, et al. Proceedings, National Academy of Sciences 98:956-961 2001, Resing, et al. J. Am Soc Mass Spectrom 10:685-702 1999, Mandell, et al. Anal. Chem. 70:39487-3995 1998, Mandell, et al. Proc Natl Acad Sci USA 95:14705-10. 1998, Mandell, et al. J. Mol. Biol. 306:575-589 2001, Kim, et al. J Am Chem Soc 123:9860-6. 2001, Kim, et al. Biochemistry 40:14413-21. 2001, Zhang, et al. Protein Sci 10:2336-45. 2001, Kim, et al. Protein Sci 11:1320-9. 2002, Peterson, et al. Biochem J 362:173-81. 2002, Yan, et al. Protein Sci 11:2113-24. 2002). The present invention provides a number of improvements to traditional methodologies and experimental equipment which significantly improve throughput, comprehensiveness, and resolution. As described herein, invention methods are well suited to provide data to refine high throughput structure determination.

Considerable experimental work and time are required to precisely characterize the structure of a polypeptide of interest. In general, the techniques that are the easiest to use and which give the quickest answers, result in an inexact and only approximate idea of the nature of the critical structural features. Techniques in this category include the study of proteolytically generated fragments of the protein which retain binding function; recombinant DNA techniques, in which proteins are constructed with altered amino acid sequence (for example, by site directed mutagenesis); epitope scanning peptide studies (construction of a large number of small peptides representing subregions of the intact protein followed by study of the ability of the peptides to inhibit binding of the ligand to receptor); covalent crosslinking of the protein to its binding partner in the area of the binding site, followed by fragmentation of the protein and identification of cross-linked fragments; and affinity labeling of regions of the receptor which are located near the ligand binding site of the receptor, followed by characterization of such "nearest neighbor" peptides.

Other techniques that are capable of finely characterizing polypeptide three-dimensional structure are considerably more difficult in practice. The most definitive techniques for the characterization of polypeptide structure, and receptor binding sites in particular, have been NMR spectroscopy and X-ray crystallography. While these techniques can ideally provide a precise characterization of relevant structural features, they have major limitations, including inordinate amounts of time required for study, inability to study large proteins, and, for X-ray analysis, the need for protein and/or protein-binding partner crystals.

A critical shortcoming of present high-throughput crystallographic structure determination efforts is the failure to produce crystals for around 80% of the proteins of interest. It is clear that advances in automation and crystallography data analysis have not been matched by a similar pace of progress in methods for generating protein crystals for analysis (Chayen and Saridakis, Acta Crystal. D. Biol. Crystal. 58:921-927, 2002). The process of generating protein crystals suitable for structural analysis is commonly recognized as the most difficult and time-consuming step in the process of a crystallographic structure determination (see, e.g., Wiencek, Ann. Rev. Biomed. Eng. 1:505-534, 1999). Floppy, unstructured regions of proteins can play a dominant role in this problem; the energetics and kinetics of crystallization are often less favorable than for fully structured proteins, and additionally, these regions are often more susceptible to degradation during purification than are structured regions, thus promoting sample heterogeneity.

Measurement of the exchange rates of peptide amide hydrogens within a protein can report its stability at the individual amino acid scale. Essentially, hydrogen exchange can be used to determine a stability map of a protein, reflecting the degree of ordered conformation of all regions of the protein being analyzed. Ranking and comparison of the exchange rates of a protein's amide hydrogens therefore allows direct identification and localization of structured versus unstructured regions of the protein. In the instant invention, hydrogen exchange analysis of the protein is used to identify disordered regions within the protein-stretches of 4 or more amino acids exhibiting very fast amide hydrogen exchange rates, indicating they are fully exposed to solvent at all times. The protein is then admixed with one or more potential structure-forming agents or subjected to altered conditions. Potential structure forming or inducing agents may be identified and/or produced by any of a number of means, including previously performed binding assays, two hybrid screening analysis. Hydrogen exchange analysis may then be repeated on each agent/conditionprotein combination, with assessment of the content and location of stretches of very fast exchanging amides in the protein. Agents/ conditions that slow the exchange of one or more fast-exchanging segments within the protein are thereby identified as inducing structure in such segments of the protein, and are candidates for co-crystallization with the protein.

Hydrogen (Proton) Exchange

When a protein in its native folded state is incubated in buffers containing an isotope of hydrogen (for example, tritium or deuterium labeled water), isotope in the buffer reversibly exchanges with normal hydrogen present in the protein at acidic positions (for example, —OH, —SH, and —NH groups) with rates of exchange which are dependent on each exchangeable hydrogen's chemical environment, temperature, and most importantly, its accessibility to the isotope of hydrogen present in the buffer (see, e.g., Englander et al., Meth. Enzymol. 49:24-39, 1978; Englander et al., Meth. Enzymol. 26:406-413, 1972). Accessibility is determined in turn by both the surface (solvent-exposed) disposition of the hydrogen, and the degree to which it is hydrogen-bonded to other regions of the folded polypeptide. Simply stated, an acidic hydrogen present on amino acid residues which are on the outside (buffer-exposed) surface of the protein and which are hydrogen-bonded to solvent water will often exchange more rapidly with heavy hydrogen in the buffer than will a similar acidic hydrogen which is buried and hydrogen-bonded within the folded polypeptide.

Hydrogen exchange reactions can be greatly accelerated by both acid and base-mediated catalysis; and the rate of exchange observed at any particular pH is the sum of both acid and base mediated mechanisms. For many acidic hydrogens, a pH of 2.2-2.7 results in an overall minimum rate of exchange (Englander et al., Anal. Biochem. 147:234-244, 1985; Englander et al., Biopolymers 7:379-393, 1969;

Molday et al., *Biochemistry* 11:150, 1972; Kim et al., *Biochemistry* 21:1, 1982; Bai et al., *Proteins: Struct. Funct. Genet.* 17:75-86, 1993; and Connelly et al., *Proteins: Struct. Funct. Genet.* 17:87-92). While hydrogens in protein hydroxyl and amino groups exchange with tritium or deuterium in buffer at millisecond rates, the exchange rate of one particular acidic hydrogen, the peptide amide bond hydrogen, is considerably slower, having a half life of exchange (when freely accessible, and freely hydrogen-bonded to solvent water) of approximately 0.5 seconds at 0° C., pH 7, which is greatly slowed to a half life of exchange of 70 minutes at 0° C., pH 2.7. When a polypeptide is in a denatured, unstructured configuration (also termed a "random coil") all of its amide hydrogens can freely exchange with solvent hydrogen. However, the precise rate of exchange varies up to 200 fold from amide to amide in such unstructured configurations, the rate of exchange at each particular amide being determined by localized primary amino acid sequence-dependent effects that can be calculated from a knowledge of the peptide's primary sequence (Bai et al., supra). When peptide amide hydrogens are buried within a folded polypeptide, or are hydrogen bonded to other parts of the polypeptide, exchange half-lives with solvent hydrogens are often considerably lengthened, at times being measured in hours to days.

Hydrogen exchange at peptide amides is a fully reversible reaction, and rates of on-exchange (solvent deuterium replacing protein-bound normal hydrogen) are identical to rates of off-exchange (hydrogen replacing protein-bound deuterium) if the state of a particular peptide amide within a protein, including its chemical environment and accessibility to solvent hydrogens, remains identical during hydrogen exchange conditions.

Hydrogen exchange is commonly measured by performing studies with proteins and aqueous buffers that are differentially tagged with pairs of the three isotopic forms of hydrogen ($^1$H, normal hydrogen; $^2$H, deuterium; $^3$H, tritium). If the pair of normal hydrogen and tritium are employed, it is referred to as tritium exchange; if normal hydrogen and deuterium are employed, as deuterium exchange. Different physicochemical techniques are in general used to follow the distribution of the two isotopes in deuterium versus tritium exchange. The rates of exchange of other acidic protons (—OH, —NH, and —SH) are so rapid that they cannot be followed in these techniques and all subsequent discussion refers exclusively to peptide amide proton exchange.

Tritium Exchange Techniques

Tritium exchange techniques (where the amount of the isotope is determined by radioactivity measurements) have been extensively used for the measurement of peptide amide exchange rates within an individual protein. In these studies, purified proteins are on-exchanged by incubation in buffers containing tritiated water for varying periods of time, optionally transferred to buffers free of tritium, and the rate of off-exchange of tritium determined. By analysis of the rates of tritium on-and off-exchange, estimates of the numbers of peptide amide protons in the protein whose exchange rates fall within particular exchange rate ranges can be made. These studies do not allow a determination of the identity (location within the protein's primary amino acid sequence) of the exchanging amide hydrogens measured.

Extensions of these techniques have been used to detect the presence within proteins of peptide amides which experience allosterically-induced changes in their local chemical environment and to study pathways of protein folding (Englander et al., *Meth. Enzymol.* 26:406-413, 1972; Englander et al., *J. Biol. Chem.* 248:4852-4861, 1973; Englander, *Biochemistry* 26:1846-1850, 1987; Louie et al., *J. Mol. Biol.* 201:765-772, 1988). For these studies, tritium on-exchanged proteins are often allowed to off-exchange after they have experienced either an allosteric change, or have undergone time-dependent folding upon themselves, and the number of peptide amide hydrogens which experience a change in their exchange rate subsequent to the allosteric/folding modifications determined. Changes in exchange rate indicate that alterations of the chemical environment of particular peptide amides have occurred which are relevant to proton exchange (solvent accessibility, hydrogen bonding, etc.). Peptide amide hydrogens which undergo an induced slowing in their exchange rate are referred to as "slowed amides" and if previously on-exchanged tritium is sufficiently slowed in its off-exchange from such amides there results a "functional tritium labeling" of these amides. From these measurements, inferences are made as to the structural nature of the shape changes which occurred within the isolated protein. Again, determination of the identity of the particular peptide amides experiencing changes in their environment is not possible with these techniques.

Several investigators have described technical extensions (collectively referred to as "medium resolution tritium exchange") which allow the locations of particular slowed, tritium labeled peptide amides within the primary sequence of small proteins to be localized to a particular proteolytic fragment, though not to a particular amino acid.

Rosa and Richards were the first to describe and utilize medium resolution tritium techniques in their studies of the folding of ribonuclease S protein fragments (Rosa et al., *J. Mol. Biol.* 133:399-416, 1979; Rosa et al., *J. Mol. Biol.* 145:835-851, 1981; and Rosa et al., *J. Mol. Biol.* 160:517-530, 1982). However, the techniques described by Rosa and Richards were of marginal utility, primarily due to their failure to optimize certain critical experimental steps. No studies employing related techniques were published until the work of Englander and co-workers in which extensive modifications and optimizations of the Rosa and Richards technique were first described.

Englander's investigations utilizing tritium exchange focused exclusively on the study of allosteric changes which take place in tetrameric hemoglobin (a subunit and b subunit 16 kD in size each) upon deoxygenation (Englander et al., *Biophys. J.* 10:577, 1979; Rogero et al., *Meth. Enzymol.* 131:508-517, 1986; Ray et al., *Biochemistry* 25:3000-3007, 1986; and Louie et al., *J. Mol. Biol.* 201:755-764, 1988). In the Englander procedure, native hemoglobin in the oxygenated state is on-exchanged in tritiated water. The hemoglobin is then deoxygenated (inducing allosteric change), transferred to tritium-free buffers by gel permeation column chromatography, and then allowed to off-exchange for 10-50 times the on-exchange time. On-exchanged tritium present on peptide amides which experience no change in exchange rate subsequent to the induced allosteric change in hemoglobin structure off-exchanges at rates identical to its on-exchange rates, and therefore is almost totally removed from the protein after the long off-exchange period. However, peptide amides which experience slowing of their exchange rate subsequent to the induced allosteric changes preferentially retain the tritium label during the period of off-exchange.

To localize (in terms of hemoglobin's primary sequence) the slowed amides bearing the residual tritium label, Englander then proteolytically fragments the off-exchanged hemoglobin with the protease pepsin, separates, isolates and identifies the various peptide fragments by reverse phase high pressure liquid chromatography (RP-HPLC), and determines which fragments bear the residual tritium label by scintillation counting. However, as the fragmentation of hemoglobin proceeds, each fragment's secondary and tertiary structure is lost and the unfolded peptide amide hydrogens become freely accessible to $H_2O$ in the buffer. At physiologic pH (>6), any amide-bound tritium label would leave the unfolded fragments within seconds. Englander therefore performs the fragmentation and HPLC peptide isolation procedures under conditions which minimize peptide amide proton exchange, including cold temperature (4° C.) and use of phosphate buffers at pH 2.7. This technique has been used successfully by Englander to coarsely identify and localize the peptide regions of hemoglobin α and β chains which participate in deoxygenation-induced allosteric changes. The ability of the Englander technique to localize tritium labeled amides, while an important advance, remains low; at best, Englander reports that his technique localizes amide tritium label to hemoglobin peptides 14 amino acids or greater in size, without the ability to further sublocalize the label. Moreover, in Englander's work, there is no appreciation that a suitably adapted exchange technique might be used to identify the peptide amides which reside in the contacting surface of a protein receptor and its binding partner. Instead, these Englander disclosures are concerned with the mapping of allosteric changes in hemoglobin.

Unfortunately, acid proteases are very nonspecific in their sites of cleavage, leading to considerable HPLC separation difficulties. Englander tried to work around these problems, for the localization of hemoglobin peptides experiencing allosteric changes, by taking advantage of the fact that some peptide bonds are somewhat more sensitive to pepsin than others. Even then, the fragments were "difficult to separate cleanly". They were also, of course, longer (on average), and therefore the resolution was lower. Englander concludes, "At present the total analysis of the HX (hydrogen exchange) behavior of a given protein by these methods is an immense task. In a large sense, the best strategies for undertaking such a task remain to be formulated. Also, these efforts would benefit from further technical improvements, for example in HPLC separation capability and perhaps especially in the development of additional acid proteases with properties adapted to the needs of these experiments" (Englander et al., *Anal. Biochem.* 147:234-244, 1985).

Over the succeeding years since this observation was made, no advances have been disclosed which address these critical limitations of the medium resolution hydrogen exchange technique. Most acid-reactive proteases are in general no more specific in their cleavage patterns than pepsin. Efforts to improve the technology by employing other acid reactive proteases other than pepsin have not significantly improved the technique.

Allewell and co-workers have disclosed studies utilizing the Englander techniques to localize induced allosteric changes in the enzyme *Escherichia coli* aspartate transcarbamylase (Burz et al., *Biophys. J.* 49:70-72, 1986; Mallikarachchi et al., *Biochemistry* 28:5386-5391, 1989). Burz et al. is a brief disclosure in which the isolated R2 subunit of this enzyme is on-exchanged in tritiated buffer of specific activity 100 mCi/ml, allosteric change induced by the addition of ATP, and then the conformationally altered subunit off-exchanged. The enzyme R2 subunit was then proteolytically cleaved with pepsin and analyzed for the amount of label present in certain fragments. Analysis employed techniques which rigidly adhered to the recommendations of Englander, utilizing a single RP-HPLC separation in a pH 2.8 buffer.

ATP binding to the enzyme was shown to alter the rate of exchange of hydrogens within several relatively large peptide fragments of the R2 subunit. In a subsequent more complete disclosure (Mallikarachchi, supra), the Allewell group discloses studies of the allosteric changes induced in the R2 subunit by both ATP and CTP. They disclose on-exchange of the R2 subunit in tritiated water-containing buffer of specific activity 22-45 mCi/ml, addition of ATP or CTP followed by off-exchange of the tritium in normal water-containing buffer. The analysis comprised digestion of the complex with pepsin, and separation of the peptide fragments by reverse phase HPLC in a pH 2.8 or pH 2.7 buffer, all of which rigidly adheres to the teachings of Englander. Peptides were identified by amino acid composition or by N-terminal analysis, and the radioactivity of each fragment was determined by scintillation counting. In both of these studies the localization of tritium label was limited to peptides which averaged 10-15 amino acids in size, without higher resolution being attempted.

Beasty et al., (*Biochemistry* 24:3547-3553, 1985) have disclosed studies employing tritium exchange techniques to study folding of the α subunit of *E. coli* tryptophan synthetase. The authors employed tritiated water of specific activity 20 mCi/ml, and fragmented the tritium labeled enzyme protein with trypsin at a pH 5.5, conditions under which the protein and the large fragments generated retained sufficient folded structure to protect amide hydrogens from off-exchange during proteolysis and HPLC analysis. Under these conditions, the authors were able to produce only 3 protein fragments, the smallest being 70 amino acids in size. The authors made no further attempt to sublocalize the label by further digestion and/or HPLC analysis. Indeed, under the experimental conditions they employed (they performed all steps at 12° C. instead of 4° C., and performed proteolysis at pH 5.5 instead of pH in the range of 2-3), it would have been impossible to further sublocalize the labeled amides by tritium exchange, as label would have been immediately lost (off-exchanged) by the unfolding of subsequently generated proteolytic fragments at pH 5.5 if they were less than 10-30 amino acids in size. Additional references disclosing tritium exchange methods include Fromageot et al., U.S. Pat. No. 3,828,102, which discloses using hydrogen exchange to tritium label a protein and its binding partner, and Benson, U.S. Pat. Nos. 3,560,158 and 3,623,840, which discloses using hydrogen exchange to tritiate compounds for analytical purposes.

Deuterium Exchange Techniques

Fesik et al. (*Biochem. Biophys. Res. Commun.* 147:892-898, 1987) disclose measuring by NMR the hydrogen (deuterium) exchange of a peptide before and after it is bound to a protein. From this data, the interactions of various hydrogens in the peptide with the binding site of the protein are analyzed.

Paterson et al. (*Science* 249:755-759, 1990) and Mayne et al. (*Biochemistry* 31:10678-10685, 1992) disclose NMR mapping of an antibody binding site on a protein (cytochrome-C) using deuterium exchange. This relatively small protein, with a solved NMR structure, is first complexed to anti-cytochrome-C monoclonal antibody, and the preformed complex then incubated in deuterated water-containing buffers and NMR spectra obtained at several time intervals. The NMR spectrum of the antigen-antibody complex is examined for the peptide amides which experience slowed hydrogen exchange with solvent deuterium as compared to their rate of exchange in uncomplexed native cytochrome-C. Benjamin et al. (*Biochemistry* 31:9539-0545, 1992) employ an identical NMR-deuterium technique to study the interaction of hen egg lysozyme (HEL) with HEL-specific monoclonal antibodies. While both this NMR-deuterium technique, and medium resolution tritium exchange rely on the phenomenon of proton exchange at peptide amides, they utilize radically different methodologies to measure and localize the exchanging amide hydrogens. Furthermore, study of proteins by the NMR technique is not possible unless the protein is small (generally less than 30 kD), large amounts of the protein are available for the study, and computationally intensive resonance assignment work is completed.

Subsequently, others have disclosed techniques in which exchange-deuterated proteins are incubated with binding partner, off-exchanged, the complex fragmented with pepsin, and deuterium-bearing peptides identified by single stage fast atom bombardment (Fab) or electrospray mass spectroscopy (MS) (Thevenon-Emeric et al., *Anal. Chem.* 64:2456-2358, 1992; Winger et al., *J. Am. Chem. Soc.* 114:5897-5989, 1992; Zhang et al., *Prot. Sci.* 2:522-531, 1993; Katta et al., *J. Am. Chem. Soc.* 115:6317-6321, 1993; and Chi et al., *Org. Mass Spectrometry* 7:58-62, 1993; Engen and Smith, *Anal. Chem.* 73:256A-265A, 2001; Englander et al., *Protein Sci.* 6: 1101-1109, 1997; Dharmasiri and Smith, *Anal. Chem.* 68:2340-2344, 1996; Smith et al., *J. Mass Spectrometry* 32:135-146, 1997; Deng and Smith, *Biochemistry* 37:6256-6262, 1998). In these studies, only the enzyme pepsin is employed to effect enzymatic fragmentation under slowed exchange conditions, and no attempt made to increase the number and quantity of useful fragments produced and studied beyond employing the methods disclosed by Englander and colleagues some decades prior. The resolution of the deuterium-exchange mass spectrometry work disclosed in these publications therefore remained at the 10-14 amino acid level, with the primary limitation of their art being the ability to generate only a small number of peptides with the endopeptidase pepsin, as they employed it. See FIG. 3 for an overview of this method of exchanged deuterium localization.

U.S. Pat. Nos. 5,658,739; 6,291,189; and 6,331,400 issued to Woods, Jr. (each of which is hereby incorporated by reference herein in its entirety), disclose improved methods of determining polypeptide structure and binding sites utilizing hydrogen-exchange-labeled peptide amides, importantly including a method of increasing the resolution of the technique to the 1-5 amino acid level. This increased ability to more precisely localize exchanged amide hydrogens was afforded by the novel use of acid-resistant carboxypeptidases to effect a subsequent progressive sub-fragmentation of the small number of relatively large-sized pepsin-generated peptides initially produced in the method (see FIG. 4 for an overview of the progressive proteolysis method). In these prior methods, finer localization of the labels is achieved by analysis of subfragments generated by controlled, stepwise, sub-degradation ("progressive degradation") of each pepsin-generated, labeled peptide under slowed exchange conditions. According to these prior methods, the protein or a peptide fragment is said to be "progressively", "stepwise" or "sequentially" degraded if a series of fragments are obtained which are similar to those which would be achieved with an ideal exopeptidase. Carboxypeptidase-P, carboxypeptidase Y, and several other acid-reactive (i.e., enzymatically active under acid conditions) carboxypeptidases are specified for use in said progressive degradation of peptides under acidic conditions. To date, no aminopeptidases have been reported that are acid resistant; as a practicality, the only exopeptidases known or likely to be useful for this method are therefore carboxypeptidases.

By performing such measurement of the exchange rates of peptide amide hydrogens within a protein, one can determine its stability at the individual amino acid level. Ranking and comparison of the exchange rates of a protein's amide hydrogens therefore allows direct identification and localization of structured versus unstructured regions of the protein. Despite the utility of such exchange data, the methods used to obtain it have remained labor intensive and time consuming, with substantial limitations in throughput, comprehensiveness and resolution.

High-resolution structures are required for a fundamental understanding of protein structure and function. It is widely anticipated that access to these important structures will be facilitated by novel high-throughput protein structure determination approaches and improvements to conventional crystallographic methods. Proteomic-scale crystallography is one avenue being vigorously pursued by several groups, involving large-scale global efforts (see, e.g., Stevens and Wilson, *Science* 293:519-520, 2001; and Stevens et al., *Science* 294:89-92, 2001).

Despite the availability of many enhancements that facilitate such efforts, high-throughput production of stable protein constructs that suitably crystallize continues to be a serious bottleneck. While definition of successful constructs for protein production has long been a problem for conventional crystallography, the inadequacies of current approaches are particularly acute and costly for structural genomics efforts that presently show only a 10-20% success rate in target crystallization. Bacterial genomes are currently the focus of many of the structural genomics efforts. However, a switch to higher eukaryotes, such as mouse and human, will entail even lower success rates, due in part to more complex and higher molecular weight proteins.

Thus, there remains a need in the art for improved simple, robust, quick and efficient methods whereby the structure of a protein of interest can be analyzed to efficiently define protein domain boundaries, the location of unstructured or floppy regions between or within domains, as well as disordered regions within single-domain proteins; and then employed to refine and optimize the processes of crystallization and crystallographic structure determination in a high-throughput manner.

SUMMARY OF THE INVENTION

The present invention provides enhanced methods for crystallographic structure determination of a protein of interest through the use of hydrogen exchange analysis to identify structure forming agents and conditions that can induce structure in proteins that are partially unstructured when isolated from their natural binding partners or interactors. Preferred methods of the present invention employ novel high-resolution hydrogen exchange analysis. In some embodiments of the invention, methods of hydrogen exchange analysis comprise fragmentation of a labeled protein using methods described in U.S. Pat. Nos. 5,658,739; 6,331,400, and 6,291,189, the entire disclosures of which are incorporated herein by reference. In other embodiments of the invention, the hydrogen exchange analysis allows for high-throughput structural determinations due to simplifications of the protein fragmentation methods described in U.S. Pat. Nos. 5,658,739; 6,331,400, and 6,291,189.

The invention provides a process by which the disordered regions of many proteins can be induced to adopt a structured, functionally relevant form by providing the protein with suitable structure-stabilizing binding partner(s). The structurally stabilized binding pair may then be co-crystallized, diffraction data obtained, and the stabilized, functionally relevant structure of the previously disordered protein determined.

In preferred embodiments, the invention employs deuterium exchange mass spectrometry (DXMS) analysis to identify disordered regions in proteins and then to further guide the identification of binding partners for the protein that are capable of inducing structure in the previously identified disordered regions of the protein.

According to a first aspect of the present invention, there are provided methods for crystallographic structure determination. Such methods comprise performing hydrogen exchange experiments to identify structure-forming agents and/or conditions, including protein binding partners for proteins that induce structure within, or otherwise stabilize unstructured regions of the proteins, and then subjecting the mixture if proteins and identified, specifically interacting binding partners to co-crystallization, followed by x-ray diffraction analysis.

In one embodiment, such methods comprise performing hydrogen exchange studies that first identify unstructured regions of proteins, and then performing studies of said protein after it is admixed or otherwise interacted with each of a number of candidate structure-inducing binding partners, and performing repeat hydrogen exchange studies to identify binding partners that induce structure in at least one unstructured regions of said protein. Said protein and identified structure-forming binding partner are then subjected to co-crystallization. Identifying unstructured regions in the protein by hydrogen exchange analysis preferably comprises the steps of (a) generating a hydrogen exchange stability map of said protein by hydrogen exchange analysis, and (b) identifying unstructured regions of said protein.

The hydrogen exchange analysis comprises determining the quantity of isotopic hydrogen and/or the rate of exchange of hydrogen at a plurality of peptide amide hydrogens exchanged for isotopic hydrogen in a protein labeled with a hydrogen isotope other than $^1H$, such as deuterium or tritium.

In one preferred embodiment, hereinafter referred to as "progressive proteolysis" (as defined in U.S. Pat. No. 6,291,189, column 7, line 58 through column 8, line 33) the process of determining the quantity of isotopic hydrogen and/or the rate of exchange comprises: (a) fragmenting the labeled protein into a plurality of fragments under slowed hydrogen exchange conditions; (b) identifying which fragments of the plurality of fragments are labeled with isotopic hydrogen; (c) progressively degrading each fragment of the plurality of fragments to obtain a series of subfragments, wherein each subfragment of the series is composed of about 1-5 fewer amino acid residues than the preceding subfragment in the series from one end but with preservation of the other end of the subfragment series; (d) measuring an amount of isotopic hydrogen associated with each subfragment; and (e) correlating said amount of isotopic hydrogen associated with each subfragment with an amino acid sequence of the fragment from which said subfragment was generated, thereby determining the quantity of isotopic hydrogen and/or the rate of exchange of a plurality of peptide amide hydrogens exchanged for isotopic hydrogen in a protein labeled with a hydrogen isotope other than $^1H$.

In one aspect of the invention, the step of progressively degrading comprises contacting the fragments with an acid resistant carboxypeptidase, for example, carboxypeptidase P, carboxypeptidase Y, carboxypeptidase W, carboxypeptidase C, or combinations of any two or more thereof.

In another preferred embodiment of the invention, hereinafter referred to as the "improved proteolysis" method, the process of determining the quantity of isotopic hydrogen and/or the rate of exchange comprises: (a) generating a population of sequence overlapping fragments of said labeled protein by treatment with at least one endopeptidase or combination of endopeptidases under conditions of slowed hydrogen exchange, and then (b) deconvoluting fragmentation data acquired from said population of sequence-overlapping endopeptidase-generated fragments. This improved method dramatically speeds and modulates the sites and patterns of proteolysis by endopeptidases so as to produce highly varied and highly efficient fragmentation of the labeled protein in a single step, thereby avoiding the use of carboxypeptidases completely.

In one aspect, endopeptidase fragments are generated by cleaving said protein with at least one endopeptidase selected from the group consisting of a serine endopeptidase, a cysteine endopeptidase, an aspartic endopeptidase, a metalloendopeptidase, and a threonine endopeptidase. In a preferred method, endopeptidase fragments are generated by cleaving said protein with pepsin. Alternatively, endopeptidase fragments may be generated by cleaving said protein with newlase or *Aspergillus* protease XIII, or by more than one endopeptidase used in combination.

In preferred embodiments, invention methods measure the mass of peptide fragments, for example, utilizing mass spectrometry, to determine the presence or absence and/or quantity of an isotope of hydrogen on an endopeptidase fragment. Fragmentation data is deconvoluted by comparing the quantity and rate of exchange of isotope(s) on a plurality of sequence-overlapping endopeptidase-generated fragments with the quantity and rate of exchange of isotope(s) on at least one other endopeptidase fragment, wherein said quantities are corrected for back-exchange in an amino acid sequence-specific manner.

According to another aspect of the present invention, there are provided methods for crystallographic structure determination of a protein comprising: (a) co-expressing proteins and candidate structure-forming binding partners in any of a number of protein expression systems (for example, in vitro, bacterial, baculoviral, mammalian) optionally co-purifying them with each other, and then performing hydrogen exchange studies to identify binding partners that induce structure in at least one region of the proteins, and (b) subjecting to co-crystallization and structure determination said binding partner and protein.

According to another aspect of the present invention, there are provided methods for crystallographic structure determination of a protein comprising: (a) identifying unstructured regions in the said protein by hydrogen exchange analysis: (b) systematically modifying the incubation buffer and co-factors that are admixed with the protein, (pH, salts, small-molecule binding partners) followed the performing hydrogen exchange analysis on the resulting agent-modified protein solution to identify conditions that can stabilize at least one region of the protein. (c) subjecting to crystallization and structure determination the protein as present in said agent-modified solution conditions.

According to another aspect of the present invention, there are provided methods for crystallographic structure determination of a protein comprising: (a) selecting a protein that is resistant to crystallization, or that forms crystals that do not diffract X-rays sufficient for structure determination; (b) identifying unstructured regions in said protein by hydrogen exchange analysis; (c) identifying one or more co-factors, binding partners, or agent-modified solution constituents that can induce at least one structured region in the protein, as detected by hydrogen exchange analysis. (d) subjecting to co-crystallization and structure determination said one or more binding partners, co-factors, or agent-modified solution conditions admixed with the protein.

According to another aspect of the present invention, there are provided methods of refining a crystallographic structure determination of a protein of interest. Such methods comprise comparing an initial crystallographic structure determined using crystal(s) of the protein to at least one other crystallographic structure determined using crystal(s) derived from co-crystallization of the protein with structure-inducing agents (co-factors, binding partners, solution conditions). The agents that can induce structure in at least one region of the protein is (are) identified by generating a hydrogen exchange stability map of the native protein and identifying unstructured regions of the protein and boundaries between structured and unstructured regions of the protein using hydrogen exchange analysis. A desired structure-forming agent is one that induces least one unstructured region thus identified, or a portion thereof to form structure in the protein.

According to another aspect of the present invention, there are provided methods of crystallization of a protein of interest. Such methods comprise comparing an initial hydrogen exchange stability map of the protein to at least one other hydrogen exchange stability map of the protein after it is admixed with a structure-inducing agent. The protein, along with one or more agents that induce an improved (more stable) hydrogen exchange stability map are then subjected to co-crystallization. According to a further aspect of the present invention, there are provided methods of crystallographic structure determination of a protein of interest, comprising comparing an initial hydrogen exchange stability map of the protein to at least one other hydrogen exchange stability map of protein after it is admixed with a structure-inducing agent. Agents that induce in the protein improved hydrogen exchange stability maps are then subjected to co-crystallization and structure determination.

According to another aspect of the present invention, there are provided methods of characterizing conformational differences between a protein in a solution and the same protein when agent-modified by a structure-forming agent, comprising comparing a hydrogen-exchange analysis characterization of said protein with and without the agent.

According to another aspect of the present invention, there are provided methods to identify a protein that is dependent on structure-inducing agents for stability. Such methods comprise comparing the stability map of said protein in its physiologic milieu to the stability map of said protein in a purified state; and detecting regions of said protein that are unstructured in said purified state as compared to said physiologic milieu. In preferred embodiments, the physiologic milieu is selected from the group consisting of blood, plasma, a cellular membrane, a whole cell, and a whole organism.

According to another aspect of the present invention, there are provided methods of identifying a structure-inducing agent. Such methods comprise comparing the stability map of a protein in the presence of a potential structure-inducing agent to the stability map of said protein in the absence of said potential structure-inducing agent; and identifying as a structure-inducing agent an agent that interacts with said protein to produce a decreased content of unstructured regions.

BRIEF DESCRIPTION OF THE FIGURES

FIG. 5A depicts a ten-second amide hydrogen/deuterium exchange map for TM0449. The horizontal bars are the protein's pepsin-generated fragments that had been produced, identified, and used as exchange rate probes in the subsequent 10-second deuteration study. The number of deuterons that went on to each peptide in 10 seconds is indicated by the number of grey residues in each peptide. Deuterium labeling was manually assigned to residue positions within the protein by first optimizing consensus in deuterium content of overlapping peptide probes, followed by further clustering of labeled amides together in the center of unresolved regions (with vertical bars indicating the range of possible location assignments), generating the consensus map at the top, in which two extensive segments are seen to be deuterium labeled: 1 (Phe 31-Glu 38) and 2 (Ser88-Lys 93). FIG. 5B shows the electron density of the crystal indicates two regions of disordered sequence, corresponding to the segments 1 and 2. FIGS. 5C and 5D show detailed electron density maps are shown, in which density is not visualized between the Phe 31 to Glu 39 and Ser 88 to Ser 95 regions of the TM0449 3-D structure. DXMS-determined disorder constitutes 6.4% of this protein's sequence.

FIG. 8 collectively illustrates the exchange maps of the *Thermotoga maritima* proteins studied herein (SEQ. ID.

Nos. 1-21 are shown). Percentages indicate the amount of rapid exchange in amino acid segments of four or more residues, as a percentage of the entire sequence.

Figure 11:
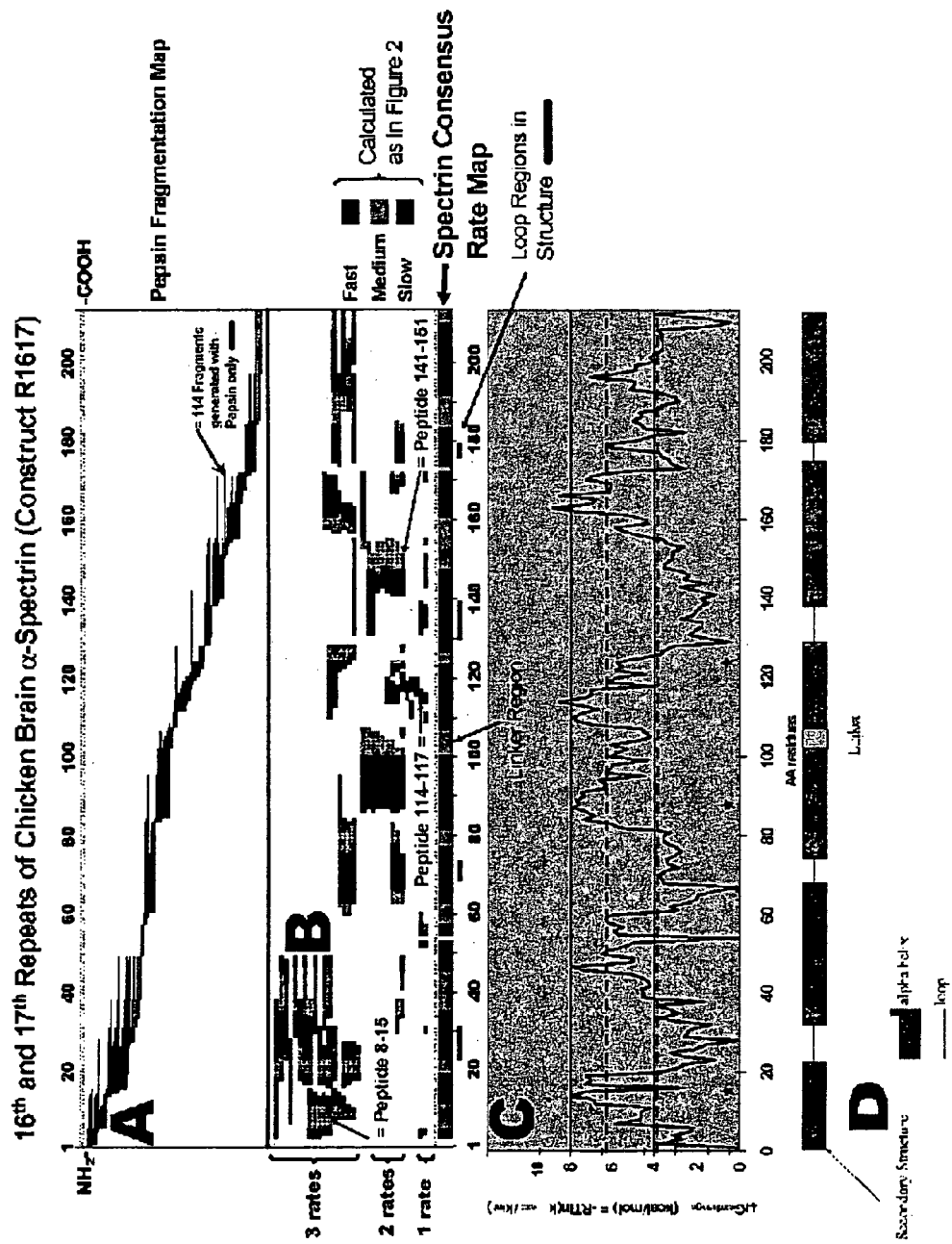

The multiple panels of FIG. 11 collectively illustrate the construction of low and high resolution exchange rate maps for spectrin construct R1617. Panel 11A presents a pepsin fragmentation map; panel 11B presents a spectrin consensus map; panel 11C presents a consensus deconvolution plot (based on the spectrin consensus rate map presented in FIG. 11B); and panel 11D shows the fragmentation pattern obtained when Spectrin was fragmented with the combination of pepsin and Fungal protease XIII.

Figure 12:
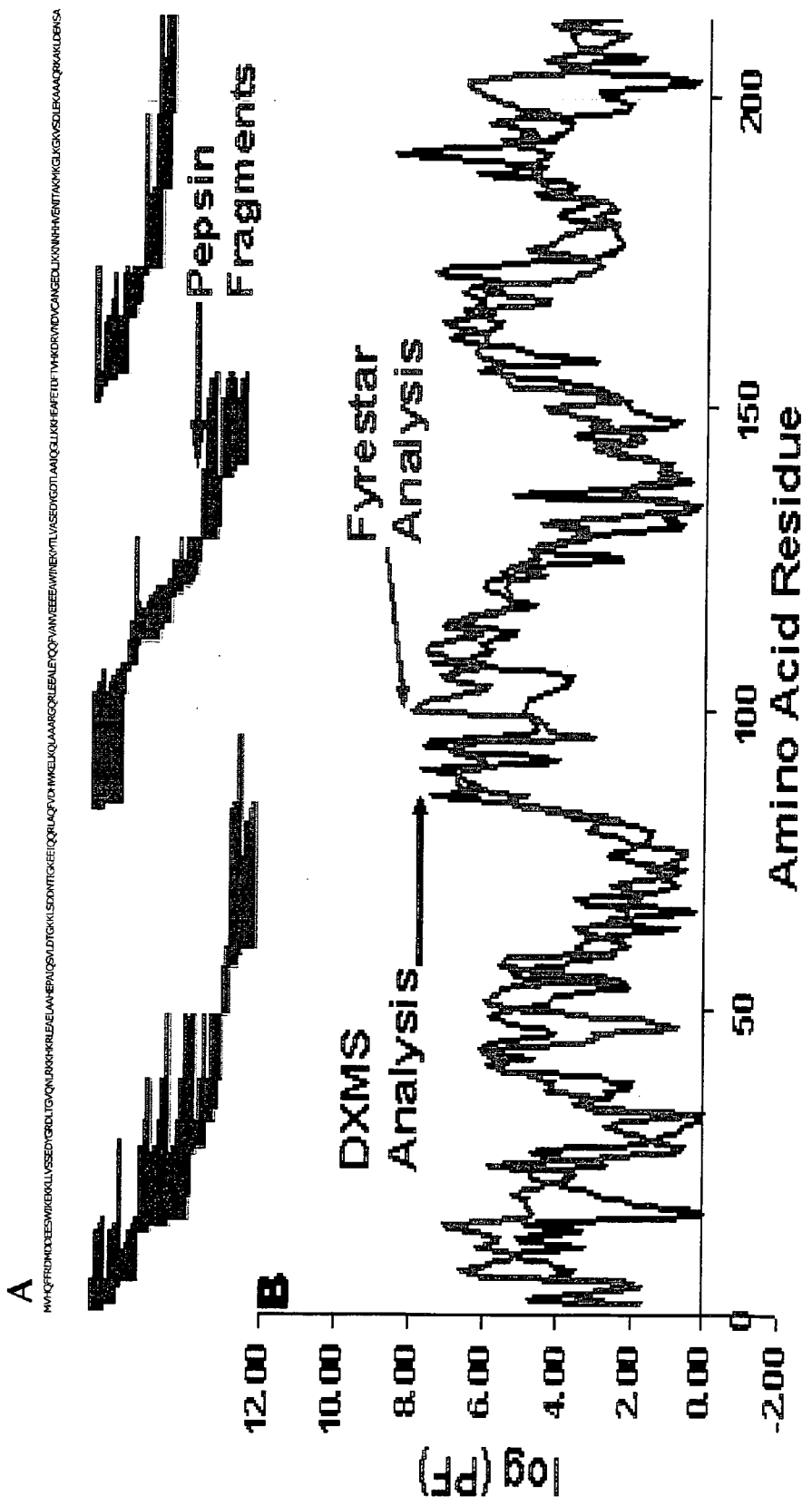

FIG. 12A presents a pepsin fragmentation map for spectrin construct R1617, and FIG. 12B illustrates a comparison of high resolution exchange rate maps obtained from DXMS data (black lines) versus COREX analysis (grey lines) for spectrin construct R1617.

Figure 13:
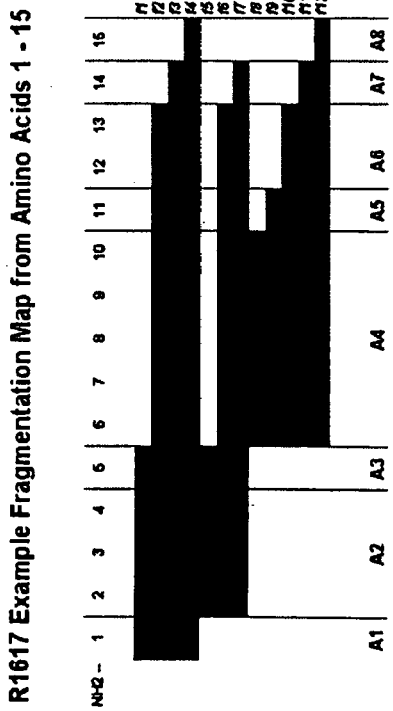

FIG. 13A shows an example fragmentation map from amino acids 1-15 of R1617, and FIG. 13B illustrates a linear programming-based approximation for R1617.

Figure 14:
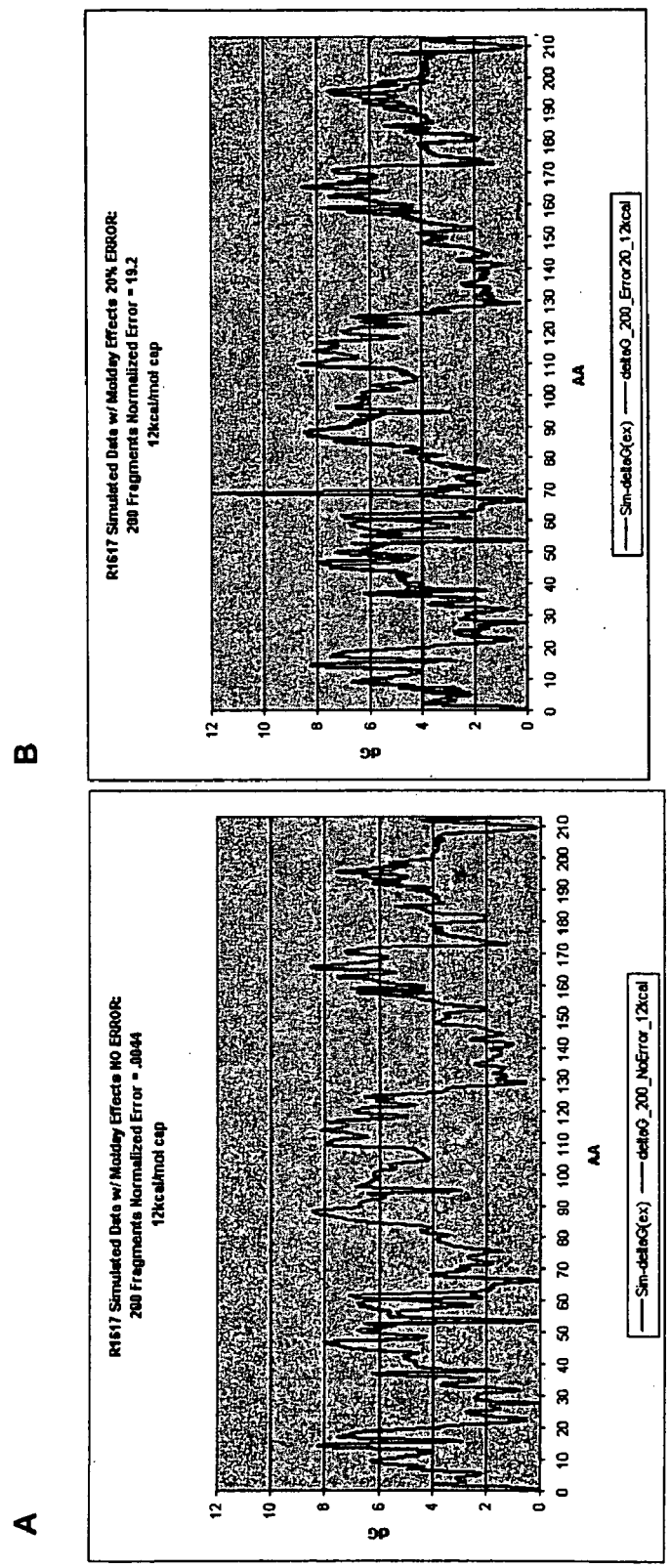

The two panels of FIG. 14 illustrate the results of validation studies and the ability of HR-DXMS deconvolution algorithm and software to correctly calculate exchange rate profiles for simulated data derived from COREX analysis of a spectrin construct with (FIG. 14B) and without (FIG. 14A) introduced error.

Figure 15:
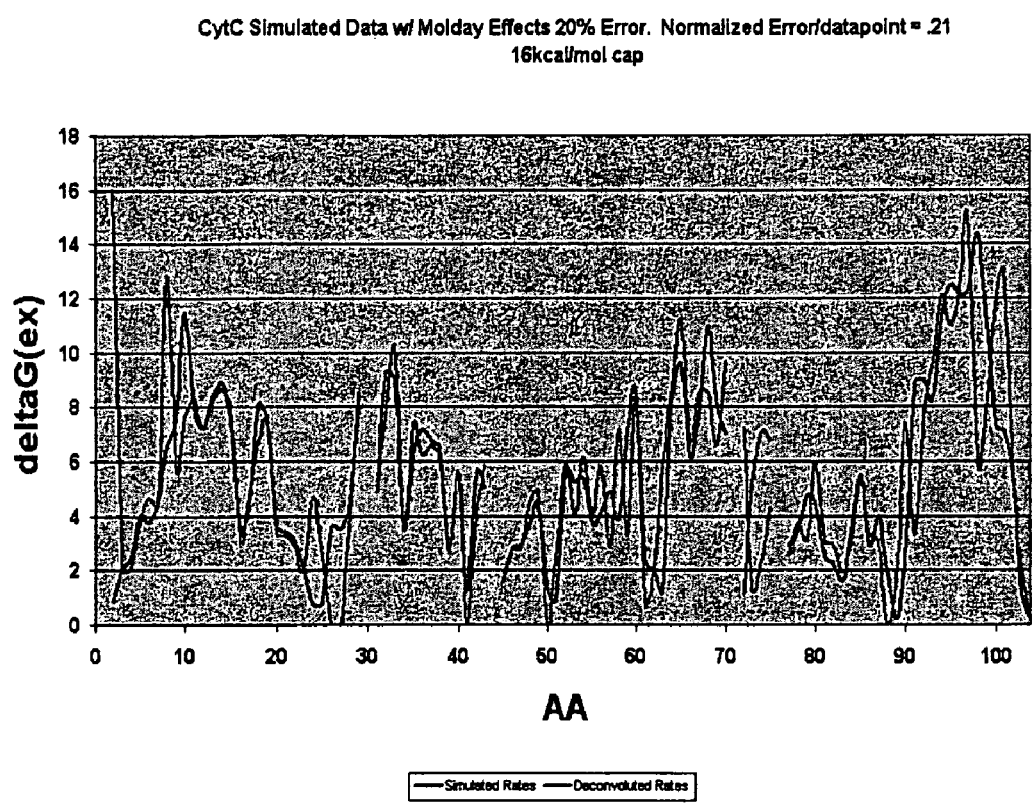

FIG. 15 illustrates the results of validation studies and the ability of HR-DXMS deconvolution algorithm and software to correctly calculate exchange rate profiles for simulated data derived from NMR measurements of horse cytochrome c.

DETAILED DESCRIPTION OF THE INVENTION

Formation of suitably diffracting crystals remains the principal bottleneck in the determination of protein structure by X-ray crystallography. Disordered regions within proteins are thought to be a principal reason for crystallization failure. Previously disclosed methods utilize DXMS to define disordered regions in proteins, and then guide the design of deletion constructs of the protein that are depleted of the identified disordered regions for crystallization study. However, many of the disordered regions so removed can, in the proper context, assume functionally important stable structure, as when the protein is allowed to interact with suitable structure-stabilizing binding partners. Access to these important structural features is lost in the deletion construct method. Furthermore, when multiple unstructured regions interrupt the primary sequence of the target protein, the deletion construct method becomes increasingly less tenable for several reasons. The instant invention provides access to the majority of such functionally relevant structural features in partially to substantially disordered target proteins.

Many overall well-structured proteins contain unstructured regions (see e.g., Wright and Dyson, *J. Mol. Biol.* 293:321-331, 1999). For many proteins, these disordered regions serve primarily as passive linkers or between structurally autonomous domains. For others, such regions are critical to the proper function of the protein, and become ordered when they interact with binding partners that provide the initially disordered regions with structure-stabilizing atomic contacts (tertiary and/or quaternary). Regardless of their functional role, such unstructured regions they can inhibit or prevent crystallization of the well-folded regions. This problem has been apparent for years, but its full extent is difficult to discern from the published literature. In some instances, proteins may crystallize with some floppy regions, either at their ends or within short internal stretches. In many other instances, it is not known why a particular protein does not crystallize, even with seemingly pure protein. Crystallographic structure determination would be facilitated by the ability to rapidly and precisely define structured/unstructured regions of a target and to further guide the identification of binding partners that, in effect, abolish disorder in such regions by providing structure-stabilizing tertiary contacts. Co-crystallization efforts with stabilized protein pairs might succeed in cases where crystallization of the isolated binding partners fails.

Recently completed experiments indicate that DXMS technology is capable of providing such guidance. Twenty-four *Thermotoga maritima* proteins were prepared at the Joint Center for Structural Genomics (JCSG). Six of them had crystallized well and had solved structures, while the majority had failed to crystallize sufficiently well for crystallographic study. pH "quenched" samples of the proteins were batch-processed in a single 48 hour automated DXMS run to acquire data for fragmentation map generation (1.0 M GuHCl, 30 seconds pepsin digestion used). DXMS Software was then used over four days to identify peptide fragments for each protein and generate fragmentation maps. Good to excellent fragmentation maps were generated for all but three of the proteins using the single denaturation condition employed in this experiment.

These twenty-one proteins were then on-exchanged in deuterated buffer for 10 seconds at pH 7.0. on ice, quenched with 0.5% formic acid containing 1.0 M GuHCl, and then snap-frozen on dry ice, and stored at −80 degrees C. until automated DXMS analysis. Data on the deuterated sample set was acquired in a single automated 30 hour run, and subsequent data reduction performed over one week on the DXMS software.

Figure 6:
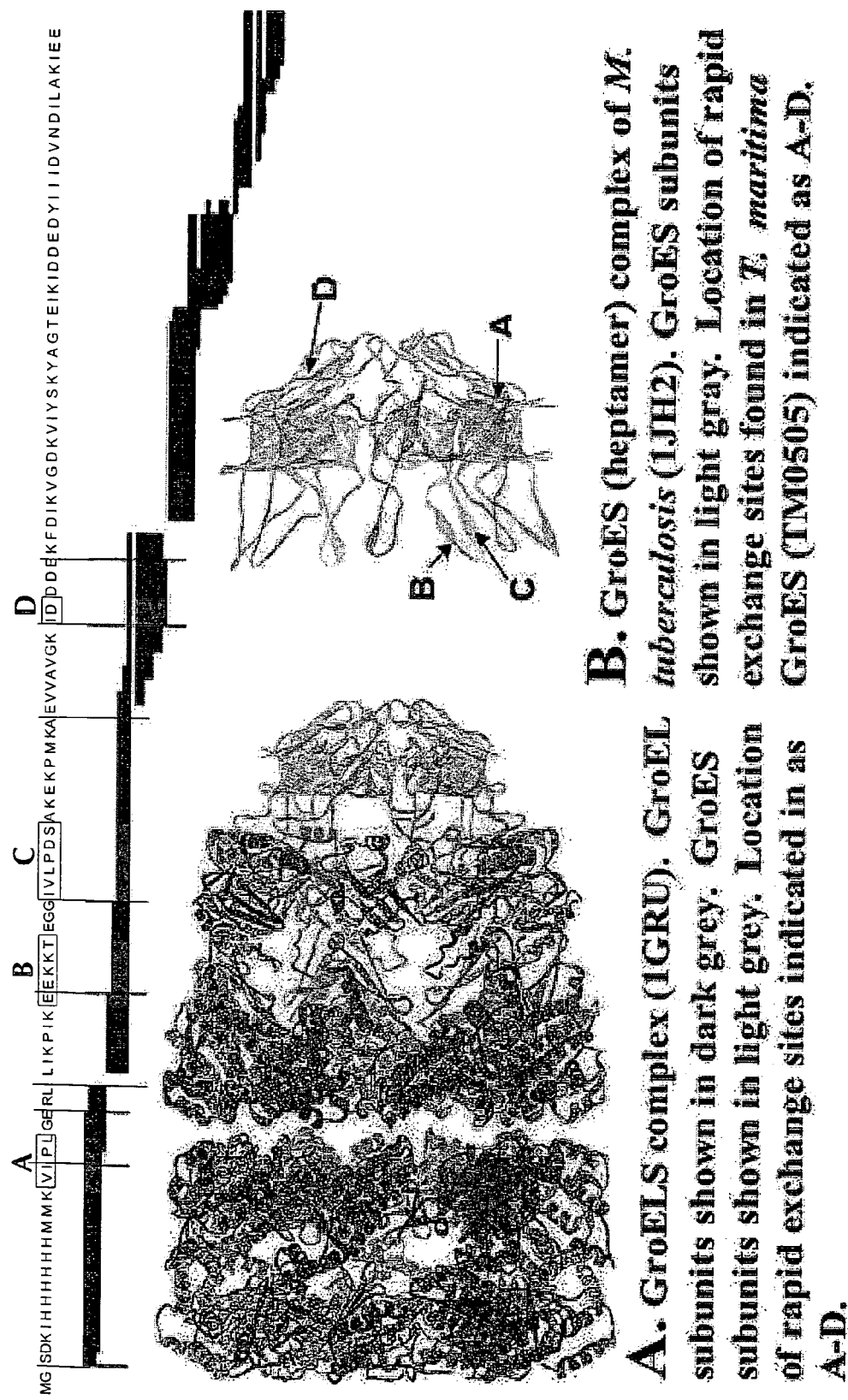
FIG. 6 illustrates the on-exchange map of TM0505 and indicates four internal segments (A, B, C and D) of rapidly exchanging amides, The internal segments are mapped onto the crystal structure of the GroES protein homolog of TM0505. The *M. tuberculosis* GroEL subunit is shown in dark grey and the heptamer complex of *M. tuberculosis* GroES subunits is shown in light gray. The homologous location of rapid exchange sites in the *T. maritima* protein are indicated in light grey. Disorder constitutes 16.3% of this protein's sequence.
Figure 7:
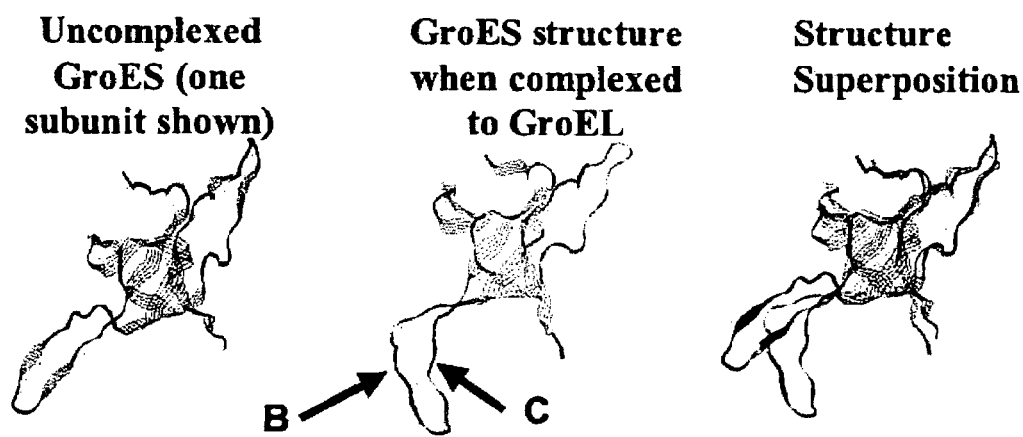
FIG. 7 illustrates the hydrogen exchange and structural behavior of the very rapidly-exchanging regions (B and C) of TM0505 that, while unstructured in isolated GROES, become structured upon binding of GroES to GroEL.
Figure 8A:
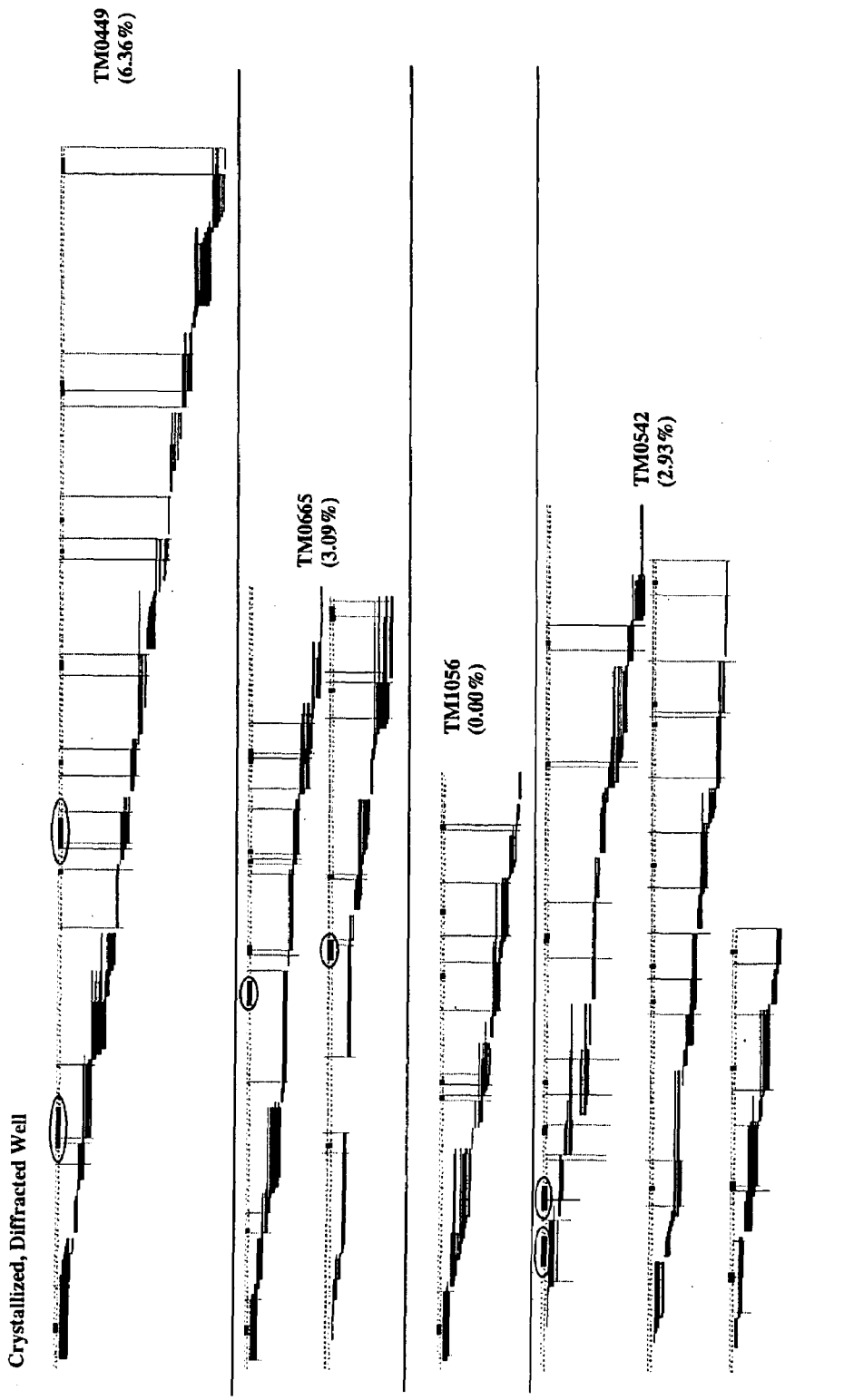
FIGS. 8A and 8B are proteins that crystallized and diffracted well.
Figure 8B:
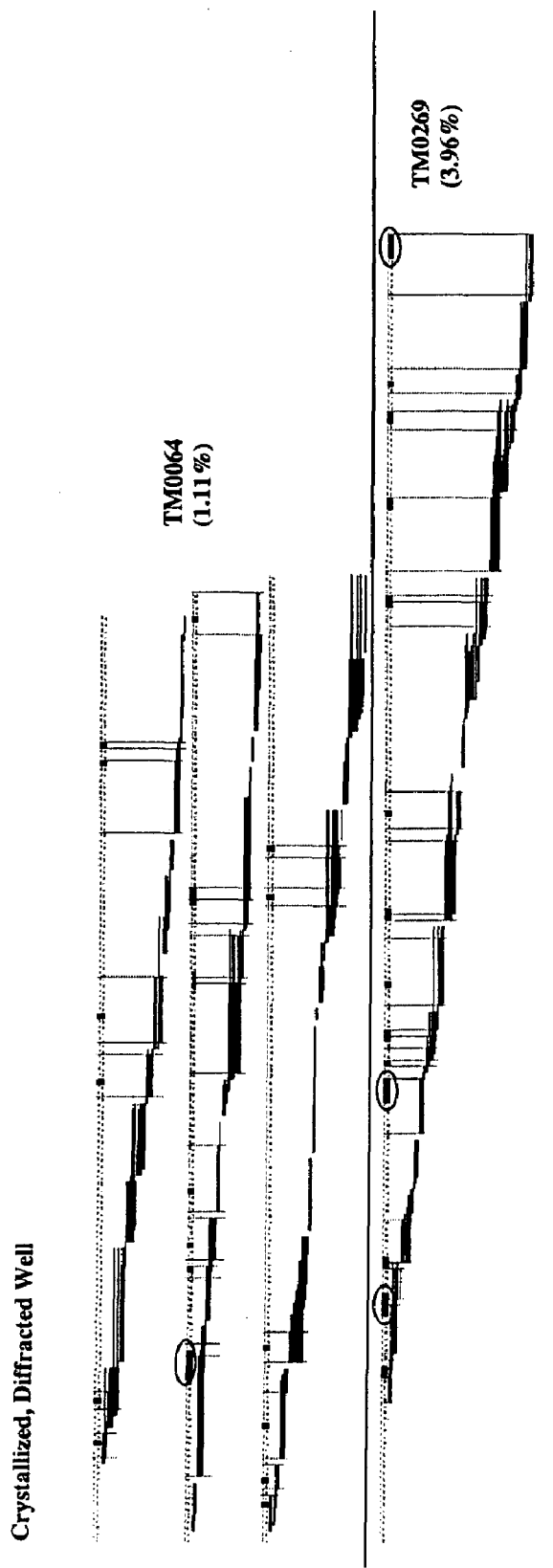
Figure 8C:
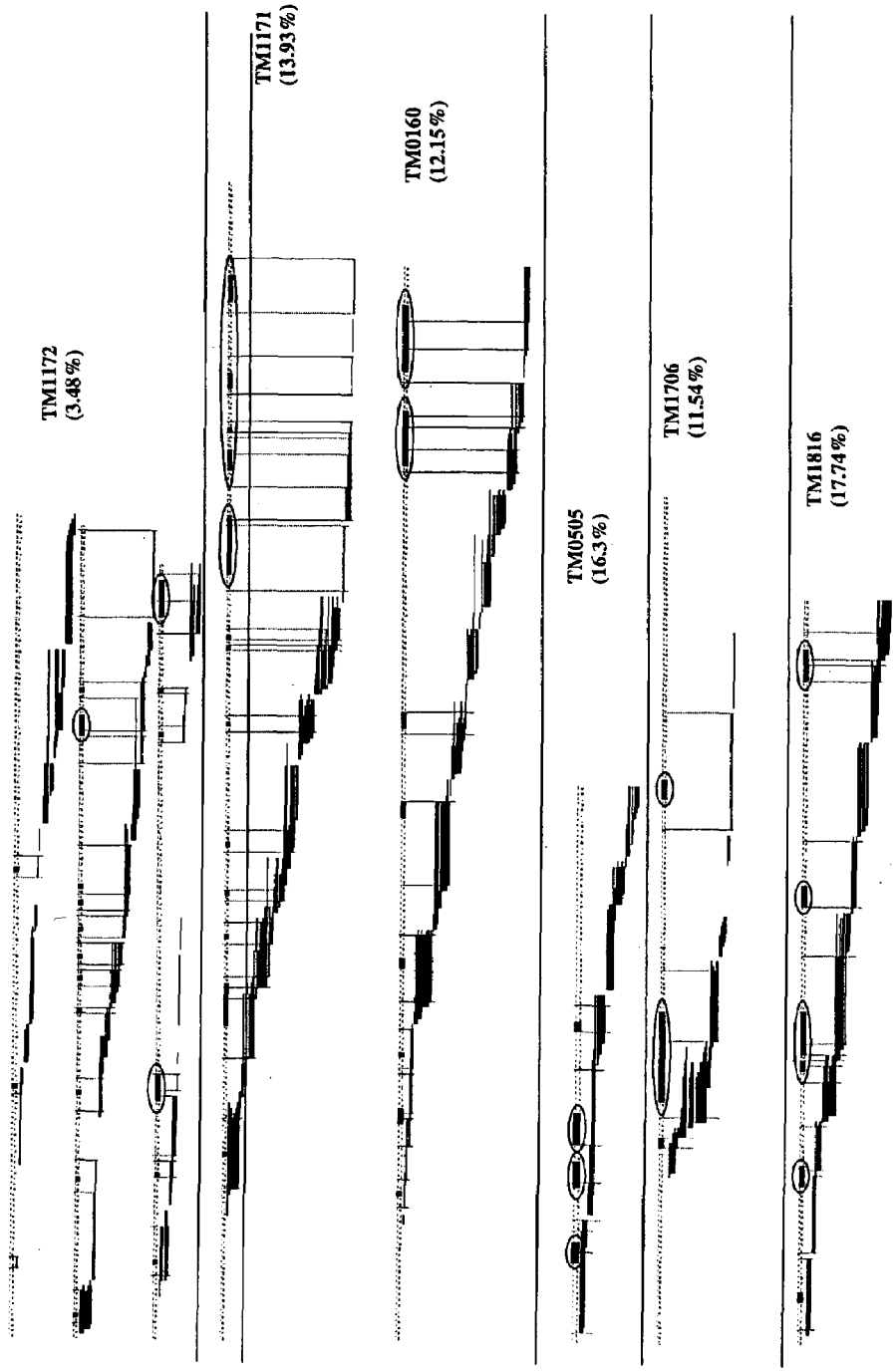
FIGS. 8C-8E are proteins that did not crystallize or had poor diffraction properties. Dark regions indicated fast exchanging amides and clear regions indicate stretches of no exchange. Regions of four or more fast exchanging amides are circled.
Figure 8D:
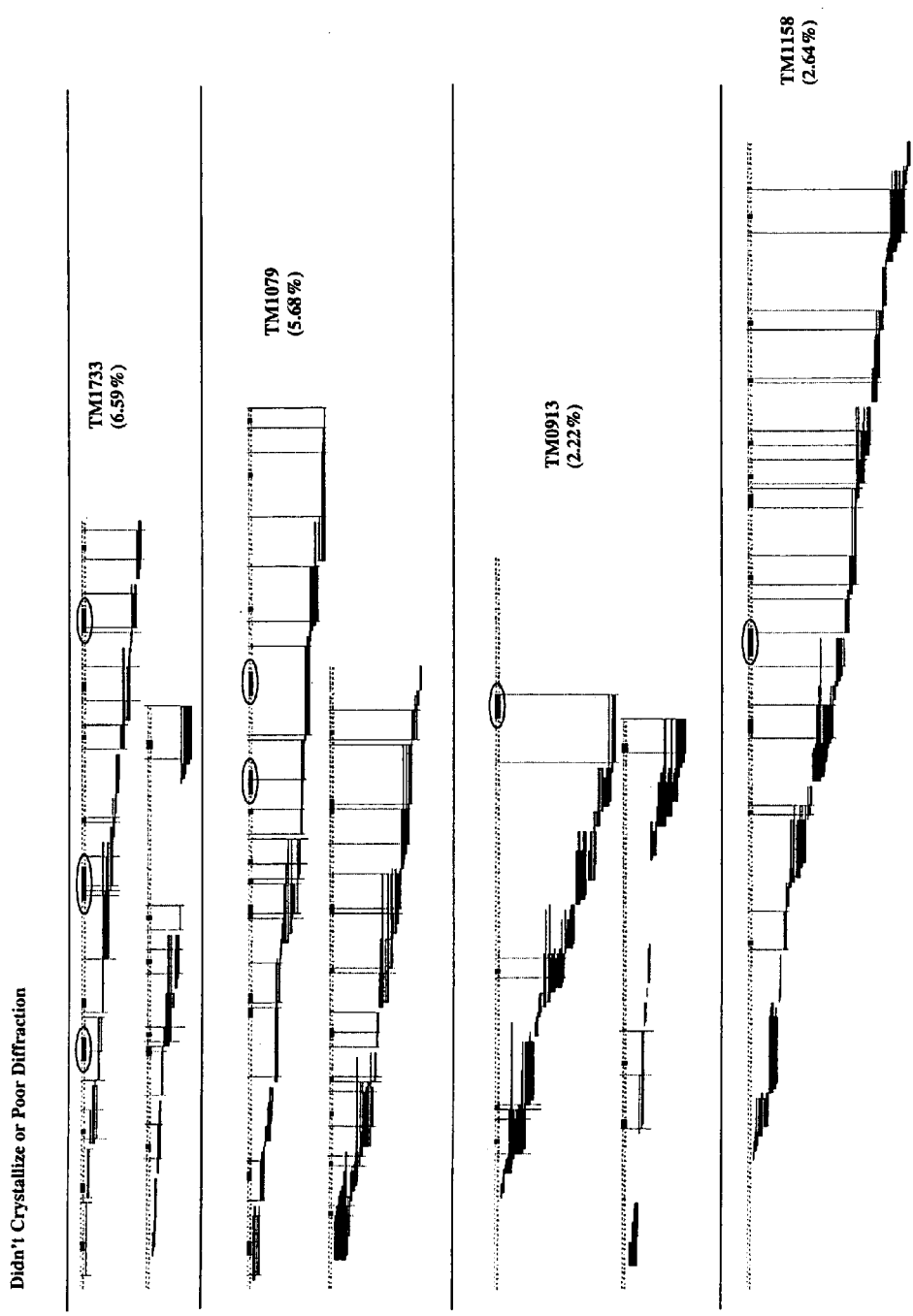
Figure 8E:
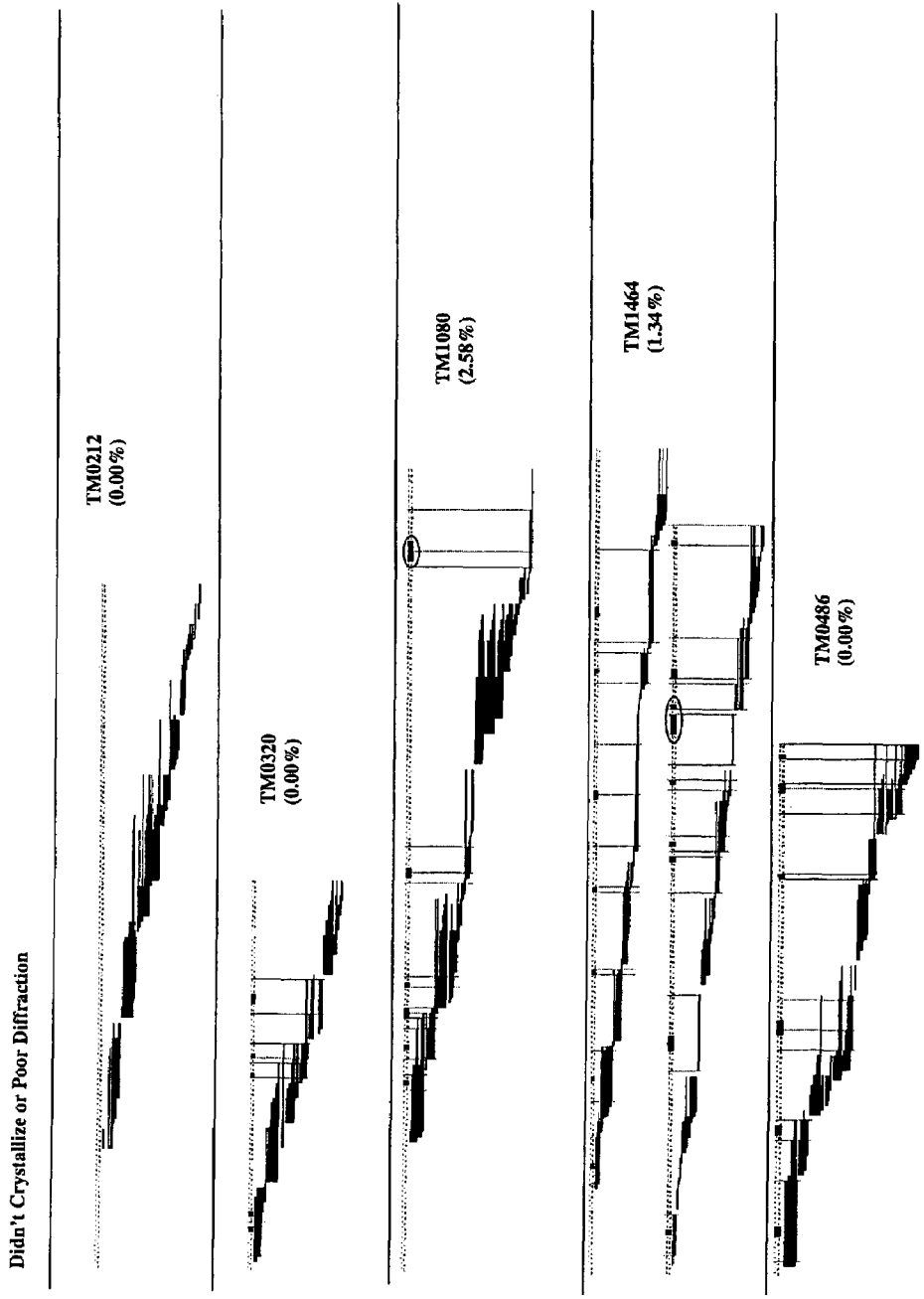

The DXMS rate map for one of the proteins, TM0505, demonstrated rapid exchange in three segments containing four or more residues, constituting 16% of its sequence (see FIGS. 6 and 7). While this protein had produced very poorly diffracting crystals, it is a very close primary-sequence homolog of the groES heat shock protein of *M. tuberculosis*, for which a crystal structure had been previously obtained, both as the isolated protein and as the groELS complex with the groEL subunit. The groEL-binding surface of the groES subunit exhibits marked conformational change upon binding. When the *T. maritima* residues with rapid exchange in four or more contiguous residues were decorated upon the *M. tuberculosis* structures, they localized to a remarkable degree to the residues that make contacts with the groEL binding surface. This result strongly suggested that these residues are highly disordered in solution when not complexed to groES, but become structured upon binding to form the groELS complex. This is a demonstration of the ability of DXMS-determined exchange rate analysis to identify disordered regions that form structure in the context of a stabilizing binding partner.

Large, rapidly exchanging regions of protein kinase A (PKA) regulatory subunits dramatically slow their rates of exchange when they bind to either anchoring proteins (DAKAP2) or PKA catalytic subunits, and this has been interpreted as evidence for quaternary contact-mediated structure stabilization (Burns et al., *Protein Science,* 11(S1): 185, 2002).

Several years ago, attempts to crystallize the full length RIα regulatory subunit had repeatedly failed until, by chance, deletion constructs were prepared that were devoid of large segments (the N-terminal 19 amino acid (aa) and an internal 30 aa segment, 80-110), and crystallized well. Recent DXMS studies of RIα directly indicate that these entire segments exchange very rapidly, being fully deuterated at the earliest on-exchange time measured. Furthermore, these are the same rapidly exchanging regions of RIα that dramatically slow in exchange when complexed with the PKA catalytic subunit. A similar phenomenon is likely occurring in the formation of the groELS complex. Taken together these results indicate that, if appropriately employed, DXMS can guide the identification of structure-inducing binding partners for particular failed crystallographic target proteins that contain substantial amounts of binding surface disposed unstructured sequence, allowing the pair to be studied with co-crystallization efforts.

Figure 3:
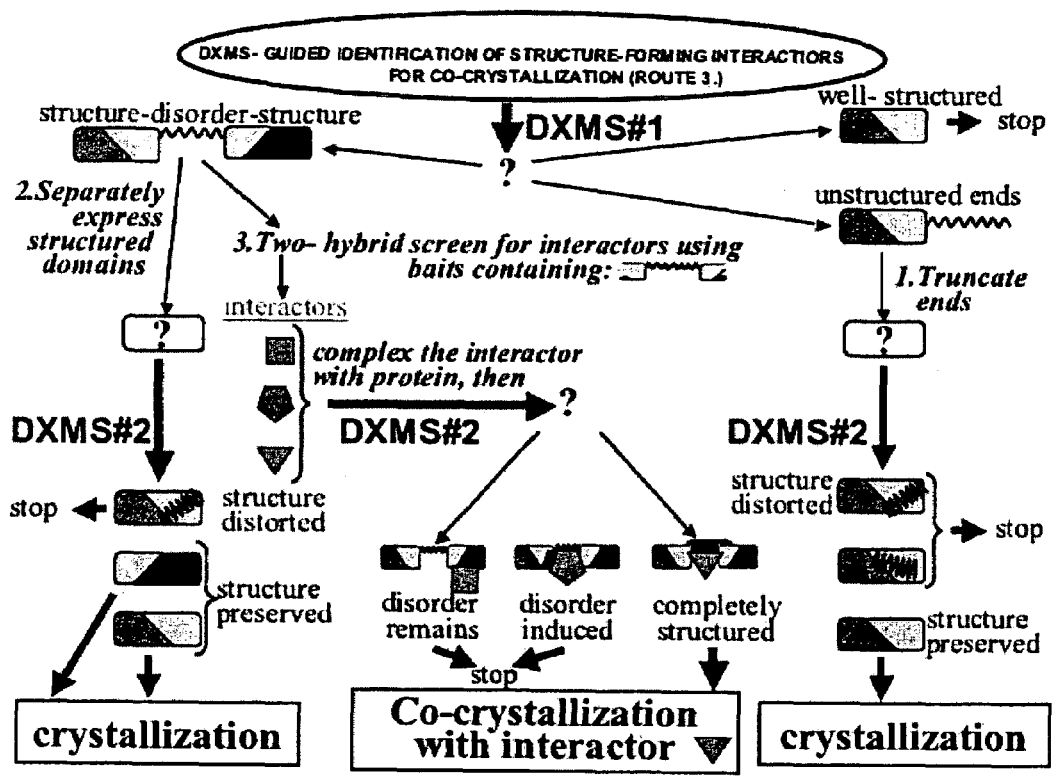
FIG. 3 illustrates exemplary methods by which DXMS data can be used to guide protein crystallization. Path 3 illustrates a preferred embodiment of the present invention, as applied to the identification of binding partner proteins that can induce desired structure of unstructured regions within the target protein upon binding (disorder indicated by short "sawtooths" within figures). Paths 1 and 2 involve design and construction of amino-acid-sequence-modified forms of the protein under study, including deletion mutants, methods that are the subject of other patent applications.

A preferred embodiment of the instant invention is shown schematically in FIG. 3. An initial study (DXMS # 1, FIG. 3) to define and select target proteins that have failed to crystallize that contain substantial stretches of very rapidly exchanging primary sequence. In a preferred embodiment, four or more contiguous residues with rapid exchange are taken as signifying disorder. Any of a number of methods to produce and identify proteins or other molecules that can bind to the target protein may be utilized, a preferred approach being that of 2-hybrid methodology. In approaches in which defined "bait" constructs are produced to isolate and identify "prey" interactors, the DXMS data obtained in DXMS #1 can be used to guide the construction of the bait: it should contain the disordered region(s) identified in the isolated target protein A repeat DXMS analysis (DXMS # 2, FIG. 3) is performed on each target protein-identified interactor pair to further identify interactors that specifically abolish the previously identified target protein sequence disorder. Structure-stabilizing interactors so identified are then employed in co-crystallization studies with the target, as shown in path 3 of FIG. 3.

While the instant invention does not require mutation of the target protein for success, the use of truncation mutants in concert with structure-stabilizing binding partners, interactors, or agents can be employed in an additional embodiment.

As used herein, the phrase "crystallographic structure determination" refers to any method of obtaining the three-dimensional structure or model of a protein of interest through the use of protein crystallography. Methods of crystallographic structure determination, in particular X-ray diffraction crystallographic methods, are well known in the art, and frequently are provided at large shared facilities once crystals are obtained. The methods of the present invention provide a novel method of performing crystallographic structure determination through the use of hydrogen exchange analysis. Hydrogen exchange analysis can be integrated into any known or novel methods of crystallography available in the art.

Many proteins which appear well-structured overall, contain unstructured regions (see, e.g., Wright and Dyson, *J. Mol. Biol.* 293:321-331, 1999). While such regions may serve a function within the protein in some context, they can inhibit or prevent crystallization of the well-folded regions. This problem has been apparent for years, but its full extent is difficult to discern from the published literature. In some instances, proteins may crystallize with some floppy regions, either at their ends or within short internal stretches. In many other instances, it is not known why a particular protein does not crystallize, even with seemingly pure protein. Using the methods of the present invention, crystallographic structure determination is facilitated by the ability to rapidly and precisely define structured and unstructured regions of a target that could then be used to induce functionally relevant structure in such regions by systematic identification of structure-inducing agents for the protein of interest.

This capability to define structured and unstructured region of a protein of interest can enhance crystallographic structure determination through several mechanisms. It can increase the homogeneity of protein preparations. Moreover, unstructured regions of proteins are particularly susceptible to inadvertent degradation by contaminating cellular proteases in the course of purification and storage. The energetics and kinetics of protein crystallization are facilitated by selective deletion of unstructured sequences (see, e.g., Kwong et al., *J. Biol. Chem.* 274:4115-4123, 1999).

A number of approaches to obtain information defining structured and unstructured protein regions, ranging from stability-dependent protein expression screens, to computation of stability from primary structure have been reported and used, but each has requirements that limit utility (see, e.g., Dunker et al, *Pac. Symp. Biocomp.* 3:473-484, 1998; Garner et al., *Genome Inform.* 9:201-214, 1998; and Romero et al., *Pac. Symp. Biocomp.* 3:473-484, 1998). With NMR spectroscopy, protein quantity, concentration, time needed, and size are limiting. Limited proteolysis coupled to mass spectrometry is presently one of the preferred approaches to refining construct definition for conventional crystallographic efforts (see, e.g. Cohen et al., supra). As such, its use is time consuming, frequently requiring that multiple proteolytic reactions be refined for optimal cleavage. The interpretation of the results of limited proteolysis is confounded by the possibility that proteolysis may clip internal loops, leading to destabilization and subsequent further proteolytic degradation of what was actually a structured region.

Finally, there is no facile method to confirm that a binding partner for a protein, or other agent can both induce structure in unstructured regions of the target, and leave substantially unperturbed the existing structured regions of the target. When agents are allowed to act on target proteins, uncertainty remains concerning the degree to which they may undesirably perturb the structure of stable portions of the parent. Taken together, these several shortcomings have rendered the foregoing methods of admixing agents with a protein of interest of little utility in the context of large-scale crystal structure determination efforts, where throughput and cost are dominating considerations (see, e.g., Chen et al., *Prot. Sci.* 7:2623-2630, 1998).

The methods of the present invention allow for the measurement of peptide amide hydrogen exchange rates that can provide precisely the information needed for reliable expression construct design. The methods of the present invention comprise generating a hydrogen exchange stability map. The hydrogen exchange stability map shows unstructured regions of the protein and precisely shows the location of boundaries between structured and unstructured regions of the protein. This information provides the guide for agents that can act on the protein in a manner wherein all or part of at least one unstructured region of the protein is induced to become structured, as identified by a slowing of the very vast hydrogen exchange rates of the amides in that region of sequence. The protein, wherein all or part of at least one unstructured region of the protein becomes structured, along with the agent, are then subjected to co-crystallization procedures. Unstructured regions of a protein structure are known to inhibit the formation of crystals, and to inhibit the formation of crystals suitable for crystal structure determination.

Methods of the invention are also provided, wherein a hydrogen exchange stability map of a protein with and without the action of the agent, can be compared. This comparison serves to characterize the degree to which the agent acts on the protein in a manner that allows faithful retention of the stable or structured elements of the protein without agent.

As used herein, the phrase "hydrogen exchange analysis" refers to any method by which measurement of the exchange rates of a peptide amide hydrogen with an isotope of hydrogen (for example, deuterium or tritium), present in the environment surrounding the protein (whether in soluble or crystalline form), are used to gain insight to the structure or stability of a protein as a whole, or portions or regions thereof. For more than 40 years, peptide amide hydrogen-exchange techniques have been employed to study the thermodynamics of protein conformational change and to probe the mechanisms of protein folding (see, e.g., Englander and Englander, *Meth. Enzymol.* 232:26-42, 1994; and Bai et al., *Meth. Enzymol.* 259:344, 1995). More recently, they have proven to be increasingly powerful methods by which protein dynamics, domain structure, regional stability and function can be studied (see, e.g., Englander et al., *Prot. Sci.* 6:1101-1109, 1997). The principle of hydrogen-exchange reflects the fact that many hydrogens (commonly known as acidic hydrogens such as —OH, —NH$_2$, —SH, and peptide amide hydrogens) are not permanently attached to the protein, but continuously and reversibly interchange with hydrogen present in their external immediate environment. Most acidic hydrogen exchanges occur too rapidly to be experimentally useful. An important exception is the more slowly exchanging peptide amide hydrogen (main-chain amide hydrogen) present in every amino acid except proline, thereby providing a way of examining protein structure and stability.

By an "improved hydrogen exchange stability map" is meant that the hydrogen exchange stability map of the agent-modified form of the protein demonstrates a reduction in the unstructured portion of the protein. An "improved hydrogen exchange stability map" is predictive that the agent-modified form is (a) more likely to form crystals than the unmodified protein of interest, and/or (b) more likely to form crystals that are suitable for crystal structure determination than the unmodified protein of interest.

The hydrogen exchange reaction can be experimentally followed by using tritiated or deuterated solvent. The chemical mechanisms of the exchange reactions are understood, and several well-defined factors can profoundly alter exchange rates. One of these factors is the extent to which a particular exchangeable hydrogen is exposed or accessible to solvent. The exchange reaction proceeds efficiently only when a particular peptide amide hydrogen is fully exposed to solvent. In a completely unstructured polypeptide chain, all peptide amide hydrogens are maximally accessible to water and exchange at their maximal possible rate, which is approximately (within a factor of 30) the same for all amides; a half-life of exchange in the range of one second at 0° C. and pH 7.0. Exact exchange rates expected for particular amide hydrogens in fully unstructured segments can be reliably calculated from knowledge of the temperature, pH and the primary amino acid sequence involved (see, e.g., Molday et al., *Biochemistry* 11:150, 1972; and Bai et al., *Proteins: Str. Funct. Gen.* 17:74-86, 1993).

In a folded protein, most peptide amide hydrogens are slower (up to $10^9$ fold slower) than this maximal exchange rate, as they are not efficiently exposed to solvent. The ratio of exchange rates for a particular amide hydrogen, before and after protein folding, is referred to as the exchange protection factor, and directly reflects the free energy change in the atomic environment of that particular hydrogen upon folding. In this sense, amide hydrogens can be treated as atomic scale sensors of highly localized free energy change throughout a protein and the magnitude of free energy change reported from each of a protein's amide hydrogens in a folded versus unfolded state is precisely equal to -RT ln (protection factor) (Bai et al., supra). In effect, each peptide amide hydrogen's exchange rate in a folded protein directly and precisely reports the protein's thermodynamic stability at the individual amino acid scale. Ranking and comparison of the exchange rates of a protein's amide hydrogens therefore allows direct and unambiguous identification and localization of structured and unstructured regions of the protein. As used herein, unstructured regions of a protein are those where contiguous stretches of primary sequence exhibit fast exchange rates, indicative of complete and continuous solvation of the amide hydrogens in such segments. Further, as used herein, very unstructured regions refer to linear stretches of primary sequence in which the rates of exchange of each amide hydrogen in the segment is very fast, typically greater than about 90% of amide hydrogens are saturation-deuterated in about 10 seconds or less at 0° C. At least one unstructured region, or a portion thereof, is then targeted for deletion in accordance with the methods of the present invention.

Deuterium exchange methodologies coupled with liquid chromatography mass spectrometry (LCMS), developed over the past 10 years, presently provide the most effective approach to study proteins larger than 30 kDa in size (see, e.g., Engen and Smith, *Anal. Chem.* 73:256-65, 2001). Proteolytic and/or collision-induced dissociation (CID) fragmentation methods allow exchange behavior to be mapped to subregions of the protein (Engen and Smith, supra; Hoofnagle et al., *Proc. Natl. Acad. Sci.* USA 98:956-961, 2001; Resing et al., *L. Am. Soc. Mass Spectrom.* 10:685-702, 1999; and Mandel et al., *Anal. Chem.* 70:3987-3995, 1998).

DXMS Methodology

Figure 1:
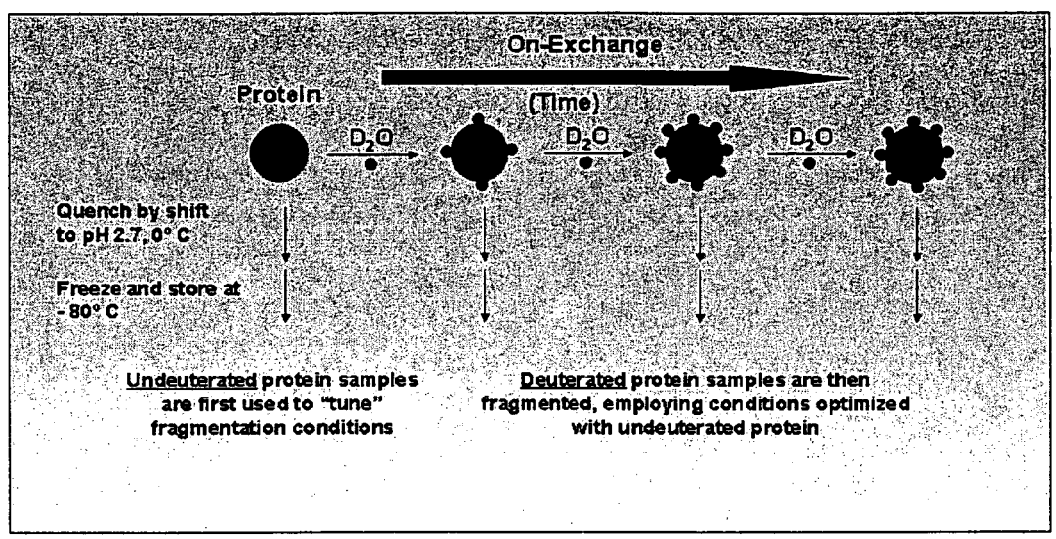
FIG. 1 illustrates the process of time-dependent functional deuteration of proteins for hydrogen exchange analysis.

Reviews of the methodology and its recent applications can be found in three articles (Woods-Jr., et al. Journal of Cellular Biochemistry 37:89-98 2001, Hamuro, et al. J. Mol. Biol. 4:703-714 2002, Wong, et al. Protein Science 11:73 2002). Detailed descriptions of some of the methodological enhancements that constitute DXMS are presented in published literature and U.S. patents (Woods-Jr. U.S. Pat. No. 5,658,739. 1997, Woods-Jr. U.S. Pat. No. 6,291,189 2001, Woods-Jr., U.S. Pat. No. 6,331,400 2001). The technique has an initial exchange-dependent labeling step performed under entirely physiologic conditions of pH, ionic strength, and buffer salts (see FIG. 1); and a subsequent localization step (see FIG. 2). The labeling is performed by simply adding deuterated water to a solution of the protein. During this on-exchange incubation, deuterium exchanges onto the several amides of the protein. As labeling progresses, aliquots are exchange-"quenched" by shifting the protein to conditions (low pH, and temperature) that dramatically slow the rate of exchange, effectively locking in place the attached deuterium. Undesired "back-exchange", or loss of label after establishment of sample quench, can be essentially halted by holding samples at very low temperatures (−80° C.) until they are melted (at 0° C.) and further processed as below. This process has been automated with the development of a cryogenic autosampler within the DXMS apparatus (Woods-Jr., et al. Journal of Cellular Biochemistry 37:89-98 2001, Hamuro, et al. J. Mol. Biol. 4:703-714 2002, Wong, et al. Protein Science 11:73 2002, Woods-Jr. U.S. Pat. No. 5,658, 739. 1997, Woods-Jr. U.S. Pat. No. 6,291,189 200 1 Woods-Jr. U.S. Pat. No. 6,331,400 2001) (see FIG. 2).

Figure 2:
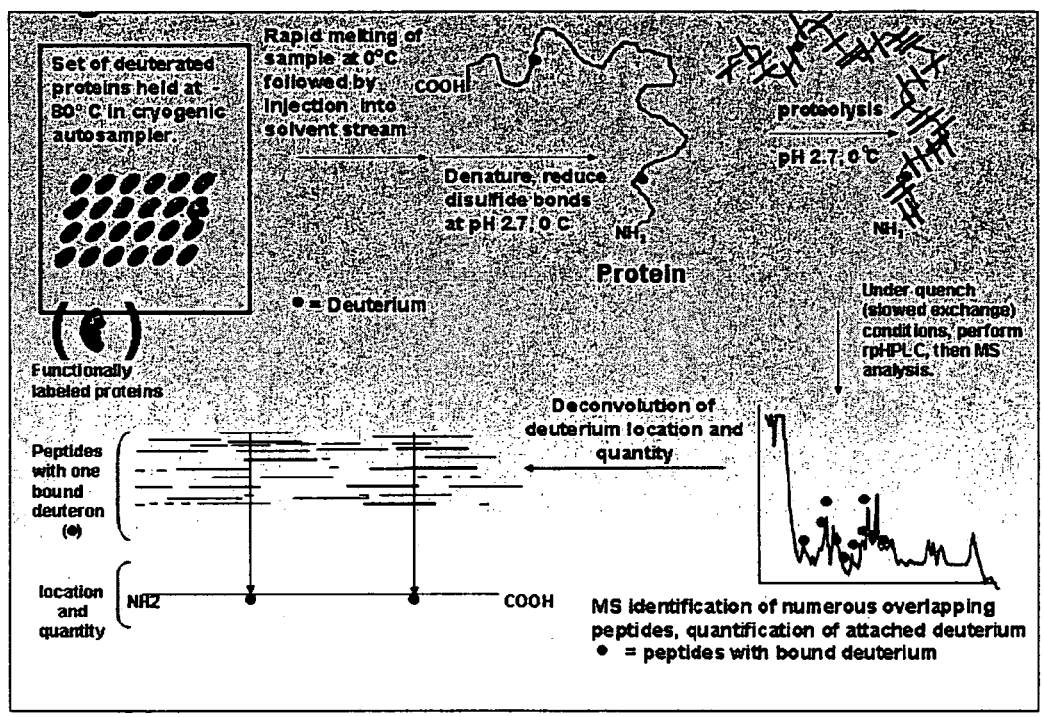
FIG. 2 illustrates an exemplary method employed in DXMS to quantify deuterium content and location within functionally deuterated proteins prepared as in FIG. 1.

In the second step, the amino acid sequence location and amount of attached deuterium is determined (see FIG. 2). Under "quench" conditions, the protein sample is (automatically) first optionally denatured, optionally disulfide-reduced, and then proteolyzed by solid-phase pepsin into overlapping fragments of ~3-15 amino acids in size. It is to be emphasized that this is high-throughput, exhaustive (not limited) proteolysis, with typical digestion times being of the order of 20 seconds. The digests are then subjected to rapid high performance liquid chromatography (HPLC) separation (5-10 minute gradients), and directly analyzed by electrospray-ion trap or time of flight (TOF) mass spectrometry performed under conditions adapted to amide hydrogen exchange studies.

The extent of pepsin digestion is finely tuned with the goal of generating multiple overlapping fragments of the protein. When desired, even finer fragmentation is achieved with additional acid-reactive proteinases. These proteases have little sequence specificity, and the pattern and extent of digestion depends primarily on the denaturation state of the substrate. By tuning of the extent and mode of denaturation, fragmentation patterns are modulated at will with each pattern being extremely reproducible as long as conditions are held constant. Fragmentation is followed by rapid sequence-identification, performed first with undeuterated protein under quench conditions, followed by assessment of deuterium label bound to each fragment generated from deuterated protein samples. The differences in deuterium content between peptides with overlapping sequences is used to further sub-localize and quantify attached deuterium label. Rapid determination of the sequences of the large number of fragments generated is accomplished by analysis of MS:MS data employing specialized software developed over the past two years (Woods-Jr., et al. Journal of Cellular Biochemistry 37:89-98 2001, Hamuro, et al. J. Mol. Biol. 4:703-714 2002, Wong, et al. Protein Science 11:73 2002).

The methods, automation, and software that constitute the invention DXMS method and apparatus are described in detail in the above citations. Integrated automation of fluidics, including sample preparation (functional deuteration), sample storage and injection (cryogenic autosampler), solid-state proteolysis, liquid chromatography, and mass spectrometry allows rapid, continuous data acquisition, typically with one sample processed every 20 minutes. With these enhancements, a high resolution, comprehensive DXMS analysis of a protein is completed in two weeks, and can so process 5 proteins simultaneously. Studies that are targeted to the definition of structured vs. unstructured regions of proteins can be accomplished at a much faster pace, as demonstrated herein.

MS scans containing the numerous peptides of interest are individually isolated from the mass-intensity lists, processed to optimize signal-to-noise ratios, and then the geometric centroids of the isotopic envelopes of each peptide determined and recorded. Calculation of the difference in weight between the measured centroid of the deuterated peptide and the centroid for the same peptide without deuterium allows determination of the amount of deuterium on each peptide at the time of MS measurement. These data manipulations are now automatically performed by specialized data reduction software that allows efficiently processing of the tremendous amount of data obtained through automated DXMS data acquisition in a matter of hours, greatly speeding both fragmentation optimization and calculation of peptide deuterium content (Woods-Jr., et al. Journal of Cellular Biochemistry 37:89-98 2001, Hamuro, et al. J. Mol. Biol. 4:703-714 2002, Wong, et al. Protein Science 11:73 2002).

Figure 9:
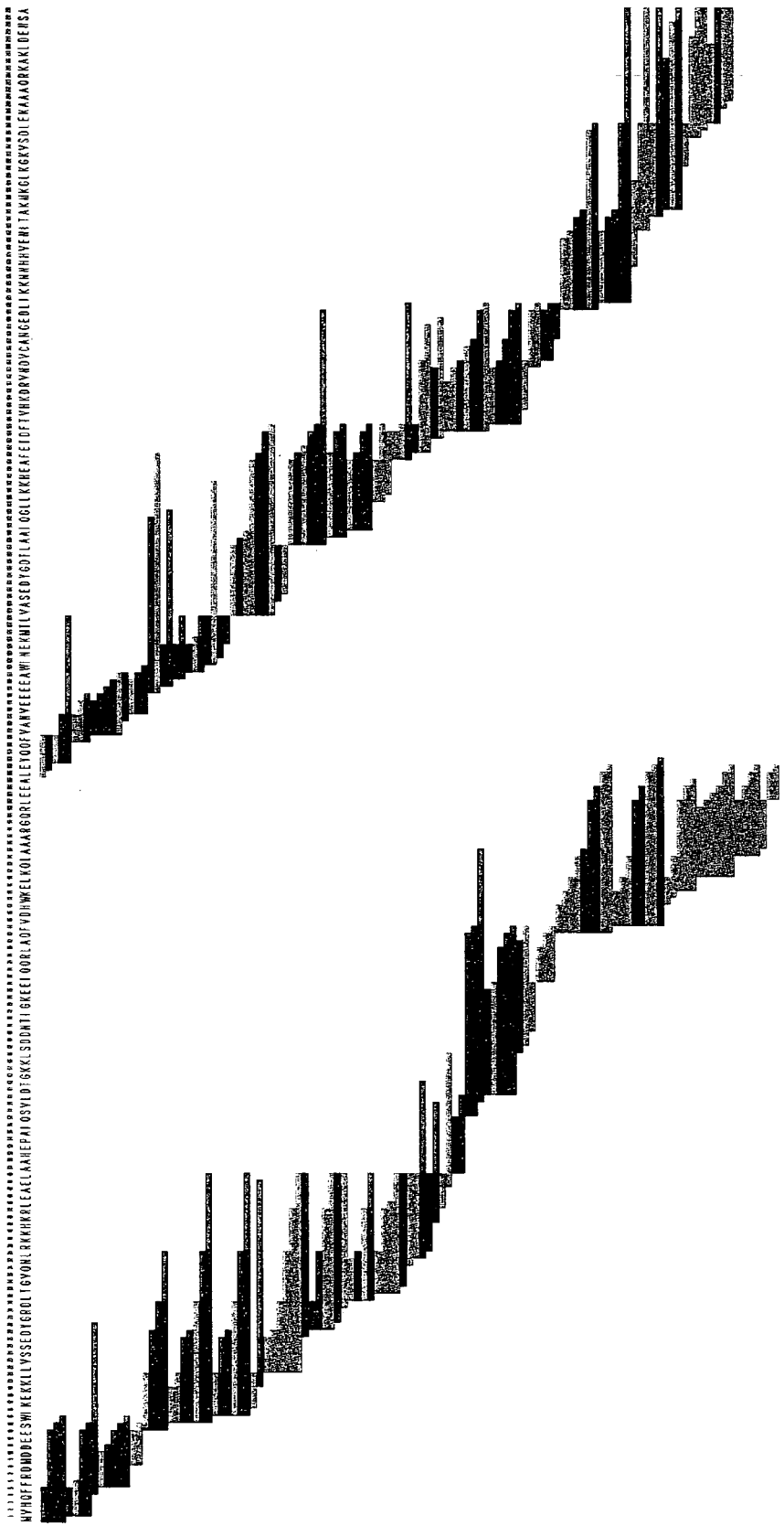
FIG. 9 illustrates a spectrin construct R1617 peptide map (SEQ. ID. No. 22) resulting from combined pepsin plus fungal protease XIII.

A typical example high-density fragmentation data obtained by invention methods, and how it can be processed to produce a stability map is shown in FIG. 9 and 11A for data from a two tandem repeat construct of chicken brain at spectrin ($16^{th}$-$17^{th}$ repeats). The (crystal) structure of this construct had been previously determined to be a coiled coil with five very long alpha helices linked by four short loops (Grum, et al. Cell 98:523-535 1999). Spectrin was first subjected to denaturation in varying concentrations of guanidine hydrochloride (GuHCl; 0, 0.05, 0.5, 4.0 M) under quench conditions (0° C., pH 2.7,) followed by digestion with solid-state pepsin for 30 seconds. It was found that 0.5M GuHCl produced sufficient fragmentation for the initial study, and the resulting fragmentation map, consisting of 108 overlapping peptides is shown in FIG. 11A. Spectrin was then on-exchanged in deuterated buffer for varying times at (10 seconds to 24 hours) at 22° C., samples then exchange-quenched, fragmented with pepsin, fragments identified, and deuterium on each peptide, at each exchange time point quantified by the forgoing DXMS methodologies.

The usual way to analyze such data is to evaluate the deuteration behavior of a minimal set of peptides that spans the protein's sequence (Engen, et al. Analytical Chemistry 73:256A-265A 2001, Hoofnagle, et al. Proceedings, National Academy of Sciences 98:956-961 2001, Zhang, et al. Protein Sci 10:2336-45. 2001, Kim, et al. Protein Sci 11:1320-9. 2002, Peterson, et al. Biochem J 362:173-81. 2002, Woods-Jr., et al. Journal of Cellular Biochemistry 37:89-98 2001, Hamuro, et al. J. Mol. Biol. 4:703-714 2002, Wong, et al. Protein Science 11:73 2002). Given the large number of overlapping peptides that invention enhanced methods produce, this means throwing away 80-90% of currently available data. To improve on this, a "manual" deconvolution of the data was performed for the 108 peptides as follows: Plots of deuterium buildup vs. time were automatically constructed for each peptide and the number of amides exchanging in arbitrary fast, medium and slow rate classes (the latter class grouped with the very slow class unmeasured in the limited on-exchange times ($<10^5$ sec) used in this experiment; italics) determined for each peptide (see FIG. 10) where this classification into three rate classes is shown for three of the 108 spectrin peptides studied). A consensus map of rates vs. sequence was constructed from this information, employing a strategy in which peptides containing a single rate class were first placed in amino acid sequence register, followed by placement of more complex peptides in a manner that required that they conform with the preceding placements. The resulting deconvolution is shown in FIG. 11C, with the Consensus Rate Map indicated by the arrow. This analysis demonstrated features that were consistent with the protein's known crystallographic structure: the locations of the loop regions between the long alpha helices were uniformly fast-exchanging (FIG. 11C, short bars below the consensus rate map).

Computational methods for deconvolution of this aggregate deuterated fragment data into amide-specific rates have also been devised. Invention methods provide the ability to increase the degree of protein fragmentation, and therefore the resolution of a particular study, almost at will. FIG. 11D shows the fragmentation pattern obtained when Spectrin was fragmented with the combination of pepsin and Fungal protease XIII (an additional 62 fragments, shown). For a further discussion of these deconvolution methods, see Example 2 below.

DXMS Analysis of *Thermotoga* Proteins

A detailed DXMS analysis of twenty-four different *Thermotoga maritima* proteins under crystallographic study was performed, with study proteins being those that had failed prior crystallization efforts, as well as well-crystallizing controls. Six of them had crystallized well and had solved structures, while the majority had failed to crystallize sufficiently well for crystallographic study. pH "quenched" samples of the proteins were batch-processed in a single 48 hour automated DXMS run to acquire data for fragmentation map generation (1.0 M GuHCl, 30 seconds pepsin digestion used). DXMS Software was then used over four days to identify peptide fragments for each protein and generate fragmentation maps. Good to excellent fragmentation maps were generated for all but three of the proteins using the single denaturation condition employed in this experiment.

These twenty-one proteins were then on-exchanged in deuterated buffer for 10 seconds at pH 7.0. on ice, quenched with 0.5% formic acid containing 1.0 M GuHCl, and then snap-frozen on dry ice, and stored at −80 degrees C. until automated DXMS analysis. Data on the deuterated sample set was acquired in a single automated 30 hour run, and subsequent data reduction performed over one week on the DXMS software. The total time elapsed for data acquisition and analysis was two weeks, and a total of 100 micrograms of each protein was used to complete the study.

Figure 5:
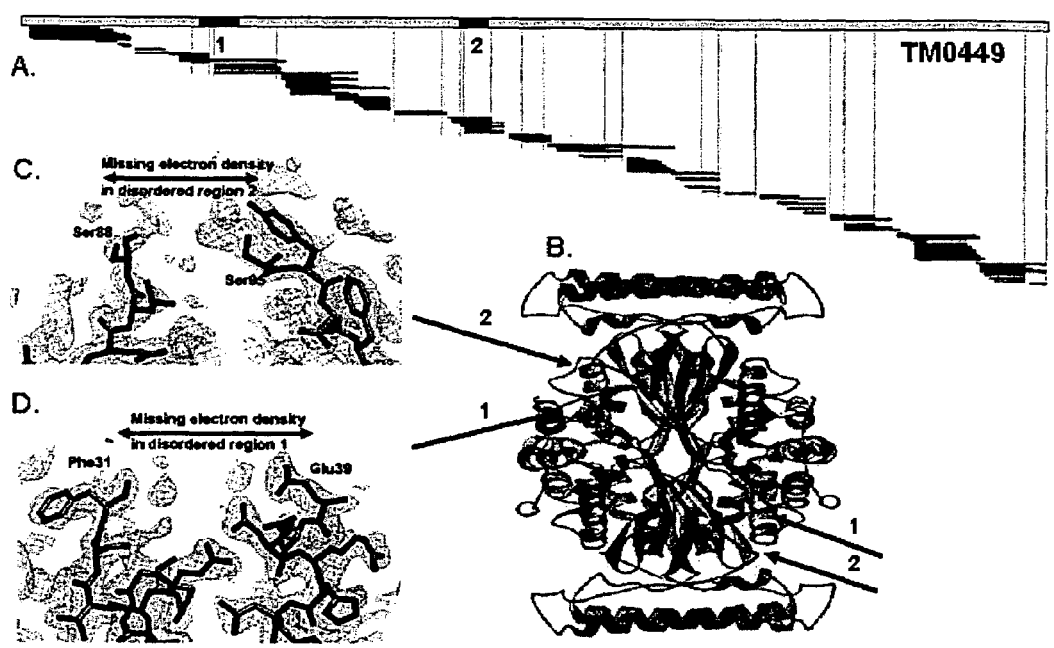
FIG. 5 collectively illustrates TM0449 structure determination.

FIG. 5 presents the rate map for the protein TM0449. The horizontal bars are the protein's pepsin-generated fragments that had been produced, identified, and used as exchange rate probes in this DXMS study. The number of deuterons that went on to each peptide in 10 seconds is indicated by the number of red residues in each peptide. This duration of labeling was calculated to be just sufficient to selectively deuterate only freely solvated amides (Molday, et al. Biochemistry 11:150 1972, Bai, et al. Proteins: Structure, Function, and Genetics 17:74-86 1993). This was evaluated by first pepsin-fragmenting a reference protein (to "un-structure" it), and then labeling the peptide mix for 10 seconds at pH 7.0, 0 degrees C. as above. All peptides saturation-labeled under these conditions. The localization of label within the entire sequence of the protein was performed by consensus deconvolution as in FIG. 11C, with confidence limits indicated in FIG. 5 by the vertical bars. The consensus rate map is presented at the top of FIG. 5, with very rapidly exchanging residues, superimposed on the protein's primary sequence. Rate maps like this were prepared for each of the proteins and data analyzed.

Figure 4:
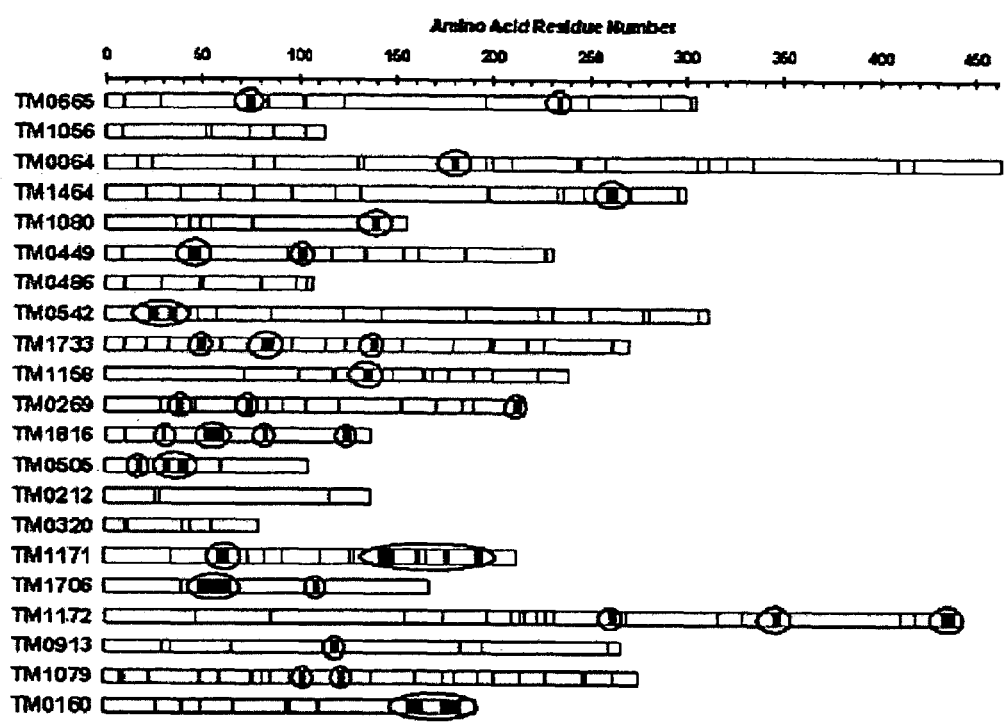
FIG. 4 illustrates a summary of the 10-second deuteration results are shown for 21 *Thermotoga maritima* proteins that were analyzed, whose amino acid lengths varied from 76 to 461 residues. Dark regions indicated fast exchanging amides and clear regions indicate stretches of no exchange. Regions of four or more fast exchanging amides are circled.

FIG. 4 presents the identities and TIGR description of the 24 *Thermotoga* proteins (nearest homolog) studied. There were four groups of proteins, with six representatives for each group: proteins that had not crystallized at all; those that gave few crystals; others that had crystallized but diffracted poorly, and those that diffracted well and had a solved structure. The proteins had also been put down for repeat array crystallization efforts contemporaneously with DXMS analysis: day 7 readings of crystallization success (and the later 1 month results) confirmed the original classification for all proteins. The three proteins that had given poor DXMS fragmentation results under the single fragmentation condition used, and not further studied in this experiment, were TM0855, TM1773, and TM1764.

Interpretation of the DXMS exchange maps was guided by the expectation of predominantly two patterns of fast exchange labeling: structurally stable, but well solvated, rapidly exchanging residues (one to three contiguous residues) vs. labeling of longer stretches of sequence (four or more residues) indicative of disorder. This dichotomy presumed that three contiguous amino acids was likely the largest number needed to complete a surface-turn in a structurally stable region of a protein. In FIGS. 5-11, the percent of each protein's residues that rapidly labeled in stretches of four or more residues is indicated (%).

FIG. 5 also shows results for TM0449, a protein that had crystallized and diffracted well, and for which the structure had been solved. Its rate map demonstrates two long segments with rapid exchange (>4 residues in each, (labeled A and B) and several isolated rapid exchangers in groups of 3 or less, scattered throughout the sequence. When compared to the (previously) solved structure for this protein, both segments A and B corresponded to regions of crystallographically determined disorder in the TM0449 crystal, confirming the ability of DXMS data to detect and localize such disordered regions.

FIG. 6 presents the DXMS rate map for TM0505, which demonstrated rapid exchange in three segments containing four or more residues, constituting 16% of its sequence. While this protein had produced very poorly diffracting crystals, it is a very close primary sequence homolog of the GroES heat shock protein of *M. tuberculosis*, for which a crystal structure had been previously obtained, both as the isolated protein (see FIG. 6B) and as the GroELS complex with the GroEL subunit (FIG. 6A). The GroEL-binding surface of the GroES subunit exhibits marked conformational change upon binding (see FIG. 7). When the *T. maritima* residues with rapid exchange in four or more contiguous residues were decorated upon the *M. tuberculosis* structures, they localized to a remarkable degree to the residues that make contacts with the GroEL binding surface. This result indicates that these residues are highly disordered in solution when not complexed to GroES, but become structured upon binding to form the GroELS complex. This is a demonstration of the ability of DXMS-determined exchange rate analysis to identify disordered regions that form structure in the context of a stabilizing binding partner.

Invention methods demonstrate that large, rapidly exchanging regions of protein kinase A (PKA) regulatory subunits dramatically slow their rates of exchange when they bind to either anchoring proteins (DAKAP2) or PKA catalytic subunits, and this has been interpreted as evidence for quaternary contact-mediated structure stabilization. Several years ago, attempts to crystallize the full length RIα regulatory subunit had repeatedly failed until, by chance, deletion constructs were prepared that were devoid of large segments (the N-terminal 19 aa and an internal 30 aa segment, 80-110), and crystallized well. Recent DXMS studies of RIα directly indicate that these entire segments exchange very rapidly, being fully deuterated at the earliest on-exchange time measured. Furthermore, these are the same rapidly exchanging regions of RIα that dramatically slow in exchange when complexed with the PKA catalytic subunit. It is expected that a similar phenomenon is occurring in the formation of the GroELS complex. Taken together these results indicate that, if appropriately employed, DXMS may be able to guide the identification of structure-inducing binding partners for particular failed crystallographic target proteins that contain substantial amounts binding surface disposed unstructured sequence.

In Table 1, the crystallization success and other attributes of the studied *Thermotoga* proteins are presented, along with the DXMS-deduced features discussed above, most particularly, the percent of each protein's sequence that rapidly exchanges in stretches of four or more residues in length, and the detailed maps of proteins with DXMS-determined disorder presented in FIG. 4.

Invention methods using these *Thermotoga* constructs has established that: (i) DXMS can reliably detect and localize disordered sequence within overall well-structured proteins; (ii) invention DXMS data acquisition apparatus and data reduction software are both capable of performing at the speed and resolution needed; and (iii) DXMS is able to guide the identification of structure-inducing binding partners for particular failed crystallographic target proteins that contain substantial amounts binding surface disposed unstructured sequence, and then subjecting the pair to co-crystallization efforts.

The instant invention is outlined in FIG. 3, path 3. Initial studies (DXMS # 1, FIG. 3) to define very rapidly exchanging stretches of sequence that are four or more residues in length were performed, and then a repeat hydrogen exchange analysis (DXMS # 2, FIG. 3, path 3) of protein-interactor pairs performed with a panel of protein interactors identified in yeast two-hybrid screens was performed, to identify particular interactors that induce slowing of very fast exchanging segments in the protein, indicating that the interactor is inducing structure within the previously disordered regions in the protein. If the protein has extensive disordered sequence primarily on the ends, then the strategy of truncating disordered ends is likely preferred (path 1). If disorder is primarily internal, then the preferred approach may be to separately express the structured domains (path 2). DXMS-determined protein stability maps are useful in (i) identifying proteins that may contain such regions; (ii) designing appropriate "baits" for interactor selection in 2-hybrid studies they should contain the DXMS-identified unstructured regions of the protein- and 3. Screening for particular protein-interactor pairs that show evidence of induced structure in the originally disordered regions of the protein.

For details of the methods that were employed to produce proteins please see (Santarsiero, et al. J. Appl. Cryst. 35:1-4 2002, Stevens Structure 8:R177-R185 2000, Stevens Current opinion in Structural Biology 10:558-563 2000, Goodwill, et al. DTT 6:S113-S118 2001). In brief, all targets are PCR amplified based on the expression construct of interest into the pBAD Invitrogen expression system using the arabinose promoter. The first 6 amino acids of thioredoxin and 6 His residues are placed at the N-terminus to get maximum expression in Invitrogen's "genehog" expression strain, and to allow for rapid affinity purification on immobilized nickel chromatography resin. The 96 well fermentor developed at GNF will be employed, to express 70 ml of culture grown to an OD of 20-30, and subsequently purified using a BIOCAD chromatography system (Applied Biosystems) utilizing POROS MC chromatography resin for the first column. Purified samples will be eluted with 400 mM imidizole and desalted on a Sepharose G-25 column into 10 mM Tris HCl with 150 mM NaCl and purity is then assessed by SDS-PAGE. Those with sufficient purity are concentrated in Millipore spin concentrators to a final volume of 0.75 ml.

The milligram quantities of each daughter protein that were produced were sufficient for both subsequent DXMS analysis (a few hundred micrograms) and robotic nanocrystallization efforts on selected (structurally faithful) daughter proteins.

Nanoliter-volume robotic crystallization system (Agincourt) was performed and diffracton data acquired as previously described (Santarsiero, et al. J. Appl. Cryst. 35:1-4 2002, Stevens Current opinion in Structural Biology 10:558-563 2000, Goodwill, et al. DTT 6:S113-S118 2001).

In order to proceed with crystallizing a protein of interest, a substantially pure protein preparation is usually first made. The following terms are defined in order to facilitate the discussion of protein preparation, modification, and crystallization.

As used herein, "naturally occurring amino acid" and "naturally occurring R-group" includes L-isomers of the twenty amino acids naturally occurring in proteins. Naturally occurring amino acids are glycine, alanine, valine, leucine, isoleucine, serine, methionine, threonine, phenylalanine, tyrosine, tryptophan, cysteine, proline, histidine, aspartic acid, asparagine, glutamic acid, glutamine, arginine, and lysine. Unless specially indicated, all amino acids referred to in this application are in the L-form.

"Unnatural amino acid" and "unnatural R-group" includes amino acids that are not naturally found in proteins. Examples of unnatural amino acids included herein are racemic mixtures of selenocysteine and selenomethionine. In addition, unnatural amino acids include the D or L forms of, for example, nor-leucine, para-nitrophenylalanine, homophenylalanine, para-fluorophenylalanine, 3-amino-2-benzylpropionic acid, homoarginines, D-phenylalanine, and the like.

"R-group" refers to the substituent attached to the α-carbon of an amino acid residue. An R-group is an important determinant of the overall chemical character of an amino acid. There are nineteen natural R-groups found in proteins, which make up the twenty naturally occurring amino acids.

One of the twenty naturally occurring amino acids, glycine, is alpha unsubstituted and achiral. "α-carbon" refers to the chiral carbon atom found in an amino acid residue. Typically, four different substituents will be covalently bound to said α-carbon including an amine group, a carboxylic acid group, a hydrogen atom, and an R-group.

"Positively charged amino acid" and "positively charged R-group" includes any naturally occurring or unnatural amino acid having a positively charged side chain under normal physiological conditions. Examples of positively charged, naturally occurring amino acids include arginine, lysine, histidine, and the like.

"Negatively charged amino acid" and "negatively charged R-group" includes any naturally occurring or unnatural amino acid having a negatively charged side chain under normal physiological conditions. Examples of negatively charged, naturally occurring amino acids include aspartic acid, glutamic acid, and the like.

"Hydrophobic amino acid" and "hydrophobic R-group" includes any naturally occurring or unnatural amino acid having an uncharged, nonpolar side chain that is relatively insoluble in water. Examples of naturally occurring hydrophobic amino acids are alanine, leucine, isoleucine, valine, proline, phenylalanine, tryptophan, methionine, and the like.

"Hydrophilic amino acid" and "hydrophilic R-group" includes any naturally occurring or unnatural amino acid having a charged polar side chain that is relatively soluble in water. Examples of naturally occurring hydrophilic amino acids include serine, threonine, tyrosine, asparagine, glutamine, cysteine, and the like.

In designing the nucleic acid sequences to encode a protein of interest, it may be desirable to reengineer the gene for improved expression in a particular expression system. For example, it has been shown that many bacterially derived genes do not express well in plant systems. In some cases, plant-derived genes do not express well in bacteria. This phenomenon may be due to the non-optimal G+C content and/or A+T content of said gene relative to the expression system being used. For example, the very low G+C content of many bacterial genes results in the generation of sequences mimicking or duplicating plant gene control sequences that are highly A+T rich. The presence of A+T rich sequences within the genes introduced into plants (e.g., TATA box regions normally found in promoters) may result in aberrant transcription of the gene(s). In addition, the presence of other regulatory sequences residing in the transcribed mRNA (e.g. polyadenylation signal sequences (AAUAAA) or sequences complementary to small nuclear RNAs involved in pre-mRNA splicing) may lead to RNA instability. Therefore, one goal in the design of genes is to generate nucleic acid sequences that have a G+C content that affords mRNA stability and translation accuracy for a particular expression system.

Due to the plasticity afforded by the redundancy of the genetic code (i.e., some amino acids are specified by more than one codon), evolution of the genomes of different organisms or classes of organisms has resulted in differential usage of redundant codons. This "codon bias" is reflected in the mean base composition of protein coding regions. For example, organisms with relatively low G+C contents utilize codons having A or T in the third position of redundant codons, whereas those having higher G+C contents utilize codons having G or C in the third position. Therefore, in reengineering genes for expression, one may wish to determine the codon bias of the organism in which the gene is to be expressed. Looking at the usage of the codons as determined for genes of a particular organism deposited in GenBank can provide this information. After determining the bias thereof, the new gene sequence can be analyzed for restriction enzyme sites as well as other sites that could affect transcription such as exon:intron junctions, polyA addition signals, or RNA polymerase termination signals.

Genes encoding the protein of interest can be placed in an appropriate vector and can be expressed using a suitable expression system. An expression vector, as is well known in the art, typically includes elements that permit replication of said vector within the host cell and may contain one or more phenotypic markers for selection of cells containing the gene. The expression vector will typically contain sequences that control expression such as promoter sequences, ribosome binding sites, and translational initiation and termination sequences. Expression vectors may also contain elements such as subgenomic promoters, a repressor gene or various activator genes. The artisan may also choose to include nucleic acid sequences that result in secretion of the gene product, movement of said product to a particular organelle such as a plant plastid (see U.S. Pat. Nos. 4,762, 785; 5,451,513 and 5,545,817, which are each incorporated herein by reference in their entirety) or other sequences that increase the ease of peptide purification, such as an affinity tag.

A wide variety of expression control sequences are useful in expressing agents for use with the protein of interest when operably linked thereto. Such expression control sequences include, for example, the early and late promoters of SV40 for animal cells, the lac system, the trp system, major operator and promoter systems of phage S, and the control regions of coat proteins, particularly those from RNA viruses in plants. In E. coli, a useful transcriptional control sequence is the T7 RNA polymerase binding promoter, which can be incorporated into a pET vector as described by Studier et al., Methods Enzymology 185:60-89, 1990.

For expression, a desired gene should be operably linked to the expression control sequence and maintain the appropriate reading frame to permit production of the desired protein or agent-modified form thereof. Any of a wide variety of well-known expression vectors are of use in the methods of the present invention. These include, for example, vectors comprising segments of chromosomal, non-chromosomal and synthetic DNA sequences such as those derived from SV40, bacterial plasmids including those from E. coli such as col E1, pCR1, pBR322 and derivatives thereof, pMB9, wider host range plasmids such as RP4, phage DNA such as phage S, NM989, M13, and other such systems as described by Sambrook et al., (Molecular Cloning, A Laboratory Manual, $2^{nd}$ Ed. (1989) Cold Spring Harbor Laboratory Press), which is incorporated by reference herein.

A wide variety of host cells are available for expressing agents useful in present invention. Such host cells include, for example, bacteria such as E. coli, Bacillus and Streptomyces, fungi, yeast, animal cells, plant cells, insect cells, and the like.

"Purified" or "isolated" refers to a protein or nucleic acid that has been separated from its natural environment. Contaminant components of its natural environment may include enzymes, hormones, and other proteinaceous or non-proteinaceous solutes. In one embodiment, the isolated molecule, in the case of a protein, will be purified to a degree sufficient to obtain at least 15 residues of N-terminal or internal amino acid sequence or to homogeneity by SDS-PAGE under reducing or non-reducing conditions using Coomassie blue or silver stain. In the case of a nucleic acid the isolated molecule will preferably be purified to a degree sufficient to obtain a nucleic acid sequence using standard sequencing methods.

By a "substantially pure polypeptide" or "substantially pure protein" is meant a polypeptide or protein which has been separated from components which naturally accompany it. Typically, the polypeptide is substantially pure when it is at least 60%, by weight, free from the proteins and naturally-occurring organic molecules with which it is naturally associated. Preferably, the preparation is at least 75%, more preferably at least 90%, and most preferably at least 99%, by weight, polypeptide. A substantially pure protein or polypeptide may be obtained, for example, by extraction from a natural source; by expression of a recombinant nucleic acid encoding a polypeptide; or by chemically synthesizing the protein. Purity can be measured by any appropriate method (e.g., column chromatography, polyacrylamide gel electrophoresis, or by HPLC analysis).

"Degenerate variations thereof" refers to changing a gene sequence using the degenerate nature of the genetic code to encode proteins having the same amino acid sequence yet having a different gene sequence. Degenerate gene variations thereof can be made encoding the same protein due to the plasticity of the genetic code, as described herein.

"Expression" refers to transcription of a gene or nucleic acid sequence, stable accumulation of nucleic acid, and the translation of that nucleic acid to a polypeptide sequence.

Expression of genes also involves transcription of the gene to make RNA, processing of RNA into mRNA in eukaryotic systems, and translation of mRNA into proteins. It is not necessary for the genes to integrate into the genome of a cell in order to achieve expression. This definition in no way limits expression to a particular system or to being confined to cells or a particular cell type and is meant to include cellular, transient, in vitro, in vivo, and viral expression systems in both prokaryotic, eukaryotic cells, and the like.

"Foreign" or "heterologous" genes refers to a gene encoding a protein whose exact amino acid sequence is not normally found in the host cell.

"Promoter" and "promoter regulatory element", and the like, refers to a nucleotide sequence element within a nucleic acid fragment or gene that controls the expression of that gene. These can also include expression control sequences. Promoter regulatory elements, and the like, from a variety of sources can be used efficiently to promote gene expression. Promoter regulatory elements are meant to include constitutive, tissue-specific, developmental-specific, inducible, subgenomic promoters, and the like. Promoter regulatory elements may also include certain enhancer elements or silencing elements that improve or regulate transcriptional efficiency. Promoter regulatory elements are recognized by RNA polymerases, promote the binding thereof, and facilitate RNA transcription.

Once a substantially pure protein of interest is prepared, it is subjected to crystallization to obtain the protein in crystalline form, of sufficient quality to determine the three-dimensional structure of the protein by X-ray diffraction methods. X-ray crystallography is a method of solving the three-dimensional structures of molecules. The structure of a molecule is calculated from X-ray diffraction patterns using a crystal of the protein studied as a diffraction grating. Three-dimensional structures of protein molecules arise from crystals grown from a concentrated solution of that protein. The process of X-ray crystallography can include the following steps: (a) preparing and isolating a polypeptide; (b) growing a crystal from a solution comprising the polypeptide with or without a compound, substrate, substrate mimic, modulator, ligand, or ligand analog; and(c) collecting X-ray diffraction patterns from the crystal(s), determining unit cell dimensions and symmetry, determining electron density, fitting the amino acid sequence of the polypeptide to the electron density, and refining the structure.

The term "crystalline form" refers to a crystal formed from a solution comprising a purified polypeptide corresponding to all or part of a protein of interest. In preferred embodiments, a crystalline form may also be formed from a purified polypeptide corresponding to all or part of a protein of interest in a complex with one or more additional molecules selected from the group consisting of substrates, products, substrate mimics, and inhibitors of the protein.

The present invention allows for the characterization of proteins and agent-modified forms thereof by crystallization followed by X-ray diffraction. Polypeptide crystallization occurs in solutions where the polypeptide concentration exceeds its solubility maximum (i.e., the polypeptide solution is supersaturated). Such solutions may be restored to equilibrium by reducing the polypeptide concentration, preferably through precipitation of the polypeptide crystals. Often polypeptides may be induced to crystallize from supersaturated solutions by adding agents that alter the polypeptide surface charges or perturb the interaction between the polypeptide and bulk water to promote associations that lead to crystallization.

Compounds known as "precipitants" are often used to decrease the solubility of the polypeptide in a concentrated solution by forming an energetically unfavorable precipitating layer around the polypeptide molecules (Weber, *Adv. Prot. Chem.* 41:1-36, 1991). In addition to precipitants, other materials are sometimes added to the polypeptide crystallization solution. These include buffers to adjust the pH of the solution and salts to reduce the solubility of the polypeptide. Various precipitants are known in the art and include the following: ethanol, 3-ethyl-2,4-pentanediol, many of the polyglycols (such as polyethylene glycol), and the like.

Commonly used polypeptide crystallization methods include the following techniques: batch, hanging drop, seed initiation, dialysis, and the like. In each of these methods, it is important to promote continued crystallization after nucleation by maintaining a supersaturated solution. In the batch method, polypeptide is mixed with precipitants to achieve supersaturation, the vessel is sealed, and set aside until crystals appear. In the dialysis method, polypeptide is retained in a sealed dialysis membrane that is placed into a solution containing precipitant. Equilibration across the membrane increases the polypeptide and precipitant concentrations thereby causing the polypeptide to reach supersaturation levels.

In the preferred hanging drop technique (McPherson, *J. Biol. Chem.* 6300-6306, 1976), an initial polypeptide mixture is created by adding a precipitant to a concentrated polypeptide solution. The concentrations of the polypeptide and precipitants are such that in this initial form, the polypeptide does not crystallize. A small drop of this mixture is placed on a glass slide that is inverted and suspended over a reservoir of a second solution. The system is then sealed. Typically, the second solution contains a higher concentration of precipitant or other dehydrating agent. The difference in the precipitant concentrations causes the protein solution to have a higher vapor pressure than the second solution. Since the system containing the two solutions is sealed, an equilibrium is established, and water from the polypeptide mixture transfers to the second solution. This equilibrium increases the polypeptide and precipitant concentration in the polypeptide solution. At the critical concentration of polypeptide and precipitant, a crystal of the polypeptide will form.

Another method of crystallization involves introducing a nucleation site into a concentrated polypeptide solution. Generally, a concentrated polypeptide solution is prepared and a seed crystal of the polypeptide is introduced into this solution. If the concentration of the polypeptide and any precipitants are correct, the seed crystal will provide a nucleation site around which a larger crystal forms. In typical embodiments, the crystals of the present invention are formed in hanging drops with 15% PEG 8000; 200 mM magnesium acetate or magnesium chloride, 100 mM 3-(N-morpholino)-2-hydroxypropanesulfonic acid (pH 7.0), and 1 mM dithiothreitol as precipitant.

Once crystals are obtained from the protein of interest and/or agent- agent-modified forms thereof, the crystals are subjected to crystallographic structure determination utilizing X-ray diffraction techniques as are known in the art. Diffraction patterns are used to determine the atomic or structure coordinates that define the three-dimensional structure of a protein molecule.

"Structure coordinates" refers to Cartesian coordinates (x, y, and z positions) derived from mathematical equations involving Fourier synthesis as determined from patterns obtained via diffraction of a monochromatic beam of X-rays by the atoms (scattering centers) of a polypeptide in crystal form. Diffraction data are used to calculate electron density maps of repeating protein units in the crystal (unit cell). Electron density maps are used to establish the positions of individual atoms within a crystal's unit cell. The term "crystal structure coordinates" refers to mathematical coordinates derived from mathematical equations related to the patterns obtained on diffraction of a monochromatic beam of X-rays by the atoms (scattering centers) of a polypeptide in crystal form. The diffraction data are used to calculate an electron density map of the repeating unit of the crystal. The electron density maps are used to establish the positions of the individual atoms within the unit cell of the crystal.

The term "selenomethionine substitution" refers to the method of producing a chemically agent-modified form of the crystal of a protein. The protein is expressed by bacteria in media that is depleted in methionine and supplemented with selenomethionine. Selenium is thereby incorporated into the crystal in place of methionine sulfurs. The location (s) of selenium are determined by X-ray diffraction analysis of the crystal. This information is used to generate the phase information used to construct a three-dimensional structure of the protein.

"Heavy atom derivatization" refers to a method of producing a chemically agent-modified form of a crystal. In practice, a crystal is soaked in a solution containing heavy atom salts or organometallic compounds, e.g., lead chloride, gold thiomalate, thimerosal, uranyl acetate, and the like, which can diffuse through the crystal and bind to the protein's surface. Locations of the bound heavy atoms can be determined by X-ray diffraction analysis of the soaked crystal. This information is then used to construct phase information which can then be used to construct three-dimensional structures of the enzyme as described in Blundel, T. L., and Johnson, N. L., Protein Crystallography, Academic Press (1976), which is incorporated herein by reference.

"Unit cell" refers to a basic parallelepiped shaped block. Regular assembly of such blocks may construct the entire volume of a crystal. Each unit cell comprises a complete representation of the unit pattern, the repetition of which builds up the crystal. "Space group" refers to the arrangement of symmetry elements within a crystal.

"Molecular replacement" refers to generating a preliminary model of a protein whose structural coordinates are unknown, by orienting and positioning a molecule whose structural coordinates are known within the unit cell of the unknown crystal so as best to account for the observed diffraction pattern of the unknown crystal. Phases can then be calculated from this model and combined with the observed amplitudes to give an approximate Fourier synthesis of the structure whose coordinates are unknown. This in turn can be subject to any of the several forms of refinement to provide a final, accurate structure of the unknown crystal (Lattman, E., Meth. Enzymol. 11:55-77, 1985; Rossmann, M G., ed., "The Molecular Replacement Method" 1972, Int, Sci. Rev. Ser., No. 13, Gordon & Breach, N.Y.).

The above-described procedures of protein preparation, crystallization and structure determination are combined with powerful information obtained by hydrogen exchange analysis. A protein or polypeptide of interest is first labeled with an isotope of hydrogen other than $^1H$, for example deuterium ($^2H$) or tritium ($^3H$). This labeling is accomplished under essentially physiologic conditions by incubating the protein of interest in solutions substantially containing water composed of the isotope. The phenomenon of hydrogen exchange is used to substitute an isotope of hydrogen for at least one of the amide hydrogens on the amino acids of the protein of interest.

The term "protein" or "polypeptide" is used herein in a broad sense which includes, for example, polypeptides and oligopeptides, and derivatives thereof, such as glycoproteins, lipoproteins, and phosphoproteins, and metalloproteins. The essential requirement is that the protein contains one or more peptide (—NHCO—) bonds, as the amide hydrogen of the peptide bond (as well as in the side chains of certain amino acids) has certain properties which lends itself to analysis by proton exchange. The protein may be identical to a naturally occurring protein, or it may be a binding fragment or mutant of such a protein. The fragment or mutant may have the same or different binding characteristics relative to the parent protein.

To overcome this difficulty, the following modified approach is utilized for study of brief exchange intervals. Binding protein is contacted with isotope-containing solvent as above, but at the end of the desired on-exchange interval, the solution is contacted with a small volume of liquid phase binding partner. As both binding components are in homogenous liquid phase, complex formation occurs at intervals well less than one second. An excess of aqueous solvent devoid of heavy hydrogen is then optionally added to the binding protein-binding partner complex mixture to effect a substantial dilution ($\frac{1}{10}$ to $\frac{1}{1000}$, preferably $\frac{1}{100}$) of the isotope in the mixture, thereby initiating off-exchange. This mixture is then rapidly applied to a support matrix column (preferably by the flowing stream method) that is capable of binding and attaching the binding partner by any of a variety of methods that are operative at physiologic pH, including the avidin-biotin interaction (in this case the binding partner having been previously biotinylated and the matrix support bearing previously attached avidin) or by way of other well-characterized binding pair interactions.

Continued flow of solvent without isotope over the binding protein-binding partner-bound support matrix further initiates off-exchange. At the end of off-exchange, binding protein is then eluted and removed from the column with an appropriate buffer capable of dissociating the binding protein-binding partner complex; the binding partner-solid support interaction; or both. Preferably one employs procedures that are capable of selectively disrupting the binding protein-binding partner complex without disrupting the support matrix-binding partner interaction (for example, the avidin-biotin interaction) as this will result in the preferred specific elution and recovery from the column of pure off-exchanged binding protein, unadulterated with confounding binding partner.

A preferred embodiment employs binding protein that is first contacted with isotope-containing solvent, and, at the end of the desired on-exchange interval, this solution is contacted with a solution of a previously biotinylated binding partner, with such prior biotinylation being accomplished by any of a number of well known procedures. Complex formation between biotinylated binding partner and binding protein is allowed to occur, generally being complete in less than a second, and then this mixture is optionally diluted to initiate off-exchange, and injected into a flowing stream of physiologic aqueous solvent flowing over a column of support matrix consisting of avidin covalently bound to the matrix. The avidin utilized may variously consist of streptavidin, egg white avidin, or monomeric avidin, or other agent-modified forms of avidin. The linkage to matrix may be by way of any of a variety of functionalities including sodium cyanoborohydride-stabilized Schiff base or that resulting from the cyanogen bromide procedure as applied to carbohydrate matrices. The solid matrices may consist of cross-linked agarose particles or preferably perfusive supports such as those (Poros products) provided by the Perceptive Biosystems company (solid support 20-AL and the like).

For many binding pairs off-exchange may be terminated and selective elution of binding protein accomplished by simply shifting pH to about 2.2 at 0° C. These conditions disrupt many types of binding protein-binding partner complexes but do not disrupt the avidin-biotin interaction, thereby allowing retention on the column of biotinylated binding partner. If shifting to acidic conditions by itself does not result in elution of a particular binding protein, then one of a variety of additional denaturants can be added to the elution solvent, including urea, guanidine hydrochloride, and guanidine thiocyanate at concentrations (preferably 2-4-M guanidine hydrochloride, 1-2 M guanidine thiocyanate) sufficient to elute binding protein but not at the same time disrupt the avidin-biotin interaction and thereby co-elute the binding partner. In general, these conditions do not disrupt the avidin-biotin interaction, even at room temperature. Finally, as above, reductants, such as TCEP, can optionally be admixed with the elution solvent so that it will be present in the binding partner sample when desired.

An additional advantage of the support matrix approach to exchange reactions is that certain embodiments require that the binding protein and binding partner of interest be on-exchanged, complexed with each other, and off-exchanged while present within a mixture of other proteins and biomolecules. In these embodiments, as off-exchange proceeds, it is necessary to isolate the specific binding pair complex of interest. In a preferred embodiment this is accomplished with support matrices as follows. Previously biotinylated binding partner is contacted with a sample containing a mixture of proteins, perhaps a suspension of intact, living cells, or a whole cell extract or digest, or a biologic fluid, such as serum, plasma or blood that also contains the binding protein of interest. Said contacting and mixing results in formation of the biotinylated binding partner-binding protein complex. This mixture, of which the binding pair may be a minor component, is then passed over the aforementioned support matrix containing avidin, wherein the biotinylated complex of interest will specifically attach to the matrix. Washing of the support with aqueous solvent continues (or when desired may initiate) off-exchange and removes from the matrix the irrelevant proteins that were present in the initial mixture, and thereby purifies the binding protein-binding partner complex. At the end of the off-exchange interval, the purified binding protein is simultaneously eluted and shifted to slow exchange conditions as above with an aliquot of appropriate eluent.

Certain target proteins require lipid or detergent environments for expression of their physiologic structure and function. Slowed-exchange-compatible proteolysis of such protein targets can be accomplished with current methods, but further analysis (c18 reversed-phase chromatography, ESI-MS) is not possible because of interference from the associated lipids and/or detergents. The use of microfluidic devices allows such interfering substances to be efficiently and rapidly separated from the peptide fragments, allowing their effective analysis, for example using deuterium exchange-mass spectrometry (DXMS).

Through the use of microfluidic devices, solutions containing target proteins have their buffer composition changed by allowing effective diffusion of the smaller buffer components ($^2H_2O$, $H_2O$, salts, ligands) without effective diffusion of the target protein. In one embodiment, small regenerated cellulose microdialysis fibers (13,000 or 18,000 MWCO, approximately 200 u ID; Spectrum Inc.) are encased in PEEK tubing (15/1000 inch ID) with end fittings that allow a countercurrent sheath solvent flow of exchange solvent while the protein solution flows through the microdialysis fiber. Such devices are capable of very efficient $^2H_2O$ exchange in short times, for example, effecting change to 95% $^2H_2O$ in three seconds at room temperature. Typical flow rates to achieve this end consist of 50 μl/minute for protein solution and 1000 μl/minute for sheath solution.

Such microfluidic devices can also be used to semipurify peptide mixtures that are contaminated with interfering lipids and detergents, such as proteolytic digests of membrane protein preparations. In this application, the proteolytic digest of such a protein is passed through the bore of the microdialysis fiber (flow 5-50 μl/minute) while the countercurrent sheath flow (100-400 μl/min), into which peptide fragments can transfer, (but not the more slowly diffusing and non-dializable lipid/detergent micelles), is directed to and collected on the c18 column for subsequent acetonitrile-gradient elution and MS. The result is that the digest peptides can be analyzed without interference from the lipid/detergent.

Non-constrained devices which utilize differential diffusion to effect changes in buffer composition (such as the "H-reactor" patented by Micronics, Inc.) can also be employed for these purposes. With these devices, flow of sample and exchange buffer is concurrent, not countercurrent, and exchange is therefore necessarily less efficient for a given volume of exchange buffer employed.

Protein Fragmentation Methods

A. Improved Proteolysis Fragmentation

In one preferred method of hydrogen exchange analysis, improved proteolysis fragmentation is employed. In this improved proteolysis method, a simple endopeptidase proteolysis is used to generate a dense sequence-overlapping population of protein fragments for analysis. Prior teachings had found that the common acid-resistant endopeptidases alone, such as pepsin, were not useful in highly localizing amide hydrogen exchange due to insufficient ability to fragment target proteins under acceptable slowed exchange conditions. Pepsin, as employed in the prior art typically had generated a relatively small number of fragments, generally 10-25 amino acids long. The label incorporated on these few useable pepsin-generated peptides was then used to infer the location of label, at best localizing within a range of about 10-25 amino acids (see FIG. 3). Subsequent art taught the use of acid-resistant carboxypeptidases (progressive degradation) after an initial employment of endopeptidases, to localize the labeled amino acid positions within peptides generated when a detailed resolution, such as within 1-5 amino acid residues, is desired (see FIG. 4).

In accordance with the present invention, improved methods that dramatically speed proteolysis, and modulate the sites and patterns of proteolysis by endoproteinases are employed so as to produce highly varied and highly efficient fragmentation of the labeled protein in a single step, thereby avoiding the use of carboxypeptidases completely, an improvement which simplifies the fragmentation and affords a considerable savings of time and cost (see FIG. 5). While these improvements work best in combination with each other, they can be grouped into 3 categories: (i) use of denaturants (systematically varying the type, concentration, duration of denaturation, type of endoproteinase)s) employed, and the duration of endopeptidase digestion) to greatly speed proteolysis and modulate the resulting pattern of fragmentation; (ii) use of solid-state proteolysis with acid-resistant endopeptidases selected for their efficiency and distinctive fragmentation preferences with respect to each other under optimal quench conditions; and (iii) use of water-soluble phosphines to effect rapid and efficient disulfide reduction under quench conditions The use of such endopeptidases under optimized conditions described herein routinely results in the generation of a population of endopeptidase-generated fragments substantially spanning the full length of the majority of proteins studied to date, and, as importantly, yields a large number of additional peptides that partially and mutually overlap in sequence with each other, all obtainable in useful yield. Preferably, the population of fragments contains sequence-overlapping fragments wherein more than half, more preferably 60%-80%, of the members of the population have sequences that are overlapped by the sequences of other members by all but 1-5 amino acid residues. In addition, it is preferable that a majority of members of the population of fragments is present in an analytically sufficient quantity to permit its further characterization, for example, by LC-MS analysis.

An example of the application of this improved proteolysis method and the power of deuterium exchange-mass spectrometry (DXMS) to elucidate protein structure and organization can be found in Hamuro et al., *J. Mol. Biol.* 321:703-714, 2002. Additional references include Hamuro and Woods, *J. Cell. Biochem.*, 37:89-98, 2001; Hamuro et al., *J. Mol. Biol.* 323:871-881, 2002; Hamuro et al., *J. Mol. Biol.* 327:1065-1076, 2003; Englander et al., *Proc. Natl. Acad. Sci. USA* 100:7057-7062, 2003; and Zawadzki et al., *Protein Sci.* 12:1980-1990, 2003.

B. Progressive Proteolysis Fragmentation

In another preferred method of hydrogen exchange analysis, progressive proteolysis (as defined above) is employed to produce protein fragments for label localization. The protein is subjected to a first fragmentation, e.g., with an acid stable proteolytic enzyme, e.g., an endopeptidase such as, for example, pepsin, under slow hydrogen exchange conditions to generate protein fragments. Following the first fragmentation, the resolution of the isotopic hydrogen labeled amides is equivalent to the protein fragment size. Finer localization of the labels is achieved by analysis of subfragments of the protein fragments, which subfragments are generated by progressive degradation of each isolated, labeled protein fragment under slowed exchange conditions. Alternatively, if the protein is smaller than about 30 kDa, the intact protein may be subjected to progressive degradation. For the purpose of the present invention, a protein or a protein fragment is said to be "progressively" (or "stepwise" or "sequentially") degraded if a series of fragments are obtained which are similar to the series of fragments which would be achieved using an ideal exopeptidase, as defined and described in U.S. Pat. No. 6,291,189, column 7, line 58 through column 8, line 33. An ideal exopeptidase will only remove a terminal amino acid. Thus, if the n amino acids of a protein fragment were labeled $A_1$ to $A_n$ (the numbering starting at the terminus at which the degradation occurs), the series of subfragments produced by an ideal exopeptidase would be $A_2$∼∼∼$A_n$, $A_3$∼∼∼$A_{n-1}$–$A_n$, and finally $A_n$.

Preferably each subfragment of the series of subfragments obtained is shorter than the preceding subfragment in the series by a single terminal amino acid residue. However, it is to be understood that exopeptidases do not necessarily react in an ideal manner. Thus, for purposes of the present invention, a protein fragment is said to be progressively degraded, if the series of subfragments generated thereby is one wherein each subfragment in the series is composed of about 1-5 fewer terminal amino acid residues from one end than the preceding subfragment in the series, with preservation of the common other end of the subfamily members. The analyses of the successive subfragments are correlated in order to determine which amino acids of the parent protein fragment were isotopically labeled.

Protein Fragmentation

When the progressive proteolysis protein fragmentation method is employed, the protein is subjected to acid proteolysis with high concentrations of at least one protease that is stable and proteolytically active in the aforementioned slowed hydrogen exchange conditions, e.g., a pH of about 2-3, and a temperature of about 0-4° C., followed by C-terminal subfragmentation with an acid resistant carboxypeptidase, or N-terminal degradation with an acid resistant aminopeptidase. Suitable proteases for the first step include, for example, pepsin (Rogero et al., *Meth. Enzymol.* 131:508-517, 1986.), cathepsin-D (Takayuki et al., *Meth. Enzymol.* 80:565-581, 1981) *Aspergillus* proteases (Krishnan et al., *J. Chromatography* 329:165-170, 1985; Xiaoming et al., *Carlsberg Res. Commun.* 54:241-249, 1989; Zhu et al., *App. Envir. Microbiol.* 56:837-843, 1990), thermolysin (Fusek et al., *J. Biol. Chem.* 265:1496-1501, 1990) and mixtures of these proteases. In one preferred embodiment, pepsin is used, preferably at a concentration of 10 mg/mL pepsin at a temperature of about 0° C. and a pH of about 2.7 for about 5-30 minutes, preferably about 10 minutes.

Separation of Protein Fragments

In one embodiment of the invention, proteolytically fragmented, isotopic hydrogen-labeled protein fragments are separated prior to progressive degradation by means capable of resolving the protein fragments. Preferably, separation is accomplished by reverse phase high performance liquid chromatography (RP-HPLC) utilizing one or more of a number of potential chromatographic supports including $C_4$, $C_{18}$, phenol and ion exchange, preferably $C_{18}$.

Separating the isotopically labeled fragments from the many unlabeled peptides generated by fragmentation of the protein is done under conditions which minimize off-exchange of isotopic hydrogen from the labeled amide sites of the protein fragments. Small protein fragments have little secondary structure, thus amide hydrogens therein freely exchange with hydrogen from the solvent. Conditions for proteolysis and protein fragment separation must therefore be adjusted to slow off-exchange of isotopic hydrogen in order for the isotopic label to remain in place for a time sufficient to complete the method.

The RP-HPLC separation is preferably performed at a pH of about 2.1-3.5 and at a temperature of about 0-4.0° C., more preferably, at a pH of about 2.7 and at a temperature of about 0° C. The preferred separation conditions may be generated by employment of any buffer systems which operate within the above pH ranges, including, for example, citrate, phosphate, and acetate, preferably phosphate. Protein fragments are eluted from the reverse phase column using a gradient of similarly buffered polar co-solvents including methanol, dioxane, propanol, and acetonitrile, preferably acetonitrile. Eluted protein fragments are detected, preferably by ultraviolet light absorption spectroscopy performed at frequencies between about 200 and about 300 nM, preferably about 214 nM. The isotopic label is detected in a sampled fraction of the HPLC column effluent, preferably via either scintillation counting for a tritium label or by mass spectrometry for a deuterium label.

Acid proteases in general have broad cleavage specificity. Thus, they fragment the protein into a large number of different peptides. RP-HPLC resolution of co-migrating multiple peptides is substantially improved by employing a two-dimensional RP-HPLC separation. Preferably, the two sequential RP-HPLC separations are performed at substantially different pH's, for example, a pH of about 2.7 for one separation and about 2.1 for the other sequential separation.

HPLC fractions from a first separation, containing isotopically labeled protein fragments, are then optionally subjected to a second dimension RP-HPLC separation. The second separation may be performed at a pH of from about 2.1 to about 3.5 and at a temperature of from about 0 to about 4° C., more preferably, at a pH of about 2.1 and at a temperature of about 0° C. The pH conditions for the chromatographic separation are maintained by employing a buffer system which operates at this pH, including citrate, chloride, acetate, phosphate, more preferably TFA (0.1-0.115%). Protein fragments are eluted from their reverse phase column with a similarly buffered gradient of polar co-solvents including methanol, dioxane, propanol, more preferably acetonitrile. Eluted protein fragments are detected, the content of isotopic label is measured, and labeled peptides identified as in the first HPLC dimension described above. Labeled protein fragments are isolated by collection of the appropriate fraction of column effluent. Elution solvents are removed by evaporation. The remaining purified protein fragments are each characterized as to primary amino acid structure by conventional techniques such as, for example, amino acid analysis of complete acid hydrolysates or gas-phase Edman degradation microsequencing. The location of the labeled protein fragments within the primary sequence of the intact protein may then be determined by referencing the previously known amino acid sequence of the intact protein. Residual phosphate frequently interferes with the chemical reactions required for amino acid analysis and Edman degradation. This interference is eliminated by the use of trifluoroacetic acid (TFA) in the second dimension buffer so that no residual salt, i.e., phosphate remains after solvent evaporation In one embodiment, proteolytically fragmented, isotopic hydrogen-labeled protein fragments are first separated at pH 2.7 in phosphate buffered solvents and each eluted fragment peak fraction which contains isotopically-labeled amides is identified, collected, and then subjected to a second HPLC separation performed in TFA-buffered solvents at pH 2.1.

High Resolution Sublocalization of Labeled Amides Within Label-Bearing Protein Fragments 1. Subfragmentation of Protein Fragments To localize an isotopic hydrogen labeled peptide amide to the single amino acid level, every peptide bond within a purified label-bearing protein fragment is systematically cleaved. Acidic conditions must be used for this proteolysis because the small protein fragments and subfragments generated have no stable conformational structure and rapid loss of isotopic hydrogen label from the amides would occur if rates of exchange were not slowed by ambient acidic pH.

Progressive degradation is preferably achieved by treatment with at least one acid stable exopeptidase enzyme, more preferably with at least one carboxypeptidase. The progressive degradation is performed at acidic pH to minimize isotopic hydrogen losses. Thus, enzymes that are substantially inactivated by the required acidic buffers are of limited use in the method of the invention. However, several carboxypeptidases are enzymatically active under acid conditions, and thus are suitable for proteolysis of protein fragments under acidic conditions, e.g., pH 2-3.

Most known acid-reactive proteases cleave peptides in a nonspecific manner similar to pepsin. One class of acid-reactive proteases, the carboxypeptidases, is able to generate all required subfragments of proteolytically-generated protein fragments in quantities sufficient for high resolution localization of an isotopic hydrogen label. Many carboxypeptidases are active at pH 2-3 and sequentially cleave amino acids from the carboxy terminus of protein fragments. Such enzymes include, for example, carboxypeptidases P, Y, W, and C (Breddam, *Carlsberg Res. Commun.* 51:83-128, 1986). The need to minimize isotopic hydrogen losses precludes the use of carboxypeptidases which are inactive in acidic (pH 2.7) buffers, such as carboxypeptidases A and B.

Progressive degradation of purified isotopic hydrogen label-bearing protein fragments is preferably performed with one or more acid resistant carboxypeptidase under conditions that produce a complete set of amide-labeled subfragments, wherein each subfragment is shorter than the preceding subfragment by 1-5 carboxy terminal amino acids, preferably by a single carboxy-terminal amino acid. HPLC analysis of the resulting series of subfragments allows the reliable assignment of label to a particular amide position within the parent labeled protein fragment.

In one preferred embodiment, isotopic hydrogen-labeled proteins are nonspecifically fragmented with pepsin or one or more pepsin-like proteases. The resulting labeled protein fragments are isolated by two-dimensional HPLC. These labeled protein fragments are then exhaustively subfragmented by progressive degradation with one or more acid-reactive carboxypeptidases. The resulting digests are then analyzed via RP-HPLC performed at a temperature of about 0° C. in TFA-containing buffers (pH about 2.1). Each of the generated subfragments (typically 5-20) is then identified as to its structure and content of isotopic hydrogen label. The isotopic hydrogen label is thereby assigned to specific peptide amide positions.

Controlled progressive degradation from the carboxy-terminus of isotopic hydrogen labeled protein fragments with carboxypeptidases can be performed under conditions which result in the production of analytically sufficient quantities of a series of carboxy-terminal truncated subfragments, each shorter than the preceding subfragment by a single carboxy-terminal amino acid. As each carboxy-terminal amino acid of the labeled protein fragment is sequentially cleaved by the carboxypeptidase, the peptide amide nitrogen which exhibits slow hydrogen exchange under the process conditions is converted to a secondary amine which exhibits rapid hydrogen exchange. Thus any isotopic hydrogen label at that nitrogen is lost from the protein subfragment within seconds, even at acidic pH. A difference in the molar quantity of label associated with any two sequential subfragments indicates that the isotopic label is localized at the peptide bond amide between the two subfragments.

2. Location of the Isotopic Hydrogen Label

In one preferred embodiment, synthetic peptides are produced (by standard peptide synthesis techniques) that are identical in primary amino acid sequence to each of the labeled proteolytically-generated protein fragments. The synthetic peptides may then be used in preliminary carboxypeptidase subfragmentation at a pH of about 2.7 and a temperature of about 0° C., and HPLC (in TFA-buffered solvents) studies to determine: 1) the optimal conditions of proteolysis time and protease concentration which result in the production and identification of all possible carboxypeptidase products of the protein fragment under study; and 2) the HPLC elution position (mobility) of each carboxypeptidase-generated subfragment of synthetic peptide.

In one preferred aspect thereof, a set of synthetic peptides may be produced containing all possible carboxy-terminal truncated subfragments which an acid carboxypeptidase could produce upon treatment of a "parent" protein fragment. These synthetic peptides serve as HPLC mobility identity standards and enable the identification of carboxypeptidase-generated subfragments of the labeled protein fragment. Certain subfragments may be enzymatically produced by carboxypeptidase in quantities insufficient for direct amino acid analysis or sequencing. However, the quantity of the carboxypeptidase-generated subfragments is sufficient for identification by measuring HPLC mobility of such subfragments and comparing to the mobility of the synthetic peptides. Protein fragments and subfragments can be detected and quantified by standard in-line spectrophotometers (typically UV absorbance at 200-214 nM) at levels well below the amounts needed for amino acid analysis or gas-phase Edman sequencing.

After these preliminary studies, the proteolytically-generated HPLC-isolated, isotopically-labeled protein fragment is subfragmented with a carboxypeptidase and analyzed under the foregoing experimentally optimized conditions. The identity of each fragment is determined (by peptide sequencing or by reference to the mobility of synthetic peptide mobility marker) and the amount of isotopic hydrogen associated with each peptide subfragment is determined.

Denaturation and Disulfide Reduction

With some proteins, there is an absolute requirement for the employment of denaturants to effect fragmentation under quench conditions. An example of a protein with such an absolute dependency is Hen Egg White Lysozyme (HEL). In a preferred embodiment, the labeled protein is exposed, before fragmentation, to denaturing conditions compatible with slow hydrogen exchange and sufficiently strong to denature the protein enough to render it adequately susceptible to the intended proteolytic treatment. If these denaturing conditions would also denature the protease, then, prior to proteolysis, the denatured protein is switched to less denatured conditions (still compatible with slow H-exchange) sufficiently denaturing to maintain the protein in a protease-susceptible state but substantially less harmful to the protease in question. Preferably, the initial denaturant is guanidine thiocyanate, and the less denaturing condition is obtained by dilution with guanidine hydrochloride. Guanidine hydrochloride is an effective denaturant at a concentration of about 0.05-4 M.

In previous studies by Englander et al. and others recited above, proteolytic fragmentation of labeled proteins under slowed-exchange conditions was suitably accomplished by simply shifting the protein's pH to 2.7, adding high concentrations of liquid phase pepsin, followed by (10 minute) incubation at 0° C. With the proteins studied and reported by others to date, simply shifting pH from that of physiologic (7.0) to 2.7 was sufficient to render them sufficiently denatured as to be susceptible to pepsin proteolysis at 0° C. Furthermore, these reported proteins, in general, did not contain disulfide bonds that interfered with effective denaturation by such (acid) pH conditions or contain disulfide bonds within portions of the protein under study with the technique.

However, in accordance with the present invention, it has been found that other proteins (for example, HEL) are negligibly denatured and are not substantially susceptible to pepsin proteolysis when continuously incubated at comparable acidic pH and depressed temperature (10-0° C.) for several hours. This is likely the consequence of the existence of a thermal barrier to denaturation for many proteins incubated in many denaturants; i.e., denaturation of proteins at lower temperatures (10-0° C.), an absolute requirement for hydrogen exchange quench, is often inefficient and a slow process, incompatible with the requirement of medium resolution hydrogen exchange techniques that manipulations be performed rapidly, such that the attached label is substantially retained at functionally labeled amides of the protein.

Using the methods of the present invention, it has been discovered that such proteins become extraordinarily susceptible to pepsin proteolysis at 0° C. when they are treated with the sequential denaturation procedure described below.

While proteins are often subjected to purposeful denaturation with agents other than a pH shift prior to digestion with pepsin, this has never been done at depressed temperatures (10-0° C.) before, and the it has been discovered herein that while guanidine thiocyanate at the indicated concentrations is sufficient to suitably denature and render susceptible to pepsin proteolysis proteins at 10-0° C., several other strong denaturants, including urea, HCl, sodium dodecyl sulfate (SDS) and guanidine HCl, were, at least when used alone, unable to adequately denature lysozyme at these low temperatures. However, the concentrations of guanidine thiocyanate required for such denaturation are incompatible with pepsin digestion; i.e., they denature the pepsin enzyme before it can act on the denatured binding protein. When the guanidine thiocyanate is removed (at 10-0° C.) from the solution after protein denaturation has been accomplished in an attempt to overcome this inhibition of pepsin activity, the protein rapidly refolds and/or aggregates, which renders it again refractory to the proteolytic action of pepsin.

It has been discovered herein that if proteins are first denatured in about 1.5-4 M (preferably $\geq$2M) guanidine thiocyanate at 0° C. and the concentration of thiocyanate then reduced to preferably $\leq$0.5 M, while at the same time the guanidine ion is maintained at about 0.05-4 M (preferably $\geq$2M) (by diluting the guanidine thiocyanate-protein mixture into guanidine hydrochloride solution), the denatured protein remains in solution, remains denatured, and the enzyme pepsin remains proteolytically active against the denatured protein in this solution at 0° C. The denatured (or denatured and reduced) protein solution is then passed over a pepsin-solid-support column, resulting in efficient and rapid fragmentation of the protein (in less than 1 minute). The fragments can be, and usually are, immediately analyzed on RP-HPLC without unnecessary contamination of the peptide mixture with the enzyme pepsin or fragments of the enzyme pepsin. Such contamination is problematic with the technique as taught by Englander et al., as high concentrations of pepsin (often equal in mass to the protein under study) are employed, to force the proteolysis to occur sufficiently rapidly at 0° C.

The stability of pepsin-agarose to this digestion buffer is such that no detectable degradation in the performance of the pepsin column employed by the methods of the present invention has occurred after being used to proteolyze more than 500 samples over 1 year. No pepsin autodigestion takes place under these conditions. Denaturation without concomitant reduction of the binding protein may be accomplished by contacting it (at 0-5° C.) with a solution containing $\geq$2M guanidine thiocyanate (pH 2.7), followed by the addition of an equal volume of 4 M guanidine hydrochloride (pH 2.7).

Subsequent to this discovery of the extraordinary stability to denaturation of HEL under quench conditions, and the foregoing remedy, it has been found that all other proteins studied to date by methods of the present invention are susceptible, at least to a minimal degree, to pepsin proteolysis under simple quench conditions, but that the speed and extent of fragmentation can be dramatically increased by the addition of suitable concentrations of guanidine hydrochloride (GuHCl) alone, without the use of guanidine thiocyanate. There is considerable virtue in avoiding the use of thiocyanate when possible: there is a variable (often severe) aggregation and precipitation of some of the denatured protein as the thiocyanate is diluted out prior to proteolysis, greatly confounded automated sample processing.

FIG. 6 presents the fragmentation patterns seen when the protein phospholipase A2, under quench conditions (pH 2.2, 0° C.), is incubated with varying concentrations of GuHCl (0-4M) for 20 seconds, and then contacted with a pepsin-solid support column (30 mg/ml, Poros 20-AL media; 66 microliters bed volume) for an additional 30 seconds. Fragments were contemporaneously loaded on a microbore c18 column and then eluted with an acetonitrile gradient over 10 minutes, again at pH 2.2, 0° C., with the effluent directed to a Finnigan LCQ mass spectrometer operating at a capillary temperature of 200° C. Data was acquired in both data dependent MS2 mode (to allow peptide identification) and in MS1 mode (to assess the suitability of the isotopic envelope data for subsequent deuterium quantification (signal, signal to noise, spectral overlap with confounding fragments). When no GuHCl was used, less than 15 peptides in sufficient yield were identified (data not shown). When 0.05 M GuHCl was used, more than 70 high quality peptides were obtained, with further improvement when 0.5 M denaturant was employed. While 4.0 M denaturant resulted in the identification of additional peptides, some were also lost when compared to the 0.5M digest.

In accordance with the present invention, it has been found that several variables behave independently in determining the speed and pattern of digestion, and that their effects are distinctive for each target protein studied. Typically, up to 30 combinations of these variables are evaluated (employing the automated features of the hydrogen exchange apparatus described herein, see FIG. 2) to establish optimal fragmentation conditions for the protein under study. These independent variables include the type of denaturant (e.g., GuSCN versus GuHCl); its concentration preferably (0.05-4M); the time the denaturant is allowed to act on the protein prior to fragmentation (preferably 0 to 3 minutes); the type(s) of endoproteinases employed; and the time allowed for digestion (preferably 20 seconds to 2 minutes). For most proteins studied, GuHCl, at a concentration of 0.5M and 30 seconds fragmentation on a pepsin column as above is near-optimal, though more extensive tuning will likely improve the fragmentation map.

FIG. 7 presents results obtained when horse cytochrome c was quenched with or without 0.5M GuHCl, and then fragmented with either pepsin (P1), Newlase (P2) or Fungal Protease XIII (P3) coupled to perfusive supports (20-30 mg/ml), and analyzed as in FIG. 6. Considerable variation in digestion pattern and yield is seen with the several conditions. The arrows at the top of the figure indicate the positions of the C- and N-termini of the aggregate peptides produced, highlighting the extreme degree of overlap of the resulting set of peptide fragments. Even when denaturant is omitted the results of the solid state pepsin digestions were superior to those disclosed by others in which cytochrome c was fragmented with liquid-phase pepsin, where fewer than 15 useful peptides were obtained in a 10 minute digestion.

FIG. 8 presents the fragmentation map obtained for a human von Willebrand Factor construct (denatured in 0.5 M GuHCl) employing a 40 second digestion on a pepsin column. In this study it was found useful to simultaneously reduce an internal disulfide bond by mixing TCEP (1.0 M final concentration) with the denaturant.

It is to be emphasized that the speed of generation (typically in 30 seconds) and the yield and extent of the highly overlapping fragmentation seen using the high resolution hydrogen exchange methods presented herein is unprecedented in the previously disclosed art, and was unanticipated until these recent results. There was no expectation that the art of modulating endopeptidase activity-both in terms of producing the needed varied fragmentation and yield could be enhanced enough to be useful by itself for high resolution localization of label. Heavy hydrogen label is quickly lost from proteolytic fragments during analysis, even under quench conditions: thus, all steps of analysis should be performed as quickly as possible, including protease digestion. The methods developed and available prior to 1997 required pepsin degradation durations that were already at the upper limits of acceptable times (approximately 10 minutes). For example in U.S. Pat. No. 6,291,189, it is stated that: "In a preferred embodiment, pepsin is used, preferably at a concentration of 10 mg/ml pepsin at 0° C., pH 2.7 for 5-30 minutes, preferably 10 minutes." It was therefore unanticipated that more extensive digestions could be obtained with pepsin with or without other endoproteinases given the time constraints of amide hydrogen exchange study.

Accordingly, the methods of the present invention analyze endopeptidase fragments that are generated by cleaving the labeled protein with an endopeptidase selected from the group consisting of a serine endopeptidase, a cysteine endopeptidase, an aspartic endopeptidase, a metalloendopeptidase, and a threonine endopeptidase (a classification of endopeptidases by catalytic type is available on the world wide web at the URL "chem.qmul.ac.uk/iubmb/enzyme/EC34"; by the Nomenclature Committee of the International Union of Biochemistry and Molecular Biology). Presently preferred endopeptidases include pepsin, newlase and acid tolerant *Aspergillus* proteases such as *Aspergillus* protease XIII. FIGS. 8 and 9 demonstrate the distinctive fragmentation patterns that can be obtained with each of the endoproteinases employed in methods of the present invention. It has further been found that the fragmentation patterns resulting from simultaneous, and/or sequential proteolysis by combinations of these enzymes are additive in their effect on fragmentation. Therefore, more than one endopeptidase may be used in combination. Optimally, endopeptidase fragments are generated at a pH of about 1.8-3.4, preferably 2-3, more preferably in the range of about 2.1-2.3 or 2.5-3.0.

In preferred embodiments, the endopeptidase may be coupled to a perfusive support material to facilitate manipulation of digestions, as an alternative to liquid phase digestions. This allows the reuse of endopeptidase materials and separates the enzyme from the fragments for further analysis. Exemplary perfusive support matrices include Poros 20 media, wherein digestion of the labeled protein is accomplished by contacting a solution of the labeled protein with said matrix, followed by elution of generated fragments from the matrix. With the use of the solid support, sample digestion under slowed exchange conditions can be performed that results in no detectable endoproteinase autodigestive fragments being released into the digestion product, i.e., the population of labeled protein fragments. Furthermore, the endoproteinases remain fully active and available for subsequent repeated use as a digestive medium for additional samples.

In accordance with the present invention, it has been discovered herein that the judicious admixture of denaturants with substrate protein results in the ability to greatly promote and "tune" substrate fragmentation. Unfortunately, these same denaturants retard and/or inhibit the activity of the enzymes unless denaturants are partially removed prior to proteolysis. However their removal allows the substrates to re-fold, negating the benefit of the denaturant. Gradual manual dilution of the substrate-enzyme-denaturant mixture allowed an initially slow proteolysis to proceed. With subsequent dilution, partially degraded substrate is unable to refold; and because of denaturant dilution, protease activity increases, further fragmenting the initial large substrate fragments. Success in this method required multiple manual additions of reagents, denaturants, and timed addition of diluents, all very labor intensive. The improved methods of the present invention use solid-state enzymes on perfusive supports and column chromatography, enabling samples to be applied to the column already mixed with denaturant, and the necessary dilution of denaturant automatically occurs as the substrate slug passes down the column, now progressively diluted with the fluid in the column void volume as proteolysis proceeds. This results in tremendous labor savings, and is readily automated. There is thus an unanticipated ease and simplification of use of the necessary denaturants when solid phase proteases are employed.

A variety of acid-reactive endoproteinases can be covalently coupled to any of a number of available support matrices including, for example, cross-linked dextran, cross-linked agarose, as well as more specialized supports suitable for modem HPLC chromatography, preferably the Poros line of perfusive support materials supplied by Perceptive Biosystems, such as "20-AL" and the like. These latter supports are particularly advantageous for invention methods as they allow rapid interaction of substrate with bound peptidases. The coupling of endoproteinases to matrices can be achieved by any of a number of well-known chemistries capable of effecting such couplings, including, for example, aldehyde-mediated (sodium cyanoborohydride-stabilized Schiff base), carbodiimide, and cyanogen bromide-activated couplings. Conditions, including pH, conducive to the continued stability of particular peptidases may optionally be employed, and could readily be implemented by one of skill in the art.

An exemplary preparation of coupled endopeptidase is as follows. The endopeptidase is obtained as a lyophilized powder, reconstituted with distilled water, and dialyzed against a coupling buffer containing 50 mM citrate (pH 4.4). The peptidase is then coupled to Perceptive Biosystems Poros media 20-AL following the manufacturer's recommended coupling procedures, including "salting out" with high sodium sulfate concentrations. Couplings can be performed at a ratio of 5 to 30 mg of peptidase per ml of settled 20-AL matrix, preferably 30 mg/ml. The coupled matrix can then be stored in the presence of sodium azide to minimize bacterial contamination.

While any of a number of batchwise or column chromatographic approaches might be employed to effect matrix-bound endopeptidase digestion of labeled protein under slowed exchange conditions, the following approach has been found to work well and to be preferable. A stainless steel column (length 2 cm, width 2.2 mm, internal volume approximately 66 microliters) was packed with endoproteinase-derivatized 20-AL support coupled with protein at 30 mg/ml) and flow established with a solvent consisting of 0.5% formic acid (for pepsin, newlase, or *Aspergillus* protease XIII), said column being operated at 0° C. Care must be taken to employ buffers with a pH compatible with rapid peptidase action: buffers with a pH of 2.7-3.0 (room temperature measurement) work well. An aliquot of labeled protein to be fragmented was contacted with the column matrix typically in a volume of 10-300 microliters, preferably 100 microliters, and the sample allowed to reside on the column for a time determined (by preliminary titration studies) to result in the desired degree of fragmentation. It has been surprisingly found herein that digestion times of 13 seconds to 5 minutes, preferably less than a minute, more preferably, less than 40 seconds to be optimal. Prior knowledge of endopeptidase digestion suggested that digestion times of greater than 10 minutes would be required to produce sufficient fragmentation. The sample was then flushed from the column onto either an analytical reverse phase HPLC column for subsequent separation and analysis of the peptide fragments, or directly without additional purification or chromatography onto a mass spectrometer for analysis. During this analysis period, the column is flushed (with the effluent going to waste) with an excess of solvent to remove any peptide or subfragments which nonspecifically adhere or are otherwise retained in the matrix, thereby preparing the column for a repeated use. Such washing buffers can be any of a wide variety of buffers including the buffers used for digestion. The column-washing step (between each sample digestion) is preferable but not absolutely required for success.

In an additional embodiment, a column containing one of these solid state proteases can be used to further digest peptides on-line as they each independently exit the reversed phase (RP) HPLC column during gradient elution. This approach has the considerable advantage of producing a much less complex mixture of peptides to analyze than when two enzymes act on the substrate before RP-HPLC. To use these enzymes in this post-chromatography manner, it may be useful to reduce the acetonitrile concentration in the effluent stream prior to passage over the protease column, as acetonitrile can reversibly (and irreversibly) inhibit these enzymes.

In addition, disulfide bonds, if present in the protein to be digested, can also interfere with analysis. Disulfide bonds can hold the protein in a folded state where only a relatively small number of peptide bonds are exposed to proteolytic attack. Even if some peptide bonds are cleaved, failing to disrupt the disulfide bonds would reduce resolution of the peptide fragments still joined to each other by the disulfide bond; instead of being separated, they would remain together. This would reduce the resolution by at least a factor of two (possibly more, depending on the relationship of disulfide bond topology to peptide cleavage sites).

In one embodiment, water soluble phosphines, for example, Tris (2-carboxyethyl) phosphine (TCEP) may be used to disrupt a protein's disulfide bonds under "slow hydrogen exchange" conditions. This allows much more effective fragmentation of large proteins which contain disulfide bonds without causing label to be lost from the protein or its proteolytic fragments (as would be the case with conventional disulfide reduction techniques which must be performed at pHs which are very unfavorable for preservation of label).

High resolution localization of label-bearing amides with the use of endoproteinases requires the proteolytic generation of numerous sequence-overlapped fragments under conditions which allow the label to remain in place (e.g., 0°

C., pH 2.2). The ability of any protease to fragment a protein or peptide is limited by the accessibility of the protease to susceptible peptide bonds. While denaturants such as acidic pH, urea, detergents, and organic co-solvents can partially denature proteins and expose many otherwise structurally shielded peptide bonds, pre-existing disulfide bonds within a protein can prevent sufficient denaturation with these agents alone. In conventional protein structural studies, disulfides are usually cleaved by reduction with 2-mercaptoethanol, dithiothreitol, and other reductants which unfortunately require a pH greater than 6 and elevated temperature for sufficient activity, and are therefore not useful for the reduction of disulfides at pH 2.7 or below. For this reason, the hydrogen exchange art has not attempted any form of disulfide bond disruption, has for the most part been restricted to the study of proteins without intrinsic disulfide bonds, and has accepted the low resolution achievable without disulfide bond disruption.

It has been recognized and demonstrated herein that acid-reactive phosphines such as Tris (2-carboxyethyl) phosphine (TCEP) can be used to disrupt disulfides under the acidic pH and low temperature constraints required for hydrogen exchange analysis. These manipulations disrupt these associations and at the same time continue to produce a markedly slowed proton exchange rate for peptide amide protons.

Denatured (with or without reduction) labeled protein is then passed over a column composed of insoluble (solid state) pepsin, whereby during the course of the passage of such denatured or denatured and reduced binding protein through the column, it is substantially completely fragmented by the pepsin to peptides of size range 2-20 amino acids at 0° C. and at pH 2.7. The effluent from this column (containing proteolytically-generated fragments of labeled protein) is directly and immediately applied to the chromatographic procedure employed to separate and analyze protein fragments, preferably analytical reverse-phase HPLC chromatography and/or mass spectrometry.

In preferred embodiments, proteins containing disulfide bonds may be first physically attached to solid support matrices, and then contacted with solutions containing TCEP at acidic pH and low temperature for more rapid reactions than are possible in solution. In this preferred embodiment, with all steps performed at 5-0° C., preferably 0° C., the protein in aqueous solution, with or without prior denaturation and under a wide variety of pH conditions (pH 2.0-9.0) is first contacted with a particulate silica-based reverse-phase support material or matrix typically used to pack HPLC columns, including C4 and C18 reversed phase silica supports, thereby attaching the protein to the surface of such material. Unbound binding protein may then optionally be washed off the support matrix with typical aqueous HPLC solvents, (0.1% trifluoroacetic acid, (TFA) or 0.1-0.5% formic acid in water, buffer A). An aliquot of a substantially aqueous buffer containing TCEP at a pH between 2.5 and 3.5, preferably 2.7 is then contacted with the protein that is attached to the support material and allowed to incubate with the attached protein near 0° C. and preferably for short periods of time (0.5-20 minutes, preferably 5 minutes) and then the TCEP-containing buffer removed from the support matrix by washing with buffer A, followed by elution of the reduced binding protein from the support matrix by contacting the support with eluting agents capable of disrupting the support-protein binding interaction, but also compatible with continued slow hydrogen exchange (pH 2.0-3.5; temperature 0-5° C.).

An example of this preferred embodiment to achieve disulfide reduction prior to pepsin fragmentation is as follows. Labeled protein is applied to a reverse phase silica-based C18 HPLC support matrix in a column (for example, Vydac silica-based C18, catalog #218TP54, or Phenominex silica-based C18 Jupiter 00B4053-B-J) that has been pre-equilibrated with HPLC solvent A (0.1% TFA or 0.1-0.5% formic acid at 0-5° C. After substantial binding of the lysozyme has occurred (usually within seconds), additional buffer A is passed through the column to remove small quantities of unattached binding protein. A solution containing TCEP (50-200 micrometers of TCEP (0.05-2.0 M in water at a pH of 2.5-3.5, preferably 3.0) is then applied to the column in a manner that results in its saturation of the portion of the column to which the binding protein has been previously attached. Flow of solvent on the support is then stopped to allow incubation of the TCEP solution with the support matrix-attached binding protein. At the end of this incubation time (variously 0.5 minutes-20 minutes, preferably 5 minutes) flow of solvent A is resumed, resulting in the clearance and washing of the TCEP solution from the support matrix. This is followed by application of an amount of solvent B (20% water, 80% acetonitrile, 0.1% TFA) sufficient to release the binding protein from the support (typically 30-50% solvent B in solvent A). This eluted and reduced protein is then passed over a pepsin column to effect its fragmentation under slowed exchange conditions. The protein fragments resulting from the action of the pepsin column on the reduced protein are then contacted with another analytical HPLC column, preferably a reverse phase HPLC support, and the fragments sequentially eluted from the support with a gradient of solvent B in solvent A.

An example of an alternative preferred embodiment to achieve disulfide reduction after pepsin fragmentation is as follows. This alternative approach is to first denature the protein under slow exchange conditions, pass it over a pepsin column to effect fragmentation, apply the resulting fragments to a HPLC support matrix, effect reduction of the support-bound peptide fragments by contacting them with the aforementioned TCEP solution, followed by sufficient incubation at 0° C., finally followed by elution of the reduced fragments from the column with increasing concentrations of solvent B. The advantage of this second alternative method is that an entire HPLC support matrix attachment-detachment step is avoided, resulting in a simplification of the manipulations and equipment required for the procedure, as well as savings in elapsed time. This approach is not probable when a particular protein requires substantial prior reduction of disulfides to become substantially susceptible to the digestive actions of pepsin. Certain proteins are sufficiently stabilized by their contained disulfide bonds that they may not become substantially susceptible to pepsin even in the presence of strong denaturants. In such cases it will be preferable to apply the first method of reduction (above), where the protein is first reduced "on column", eluted, fragmented on the pepsin column, and the fragments then optionally applied to an additional column matrix to effect separation from each other.

Additionally, it has been found herein that the simultaneous use of denaturants and reductants (TCEP) results in synergistic enhancement of both protein denaturation and reduction, not seen when employed separately, or even sequentially.

Deconvolution of Endopeptidase-generated Fragments in Methods Employing Improved Proteolysis Fragmentation Mass spectroscopy has become a standard technology by which the amino acid sequence of proteolytically generated peptides can be rapidly determined. It is commonly used to study peptides which contain amino acids which have been deuterated at carbon-hydrogen positions, and thereby determine the precise location of the deuterated amino acid within the peptide's primary sequence. This is possible because mass spectroscopic techniques can detect the slight increase in a particular amino acid's molecular weight due to the heavier mass of deuterium. McCloskey (*Meth. Enzymol.* 193:329-338, 1990) discloses use of deuterium exchange of proteins to study conformational changes by mass spectrometry. The methods of the present invention include measuring the mass of endopeptidase-generated fragments to determine the presence or absence, and/or the quantity of deuterium on the endopeptidase-generated fragments. Preferably, mass spectrometry is used for mass determination of these peptide fragments. This allows determination of the quantity of labeled peptide amides on any peptide fragment.

According to the methods of the present invention, proteolytically generated fragments of protein functionally labeled with deuterium may be identified, isolated, and then subjected to mass spectroscopy under conditions in which the deuterium remains in place on the functionally labeled peptide amides. Standard peptide sequence analysis mass spectroscopy can be performed under conditions which minimize peptide amide proton exchange: samples can be maintained at 4° C. to 0° C. with the use of a refrigerated sample introduction probe; samples can be introduced in buffers which range in pH between 1 and 3; and analyses are completed in a matter of minutes. MS ions may be made by MALDI (matrix-assisted laser desorption ionization) electrospray, fast atom bombardment (FAB), etc. Fragments are separated by mass by, e.g., magnetic sector, quadrupole, ion cyclotron, or time-of-flight methods. For MS methods generally, see Siuzdak, G., Mass Spectrometry for Biotechnology (Academic Press 1996).

Once the endopeptidase fragmentation data is acquired on functionally deuterated protein, it is then deconvoluted to determine the position of labeled peptide amides in an amino acid specific manner. In general, the term "deconvoluted" as used herein refers to the mapping of deuterium quantity and location information obtained from the fragmentation data onto the amino acid sequence of the labeled protein to ascertain the location of labeled peptide amides, and optionally their rates of exchange. Deconvolution may comprise comparing the quantity and/or rate of exchange of isotope(s) on a plurality of endopeptidase-generated fragments with the quantity and rate of exchange of isotope(s) on at least one other endopeptidase fragment in the population of fragments generated, wherein said quantities are corrected for back-exchange in an amino acid sequence-specific manner. Labeled peptide amides can optionally be localized in an amino acid sequence-specific manner by measuring rates of off-exchange of functionally attached label under quenched conditions. The determination of the quantity and rate of exchange of peptide amide hydrogen(s) may be carried out contemporaneously with the generation of the population of endopeptidase-generated fragments.

Although several alternative methods for effecting such deconvolution may be available, at least one useful method has been implemented and demonstrated herein. FIG. 9 presents the results of such a deconvolution. A protein construct composed of a two repeat segment (16-17) of chicken brain spectrin was on-exchanged in deuterated buffer for varying times (10 to 100,000 seconds, at 22° C.). Samples were then exchange-quenched, in 0.5 M GuHCl, pH 2.2, and otherwise processed as shown in FIG. 6. The deuterium content of the 113 useful peptides resulting from such fragmentation was determined from the raw MS data with corrections for back-exchange made employing the inexact "peptide average" method of Zhang and Smith (Zhang et al., *Prot. Sci.* 2:522-531. 1993).

Plots of deuterium buildup versus time were constructed for each peptide, and the number of amides exchanging in arbitrary "fast, medium and slow" classes (light, medium, and dark grey shading respectively in the figure) determined for each peptide. An initial map of rates versus amino acid sequence was then constructed from this information employing a strategy in which "pieces" (fragments) with uniform rate class (each class given a color), were first placed in register, and subsequent placement of more complexly colored pieces (two colors then three colors) performed in a manner that required that the several "colors" in these peptides be reconciled vertically to conform with the color placement of the preceding pieces. The average color (rate class) at each amide position was then determined and used to construct the initial map. Unmeasureable amide hydrogens (approximately 10% of the total amides in the 113 fragments, unmeasured either because of errors incurred because of the approximate (average) back-exchange calculation method employed, or because the very slowest exchanging amides were not measured in this experiment) were then fit to the provisional map in a manner that minimized deviation from said map, and a final map constructed by averaging this final placement of "pieces".

The choice of three rate classes was arbitrary, and done to simplify, the "piece placement" work, which was done manually in this example. Assignment of amides in each peptide to each of 9 rate classes (9 time points were employed in this experiment) would considerably improve the resolution of the deconvolution, but is conveniently performed by automated (computational) means, and with incorporation of more precise back-exchange corrections as discussed below. Further fragmentation of this protein construct with pepsin plus Fungal protease XIII has resulted in a 50% increase in the number of spectrin fragments, which will preferably be deconvoluted through linear programming-mediated approaches.

The essential attributes of a preferred deconvolution algorithm for such high density, overlapping endopeptidase fragment data include that: (i) it takes as inputs the measurements of the quantity of label on the numerous overlapping endopeptidase-generated fragments correlated with their amino acid (aa) sequence; (ii) it more precisely corrects for back-exchange (that is, label lost subsequent to initiation of quench, during the analysis step) than the presently employed method that calculates an average correction factor for all amides in a peptide (Zhang et al., *Prot. Sci.* 2:522-531, 1993) and instead employs a correction that is sub-site-specific (specific for 1-5 contiguous amides, depending on the resolving power of the aggregate endopeptidase fragments available). This can be done both computationally (by reference to the Bai/Englander-algorithm; Bai et al: *Proteins: Struct. Funct. Genet.* 17:75-86, 1993) or alternatively experimentally by measuring back exchange under quench conditions, of the substantially random coil fragments resulting from identical endoproteolysis of a fully (equilibrium) deuterated sample of the protein in a manner that allows the rate(s) of loss of deuterium to be measured over time for each resolvable sequence region. Either approach affords precise calculation of the label lost through back exchange from each peptide, and, by comparison, that lost in each aa segment that differs between aa sequence-overlapping peptides. Corrections for these losses are made for each peptide/aa overlap difference value; (iii) it compares the (corrected) label content of each peptide with the label content of all peptides with which it (or immediately adjoining peptides) share any part of aa sequence, said comparisons being performed in a manner which allows differences in label content to be assigned to regions of aa sequence difference, with the preferred algorithm seeking to fit deuterium location and quantity at each location in a manner that optimizes agreement between results obtained from the plurality of fragments; and (iv) it optionally makes use of measurements of off-exchange rates of label on quenched fragments, which, by reference to the above noted site-specific rate (under quench conditions) prediction or empirical determination from endoproteinase fragmentation data of equilibrium-deuterated protein) can be employed to further sublocalize label at regions unresolved by analysis of fragments alone at one quench condition duration. heat and melt a frozen sample rapidly and under precise temperature control. Under computerized control, the autosampler's mechanical arm lifts the desired sample from the −80° C. sample well, and places it in the autosampler heater/mixer/vortexer which rapidly melts the sample at 0-5° C. The liquified sample is then automatically injected onto the HPLC column.

Optional modifications to a such a standard autosampler may include: modification of the sample basin to provide an insulated area in which dry ice can be placed, resulting in chilling of the remaining areas of the sample rack to −50 to −80° C.; placement of the autosampler within a 0-5° C. refrigerator, and "stand-off" placement of the sample preparation and sample injection syringe assemblies of the autosampler outside the refrigerator, but with otherwise nominal plumbing and electrical connection to the autosampler. An external personal computer (PC) (running Procom, and a dedicated Procrom script "Asset1"), delivers certain settings to firmware within the autosampler, allowing: (i) a much shortened subsequent post-melting dwell time of samples in the chilled basin, avoiding re-freezing of sample prior to injection; and (ii) allowing its heater/mixer to regulate desired temperatures when they are less than the default minimum temperature of 30° C.

The "sample preparation" module (B), automatically performs the "functional deuteration" or sample preparation manipulations, quench, and denaturation in large part through use of the solid-state inventions as described earlier herein, for example, using a protein conjugated to solid phase beads. Several components of this module will benefit from the microfluidics inventions also described earlier.

Typically, deuterated samples are manually prepared (both at 0° C., and at room temperature) by diluting 1 µL of protein stock solution with 19 µL of deuterated buffer (150 mM NaCl, 10 mM HEPES, pD 7.4), followed by "on-exchange" incubation for varying times (10 sec, 30 sec, 100 sec, 300 sec, 1000 sec, 3000 sec) prior to quenching in 30 µL of 0.5% formic acid, 2 M GuHCl, 0° C. These functionally deuterated samples are then subjected to DXMS processing, along with control samples of undeuterated and fully deuterated protein (incubated in 0.5% formic acid in 95% $D_2O$ for 24 hours at room temperature). The centroids of probe peptide isotopic envelopes are then measured using appropriate software. In order to obtain the deuteration levels of each peptide corrected to the values after "on-exchange" incubation, but before DXMS analysis, the corrections for back-exchange are made employing the methods of Zhang and Smith as previously described.

Regardless of the manner of sample preparation, quenched samples are then automatically directed to the "proteolysis" module (for methods employing progressive proteolysis fragmentation), or alternatively the "endopeptidase proteolysis" module (C) (for methods employing improved proteolysis fragmentation), in which proteolysis is accomplished using a battery of solid-state protease columns, variously pepsin, fungal protease XIII, newlase, etc. as desired, with the resulting peptide fragments being collected on a small reversed-phase HPLC column, with or without the use of a small c18 collecting pre-column. This column(s) is then acetonitrile gradient-eluted, with optional additional post-LC on-line proteolysis. The effluent is then directed to the electrospray head of the mass spectrometer (a Finnegan ion trap or a Micromass Q-TOF) which protrudes into a hole drilled in the side of the refrigerator. Several components of this module lend themselves to microfluidic devices as described earlier.

In a preferred embodiment, the proteolysis module contains four high pressure valves (Rheodyne 7010); with valve 1 bearing a 100 µL sample loop; valve 2 bearing a column (66 µl bed volume) packed with porcine pepsin coupled to perfusive HPLC support material (Upchurch Scientific 2 mm×2 cm analytical guard column; catalog no. C.130B; porcine pepsin, Sigma catalog no. p 6887, coupled to Poros 20 AL media at 40 mg/mL, in 50 mM sodium citrate, pH 4.5, and packed at 9 mL/min according to manufacturer's instructions); valve 3 bearing a C18 microbore (1 mm×5 cm) reversed phase HPLC column (Vydac catalog no. 218MS5105), and valve 4 connected to the electrospray head of a mass spectrometer. Inline filters (0.05 um, Upchurch catalog no. A.430) are placed on each side of the pepsin column, and just before the C18 column (Vydac prefilter, catalog no. CPF 10) to minimize column fouling and carryover from aggregated material.

In this configuration, four HPLC pumps (Shimadzu LC-10AD, operated by a Shimadzu SCL-10A pump controller) supplied solvents to the valves; with pumps C and D providing 0.05% aqueous TFA to valve 1 and valve 2 respectively; pumps A (0.05% aqueous TFA) and B (80% acetonitrile, 20% water, 0.01% TFA) are connected through a microvolume mixing tee (Upchurch catalog no. P. 775) to provide valve 3 with the C18 column-eluting gradient. All valves are connected to Two-Position Electrical Actuators (Tar Designs Inc.).

A typical sample is processed as follows: a 20 µL of hydrogen exchanged protein solution is quenched by shifting to pH 2.2-2.5, 0° C. with a 30 µL of quenching stock solution chilled on ice. The quenched solution is immediately pulled into the sample loading loop of valve 1, and then the computer program (see below) started. Pump C flow (0.05% TFA at 200 µL/min) pushes the sample out of injection loop onto the C18 HPLC column via the solid-state pepsin column at valve 2 (digestion duration of about 26 seconds). After two minutes of pump C solvent flow, the C18 column is gradient-eluted by pumps A and B (linear gradient from 10 to 50% B over 10 minutes; 50 µL/min; pumps A, 0.05% TFA; pump B, 80% acetonitrile, 20% water, 0.01% TFA), with effluent directed to the mass spectrometer. During data acquisition, pump D (aqueous 0.05% TFA 1 mL/min, 10 minutes) back-flushes the pepsin column to remove retained digestion products.

The timing and sequence of operation of the foregoing DXMS fluidics may be controlled by a personal computer running a highly flexible program in which sequential commands to targeted solid state relays can be specified, as well as variably timed delays between commands, as illustrated in the "DXMS Data Acquisition Control Module" (D). Certain command lines may access an array matrix of on- and off-exchange times, and the entire sequence of commands may be set to recycle, accessing a different element of the array with each cycle executed. Certain command lines may be set to receive "go" input signals from peripherals, to allow for peripheral-control of cycle progression. A library of command sequences may be prepared, as well as a library of on/off time arrays. An exemplary protein machine program can be configured to execute a supersequence of command sequence-array pairs.

An exemplary protein machine program (written in LabView I, National Instruments, Inc) controls the state(s) of a panel of solid-state relays on backplanes (SC-206X series of optically isolated and electromechanical relay boards, National Instruments, Inc.) with interface provided by digital input/output boards (model no. PCI-DIO-96 and PCI-6503, with NI-DAQ software, all from National Instruments, Inc.). The solid-state relays in turn exert control (contact closure or TTL) over pumps, valve actuators, and mass spectrometer data acquisition. Each of these peripherals are in turn locally programmed to perform appropriate autonomous operations when triggered, and then to return to their initial conditions. The autosampler and HPLC column pump controller are independently configured to deliver a "proceed through delay" command to the Digital I/O board as to insure synchronization between their subroutines and the overall command sequence.

In order to optimize or "tune" endopeptidase proteolysis, preliminary proteolytic "tuning" studies are performed to establish the fragmentation conditions (compatible with slowed exchange) optimal for peptide generation from the target polypeptide. Two major parameters that are often optimized are the concentration of GuHCl in quenching buffer and the pump C flow rate over the pepsin column. Typically, a 1 ml stock solution of protein (10 mg/ml, pH 7.0) is diluted with 19 mL of water and then quenched with 30 mL of 0.5% formic acid containing various concentrations of GuHCl (0-6.4 M). The quenched sample is then pulled into the sample loading loop, and the DXMS program sequence triggered immediately after sample loading. The flow over the pepsin column is varied (100 µL/min-300 µL/min) to adjust the duration of proteolytic digestion.

In order to quickly identify pepsin generated peptides for each digestion condition employed, spectral data is preferably acquired in particular modes, for example designated herein as "triple play" and "standard double play" modes, which have been empirically tuned to optimize the number of different parent ions upon which MS2 is performed. This data is then analyzed by appropriate software.

Triple play contains three sequentially executed scan events; first scan, MS1 across 200-2000 m/z; second scan, selective high resolution "zoom scan" on most prevalent peptide ion in preceding MS1 scan, with dynamic exclusion of parents previously selected; and third scan, MS2 on the same parent ion as the preceding zoom scan. The triple play data set or double play data set is then analyzed employing the Sequest software program (Finnigan Inc.) set to interrogate a library consisting solely of the amino acid sequence of the protein of interest to identify the sequence of the dynamically selected parent peptide ions.

This tentative peptide identification is verified by visual confirmation of the parent ion charge state presumed by the Sequest program for each peptide sequence assignment it made. This set of peptides is then further examined to determine if the "quality" of the measured isotopic envelope of peptides was sufficient (adequate ion statistics, absence of peptides with overlapping m/z) to allow accurate measurement of the geometric centroid of isotopic envelopes on deuterated samples.

According to an additional aspect of the present invention, it may be useful to perform in vivo analysis of a polypeptide of interest, for example, in situ analysis of protein-binding partner interactions. In such applications, the protein, while present in its native environment as a component of an intact living cell, or as a component of a cellular secretion such as blood plasma, is on-exchanged by incubating cells or plasma in physiologic buffers supplemented with tritiated or deuterated water. Optionally, the binding partner is then added, allowed to complex to the cell or plasma-associated protein, and then off-exchange initiated by returning the cell or plasma to physiologic conditions free of tritiated or deuterated water. During the off-exchange period (hours to days) the formed protein or complex is isolated from the cell or plasma by any purification procedure which allows the protein or complex to remain continuously intact. At the end of the appropriate off-exchange period, fragmentation and analysis of purified protein or complex proceeds as above. This analytic method is especially appropriate for proteins which lose substantial activity as a result of purification, as binding sites may be labeled prior to purification.

It is possible, also, to directly label the binding partner with deuterium and the binding protein with tritium. As a result, both the binding site and allosterically buried amides of the binding protein will be tritiated, but only binding site amides will be deuterated.

The indirect method is especially applicable to study of proteins which undergo substantial conformational changes after, or in the course of binding, such as insulin and its receptor.

According to further aspects of the present invention, after determining the binding sites of a binding protein or a binding partner, by the present methods (alone or in conjunction with other methods), the information may be exploited in the design of new diagnostic or therapeutic agents. Such agents may be fragments corresponding essentially to said binding sites (with suitable linkers to hold them in the proper spatial relationship if the binding site is discontinuous), or to peptidyl or non-peptidyl analogues thereof with similar or improved binding properties. Alternatively, they may be molecules designed to bind to said binding sites, which may, if desired, correspond to the paratope of the binding partner.

The diagnostic agents may further comprise a suitable label or support. The therapeutic agents may further comprise a carrier that enhances delivery or other improves the therapeutic effect.

The agents may present one or more epitopes, which may be the same or different, and which may correspond to epitopes of the same or different binding proteins or binding partners.

Alternative embodiments of the present invention are apparent to one of skill in the art. The following embodiments are intended to provide additional useful applications of the crystallography methods of the present invention.

According to another aspect of the present invention, there are provided methods of refining a crystallographic structure determination of a protein of interest, said methods comprising comparing an initial crystallographic structure determined using crystal(s) of said protein to at least one other crystallographic structure determined using crystal(s)

of at least one agent-modified form of said protein, wherein said agent-modified form(s) of said protein is(are) obtained by hydrogen exchange analysis.

According to yet another aspect of the present invention, there are provided methods of crystallization of a protein of interest, said methods comprising comparing an initial hydrogen exchange stability map of said protein to at least one other hydrogen exchange stability map of at least one agent-modified form of said protein, wherein said agent-modified form(s) of said protein is(are) obtained by identifying and agent-induced structuring of initially unstructured regions of said protein, and subjecting to crystallization one or more agent-modified form(s) of said protein exhibiting an improved hydrogen exchange stability map.

According to another aspect of the present invention, there are provided methods of crystallographic structure determination of a protein of interest, said methods comprising comparing an initial hydrogen exchange stability map of said protein to at least one other hydrogen exchange stability map of at least one agent-modified form of said protein, wherein said agent-modified form(s) of said protein is(are) obtained by identifying and deleting unstructured regions of said protein, and subjecting to crystallization and structure determination one or more agent-modified form(s) of said protein exhibiting an improved hydrogen exchange stability map.

The stability map of a protein of interest is defined by structured and unstructured regions of the protein, based on information obtained by the hydrogen exchange analysis performed on the protein. In a comparative sense, an improved stability map or profile is present when the number of unstructured regions or residues is decreased as compared to the original protein. Optionally, the hydrogen exchange stability maps of agent-modified forms of the protein are also compared to the original protein to identify those agent-modified forms that have an improved stability and have preserved the three-dimensional structure of the retained regions of the parent protein. FIG. 3 path 3 shows an exemplary use of comparative hydrogen exchange stability maps to identify unstructured regions and then identify agents that can induce structure in them, for subsequent co-crystallization analysis.

The invention will now be described in greater detail by reference to the following non-limiting examples.

EXAMPLE 1

Rapid Refinement of Crystallographic Protein Construct Definition Employing Enhanced Hydrogen/Deuterium Exchange Mass Spectrometry (DXMS)

Introduction

It is widely anticipated that access to high-resolution protein structures will be facilitated by novel high-throughput improvements to conventional crystallographic methods. Proteome-wide crystallography is one avenue being pursued by several groups, including the Joint Center for Structural Genomics (JCSG) (Lesley, et al. Proc Natl Acad Sci USA 99:11664-9. 2002, Stevens, et al. Science 293:519-520 2001, Stevens, et al. Science 294:89-92 2001). These efforts have benefited greatly from recent technology enhancements in protein expression and crystallization. Despite these enhancements, production of stable proteins that produce suitable crystals continues to be a serious bottleneck. Many generally well-structured proteins contain disordered regions that may serve as passive linkers between structurally autonomous domains, or become ordered when they interact with binding partners that provide stabilizing atomic contacts (Wright, et al. Journal of Molecular Biology 293:321-331 1999). Regardless of their function, unstructured regions can inhibit crystallization. Unstructured regions of proteins are also particularly susceptible to contaminating cellular proteases. Removing disordered regions may improve homogeneity. The energetics and kinetics of protein crystallization may be facilitated by selective deletion of unstructured sequences (Kwong, et al. J. Biol. Chem. 274:4115-4123 1999). Even those proteins that readily crystallize can suffer from poor diffraction, and it is likely that disorder plays a significant role. Truncated constructs should result in better diffraction and, consequently, result in higher resolution data more amenable to automated map fitting procedures (Cohen, et al. Protein Science 4:1088-1099 1995, Lamzin, et al. Nature Structural Biology Nov. 7, 2000, Supplement:978-981 2000).

In principle, information regarding protein dynamics could be used to design truncations that retain structure and maintain biological function but are otherwise depleted of disordered regions. A number of approaches ranging from stability-dependent protein expression screens to computation of stability from primary structure have been reported (Dunker, et al. Pac. Symp. Biocomput. 3:473-484 1998, Gamer, et al. Genome Inform. 9:201-214 1998, Romero, et al. Pac. Symp. Biocomput. 3:437-448 1998). For structural genomics studies, many targets have unknown folds, which limits the utility of bioinformatic predictions. NMR spectroscopy is one of the most powerful techniques to provide protein dynamics information, however, protein quantity, concentration, experimental time, and size are often limiting factors. Though limited proteolysis coupled to mass spectrometry is a preferred approach, its use is time consuming, frequently requiring that multiple proteolytic reactions be refined for optimal cleavage (Cohen, et al. Protein Science 4:1088-1099 1995). Interpretation of limited proteolysis results is confounded by the possibility that proteolysis may clip internal loops, leading to destabilization and further proteolytic degradation of what originally was a structured region. Most importantly, there is no facile method to confirm that the truncations designed have retained the stable elements of the full-length protein. These approaches are problematic in structural genomics efforts, where throughput and cost are dominating considerations (Chen, et al. Protein Science 7:2623-2630 1998).

For more than 40 years, peptide amide hydrogen-exchange techniques have been employed to study the thermodynamics of protein conformational change and the mechanisms of protein folding (Englander, et al. Methods Enzymol. 232:26-42 1994, Bai, et al. Methods Enzymol. 259:344 1995). More recently, they have proven to be increasingly powerful methods by which protein dynamics, domain structure, regional stability and function can be studied (Englander, et al. Protein Science 6:1101-9 1997, Engen, et al. Analytical Chemistry 73:256A-265A 2001). Deuterium exchange methodologies coupled with Liquid Chromatography Mass Spectrometry (LCMS) presently provide the most effective approach to study exchange rates in proteins (Engen, et al. Analytical Chemistry 73:256A-265A 2001). Proteolytic and/or collision-induced dissociation (CID) fragmentation methods allow exchange behavior to be mapped to subregions of the protein (Engen, et al. Analytical Chemistry 73:256A-265A 2001, Hoofnagle, et al. Proceedings, National Academy of Sciences 98:956-961 2001, Resing, et al. J. Am Soc Mass Spectrom 10:685-702 1999, Mandell, et al. Anal. Chem. 70:39487-3995 1998, Mandell, et al. Proc Natl Acad Sci USA 95:14705-10. 1998, Mandell, et al. J. Mol. Biol. 306:575-589 2001, Kim, et al. J Am Chem Soc 123:9860-6. 2001, Kim, et al. Biochemistry 40:14413-21. 2001, Zhang, et al. Protein Sci 10:2336-45. 2001, Kim, et al. Protein Sci 11:1320-9. 2002, Peterson, et al. Biochem J 362:173-81. 2002, Yan, et al. Protein Sci 11:2113-24. 2002). Building upon the pioneering work of Englander and Smith (Englander, et al. Protein Science 6:1101-9 1997, Engen, et al. Analytical Chemistry 73:256A-265A 2001, Smith, et al. J. Mass Spectrometry 32:135-146 1997), the present invention has developed and implemented a number of improvements which have significantly improved throughput, comprehensiveness, and resolution. The methods employing these enhancements high-throughput and high-resolution have been termed Deuterium Exchange-Mass Spectrometry (DXMS) (Hamuro, et al. J. Mol. Biol. 323:871-881 2002, Hamuro, et al. J. Mol. Biol. 4:703-714 2002, Woods-Jr., et al. Journal of Cellular Biochemistry 37:89-98 2001, Hamuro, et al. J. Mol. Biol. 327:1065-1076 2003, Woods-Jr. U.S. Pat. No. 5,658,739. 1997, Woods-Jr. U.S. Pat. No. 6,291,189 2001, Woods-Jr. U.S. Pat. No. 6,331,400 2001, Woods-Jr. U.S. Pat. No. 6,599,707. 2003, Zawadzki, et al. Protein Sci 12:1980-90 2003, Englander, et al. Proc. Nat. Acad. Sci. 100:7057-7062 2003).

Peptide amide hydrogens are not permanently attached to proteins, but reversibly interchange with hydrogen present in solvent water. The chemical mechanisms of the exchange reactions are understood, and several well-defined factors can profoundly alter exchange rates (Englander, et al. Methods Enzymol. 232:26-42 1994, Englander, et al. Anal. Biochem. 147:234-244 1985, Englander, et al. Methods Enzymol. 26:406-413 1972, Englander, et al. Methods Enzymol. 49G:24-39 1978). One of these factors is the extent to which a particular exchangeable hydrogen is exposed (accessible) to water. In a completely unstructured polypeptide sequence, peptide amide hydrogens are always maximally accessible to water and exchange at their maximal rate, which is approximately (within a factor of 30) the same for all amides; their half-life of exchange is in the range of one second at 0° C. and pH 7.0 (Molday, et al. Biochemistry 11:150 1972, Bai, et al. Proteins: Structure, Function, and Genetics 17:74-86 1993). Most amide hydrogens in structured peptides or proteins exchange much more slowly (up to $10^9$-fold reduction), reflecting the fact that exchange occurs only when transient unfolding fluctuations fully expose the amides to solvent water. The exception is the set of very fast exchanging amides in structured regions that have their amides fully solvent-exposed at all times, reflecting their protein-surface disposition. In effect, each amide's exchange rate in a native protein directly and precisely reports solvent accessibility to it, thereby revealing the protein's thermodynamic stability on the scale of individual amino acids. Measurement of the exchange rates of a protein's amides can therefore allow direct identification and localization of structured/unstructured regions of the protein; unstructured regions are those where substantial contiguous stretches of primary sequence exhibit the maximal possible exchange rates, indicative of complete and continuous solvation of the amide hydrogens in such segments (Englander, et al. Methods Enzymol. 232:26-42 1994, Bai, et al. Methods Enzymol. 259:344 1995). With its high-throughput capabilities, DXMS can rapidly localize disorder within crystallographic targets using a minimum of protein sample.

One aspect of the present invention focuses on proteins from *Thermotoga maritima* (Lesley, et al. Proc Natl Acad Sci USA 99:11664-9. 2002). An unbiased set of *T. maritima* targets, 1376 of the 1877 predicted open reading frames, were processed through expression and purification attempts. Of these, 542 proteins were expressed in soluble form and setup for crystallization trials with 434 resulting in preliminary crystal hits. This large dataset provides the basis to select proteins for DXMS analysis based on their propensity to crystallize. To sharply focus this analysis, a subset of *T. maritima* proteins selected for their range of known crystallization behavior were investigated. The methods of the present invention use DXMS to improve crystallographic construct design under high-throughput conditions.

Protein Expression and Purification

Twenty-four *T. maritima* proteins were selected for analysis (see Table 1 below). These proteins, and the subsequently designed truncated constructs, were freshly prepared for this study as previously described (Lesley, et al. Proc Natl Acad Sci USA 99:11664-9. 2002). In brief, all targets were expressed in either *E. coli* DL41 or HK100 from plasmids based on the expression vector pMH1 or pMH4. These vectors encode a 12 amino acid tag containing the first 6 amino acids of thioredoxin and 6 His residues placed at the N-terminus. Expression was induced by the addition of 0.15% arabinose for 3 hours. Bacteria were lysed by sonication, cell debris pelleted, and proteins purified from the soluble fraction by nickel chelate chromatography. Proteins were concentrated to a final volume of 0.75 μl with concentrations ranging from 15 to 50 mg/ml in 20 mM TrisHCl, pH8.0 with 150 mM NaCl (Lesley, et al. Proc Natl Acad Sci USA 99:11664-9. 2002).

Establishment of Protein Fragmentation Probe Maps

Aliquots of each of the 24 proteins were adjusted to a concentration of 10 mg/ml in Tris-Buffered Saline (5 mM Tris, 150 mM NaCl, pH 7.0; TBS), and all subsequent steps performed at 0° C. on melting ice. In a 4° C. cold room, five ill of each solution was further diluted with 15 μl of TBS in a microtiter plate employing multichannel pipettors for simultaneous manipulation. Thirty microliters of a stock "exchange quench" solution (0.8% formic acid, 1.6 M GuHCl) was then added to each sample (final concentration 0.5% formic acid, 1.0 M GuHCl), samples transferred to autosampler vials, and then frozen on dry ice within one minute after addition of quench solution as previously described (Hamuro, et al. J. Mol. Biol. 323:871-881 2002, Hamuro, et al. J. Mol. Biol. 4:703-714 2002, Woods-Jr., et al. Journal of Cellular Biochemistry 37:89-98 2001, Hamuro, et al. J. Mol. Biol. 327:1065-1076 2003, Woods-Jr. U.S. Pat. No. 5,658,739. 1997, Woods-Jr. U.S. Pat. No. 6,291,189 2001, Woods-Jr. U.S. Pat. No. 6,331,400 2001, Woods-Jr. U.S. Pat. No. 6,599,707. 2003, Zawadzki, et al. Protein Sci 12:1980-90 2003, Englander, et al. Proc. Nat. Acad. Sci. 100:7057-7062 2003). Vials with frozen samples were stored at −80° C. until transferred to the dry ice-containing sample basin of the cryogenic autosampler module of a DXMS analysis apparatus designed and operated as previously described (Hamuro, et al. J. Mol. Biol. 327:1065-1076 2003, Zawadzki, et al. Protein Sci 12:1980-90 2003, Englander, et al. Proc. Nat. Acad. Sci. 100:7057-7062 2003). In brief, samples were melted at 0° C., proteolyzed for 16 seconds by exposure to immobilized pepsin, fragments collected on a c18 HPLC column, with subsequent acetonitrile gradient elution. Column effluent was analyzed on both a Thermo Finnigan LCQ electrospray mass spectrometer and a Micromass Q-T of mass spectrometer, as previously described (Hamuro, et al. J. Mol. Biol. 323:871-881 2002, Hamuro, et al. J. Mol. Biol. 4:703-714 2002, Woods- Jr., et al. Journal of Cellular Biochemistry 37:89-98 2001, Hamuro, et al. J. Mol. Biol. 327:1065-1076 2003, Woods-Jr. U.S. Pat. No. 6,599,707. 2003, Zawadzki, et al. Protein Sci 12:1980-90 2003, Englander, et al. Proc. Nat. Acad. Sci. 100:7057-7062 2003). The Sequest software program (Thermo Finnigan Inc) identified the likely sequence of the parent peptide ions and these tentative identifications were confirmed with specialized DXMS data reduction software as previously described (Hamuro, et al. J. Mol. Biol. 327: 1065-1076 2003, Zawadzki, et al. Protein Sci 12:1980-90 2003, Englander, et al. Proc. Nat. Acad. Sci. 100:7057-7062 2003).

On-exchange Deuteration of Proteins

After establishment of fragmentation maps for each protein, amide hydrogen exchange-deuterated samples of each of the 24 proteins were prepared and processed exactly as above, except that 5 µl of each protein stock solution was diluted with 15 µl of Deuterium Oxide ($D_2O$) containing 5 mM Tris, 150 mM NaCl, pD (read) 7.0, and incubated for ten seconds at 0° C. on melting ice before quench and further processing. Data on the deuterated sample set were acquired in a single automated 30-hour run and subsequent data reduction performed with the DXMS software. Corrections for loss of deuterium label were made as previously described. (Hamuro, et al. J. Mol. Biol. 327:1065-1076 2003, Zawadzki, et al. Protein Sci 12:1980-90 2003, Englander, et al. Proc. Nat. Acad. Sci. 100:7057-7062 2003). The total time elapsed for data acquisition and analysis (both fragmentation maps and deuteration study) was two weeks. A total of 100 µg of each protein was used to complete the study. For subsequent comparative analysis of the exchange rates of amide hydrogens within truncated protein constructs versus their full-length forms, both proteins were contemporaneously on-exchanged as above, but quenched at varying times (10, 30, 100, 300, 1000, 3000, 10,000, and 30,000 seconds), and further processed as above, employing the fragmentation maps established for the full-length protein.

Protein Crystallization and Diffraction Data Acquisition

Proteins were crystallized using the vapor diffusion method with 50 nl or 250 nl protein and 50 nl or 250 nl mother liquor respective volumes as sitting drops on customized 96 well microtiter plates (Greiner). Each protein was setup using 480 standard crystallization conditions (Wizard I/II, Wizard Cryo I/II [Emerald Biostructures], Core Screen I/II, Cryo I, PEG ion, Quad Grid [Hampton Research]) at 4° and 20° C. Images of each crystal trial were taken at least twice, typically at 7 and 28 days after setup with an Optimag Veeco Oasis 1700 imager. Each image was evaluated using a crystal detection algorithm and scored for the presence of crystals (Spraggon, et al. Acta. Cryst. D. 58:1915-1923 2002). Images at days 7 and 28 were also evaluated manually. Diffraction data were provided by the JCSG from automated data collection at 100K on beamlines of the SSRL Structural Molecular Biology/Macromolecular Crystallography Resource, and the Advanced Light Source beamlines 5.0.2 and 5.0.3 as described previously (Lesley, et al. Proc Natl Acad Sci USA 99:11664-9. 2002).

DXMS Defines Rapidly-exchanging Regions of T. maritima proteins

In DXMS analysis, fragmentation parameters are initially optimized, including denaturant (GuHCl) concentration, protease type(s), proteolysis duration to maximize the number of peptide fragment probes available for use with the target protein, and then the protein is examined using a broad range of on-exchange times. This approach optimizes the ability to measure the widely ranging exchange rates for most of the peptide amides in the protein (Hamuro, et al. J. Mol. Biol. 323:871-881 2002, Hamuro, et al. J. Mol. Biol. 4:703-714 2002, Woods-Jr., et al. Journal of Cellular Biochemistry 37:89-98 2001, Hamuro, et al. J. Mol. Biol. 327:1065-1076 2003, Woods-Jr. U.S. Pat. No. 6,599,707. 2003, Zawadzki, et al. Protein Sci 12:1980-90 2003, Englander, et al. Proc. Nat. Acad. Sci. 100:7057-7062 2003). In the methods of the present invention, only disordered amides that exchanged very fast in the native protein were localized. Based on prior experience, a single set of fragmentation conditions was employed and on-exchanged samples for a single, brief (10 seconds, 0° C.) interval to selectively label only the most rapidly exchanging amides.

Generation of fragmentation maps and acquisition and analysis of deuteration data were completed in two weeks time for 24 samples. Fragmentation maps covering the entire protein sequence were obtained for sixteen proteins, nearly complete coverage for five proteins, and inadequate coverage for three proteins (see Table 1 below). Deuterium on-exchange studies were performed on the 21 proteins that had generated useful fragmentation maps (see FIG. 4). Deuterium labeling was manually assigned to residue positions within the protein by first optimizing consensus in deuterium content of overlapping peptide probes, followed by further clustering of labeled amides together in the center of unresolved regions, so that a consensus map was generated. The deduced 10 second exchange maps for each of the 21 proteins, and their consensus maps are summarized in FIG. 8.

The duration of labeling (10 seconds) was calculated to be sufficient to selectively deuterate primarily freely-solvated amides (Molday, et al. Biochemistry 11:150 1972, Bai, et al. Proteins: Structure, Function, and Genetics 17:74-86 1993). This was confirmed by first fragmenting reference proteins with pepsin to yield unstructured peptides, followed by deuterium-exchange labeling of the resulting peptide mix for 10 seconds at pH 7.0, 0° C. as above and, then, quenching and subjecting the mixture to DXMS analysis, but without repeated proteolysis. Under these conditions, all peptides were saturation-labeled with a 10 second period of on-exchange.

DXMS Correctly Localizes Disordered Regions in Control Proteins with Known 3-D Structures Interpretation of the exchange maps of the T. maritima proteins was guided by the expectation of two patterns of fast exchange labeling: structurally stable, but well solvated, rapidly exchanging residues (one to three contiguous residues) versus labeling of longer stretches of sequence (four or more residues) indicative of disorder. It was presumed that three contiguous amino acids was likely the smallest number needed to complete a structurally stable turn on the surface of a protein. The percent of each protein's residues that rapidly labeled in stretches of four or more residues is indicated as "DXMS %" in Table 1.

The structure of T. maritima thy1 protein TM0449 has been determined to 2.25 Å (Mathews, et al. Structure 11:677-690 2003). Its exchange map demonstrated two segments ($\geq 4$ residues in each) with rapid exchange, labeled A (Phe 31-Glu 38) and B (Ser 88-Lys 93), and several isolated rapidly exchanging amides in groups of 3 or less, scattered throughout the sequence (see FIG. 5). Both of the rapidly-exchanging segments corresponded closely to regions of disorder in the crystal (Phe 32-Glu 38 and Ser 89-Ser 94, FIG. 5) confirming the ability of DXMS data to detect and localize such disordered regions. Interestingly, these regions also appear to be involved in the binding of the enzyme substrate and adopt a structured conformation after binding ligand (Mathews, et al. Structure 11:677-690 2003). This suggests that DXMS can also provide some localized prediction of substrate and cofactor binding sites. This raises the caution that even focused deletion of unstructured regions always carries the potential to remove regions critical to biological function. Similar comparisons were performed for other proteins with known structures (data not shown) with regions of internal disorder typically mapping to loop or extended solvent-accessible regions.

Poorly Crystallizing *T. maritima* Proteins Contain Substantial Disorder

The exchange map for *T maritima* GroES heat shock protein TM0505 demonstrated rapid exchange for three segments containing four or more contiguous rapidly-exchanging residues, which together constitute 16% of its sequence (FIG. 6). While this *T. maritima* protein had previously produced only poorly diffracting crystals, it is a close homolog of the GroES heat shock protein of *M. tuberculosis*, for which crystal structures were available as the GroES heptamer, and as a complex (GroELS) with the GroEL subunit (Ranson, et al. Cell 107:869-879 2001, Roberts, et al. J. Bacteriol. 185:2003). When the *T. maritima* residues with rapid exchange are mapped on the *M. tuberculosis* structures, they predominantly localize to disordered residues in GroES that make contact with the GroEL binding surface (FIG. 7).

The exchange map for the conserved hypothetical protein TM1816 is dominated by several substantial regions of disorder, constituting 17.7% of its residues. This protein was a unique example where a structure was obtained from a target exhibiting substantial disorder. The poorly crystallizing proteins TM1171, TM0160, TM1706, TM1733 and TM1079 exhibit, for substantial portions of their sequence, rapidly exchanging stretches of 4 or more residues (13.9%, 12.1%, 11.5%; 6.6% and 5.7% respectively). TM0160, TM1171, and TM1172 had disorder primarily at the carboxy-terminus; (See FIG. 8A-E).

Disorder-depleted Constructs of *T. maritima* Proteins Preserve Ordered Structure.

Truncation mutants of TM0160 and TM1171 proteins were prepared in which the carboxy-terminal disordered region(s) of both proteins were deleted. The fragmentation patterns produced by pepsin often exhibited preferences for sites near exchange-defined stretches of disorder. Several truncated constructs to each full-length protein were produced, in part guided by the location of the "preferred" pepsin cut sites, and for both TM0160 and TM1171. Deletions were designed solely on the basis of DXMS experimental data. The truncations expressed well as a soluble protein. Full-length TM0160, and its longest truncated version were on-exchanged variously for 10, 100, 1,000, and 10,000 seconds at 0° C. on ice, exchange-quenched and subjected to comparative DXMS analysis as described above. The resulting 10-second exchange maps for full-length protein and the D3 truncated version had virtually identical 10 second patterns, and detailed analysis of the longer exchange times demonstrated that D3 had a stability profile identical to that of the TM0160 full-length. Similarly, each of the four TM1171 truncated constructs expressed well as soluble protein, and had DXMS stability maps identical to that of the TM1171 full-length protein in the corresponding sequence regions.

Deletion Constructs of Two *T. maritima* Proteins Show Marked Improvement in Crystallization Full-length TM0160 and the truncation were submitted for crystallization trials (Table 1). A total of 480 commercially available crystallization solutions were screened at 4° C. and 20° C. as described herein. From multiple protein preparations and crystallization attempts the full-length protein showed marginal crystals (inadequate for diffraction experiments) for only 3 of 2400 total attempts. In contrast using the same 480 crystallization solutions, 76 crystal hits were obtained for the truncated constructs from 1920 attempts. Crystals from the TM0160 D3 truncation mutant had better morphology than did the few crystals obtained with the full-length construct and diffracted well. Ultimately, a 1.9 Å dataset from selenomethionine-incorporated protein enabled determination of the TM0160 3-dimensional structure, which represents a novel fold (to be presented elsewhere). Similarly, the TM1171 and truncations were subjected to crystallization trials. Whereas the TM1171 full-length protein again showed very marginal crystallization propensity (5 out of 2400 attempts), each of the four TM1171 deletion constructs showed marked improvement in crystallization success with the TM1171-D4 construct ultimately resulting in a 2.1 Å dataset that was used to determine its 3-dimensional structure (to be presented elsewhere). It should be noted that well-diffracting crystals were obtained for DXMS-designed deletion constructs in both native and selenomethionine forms.

Table 1. Description of *T. maritima* proteins studied, as classified by crystallization history. Computational predictions (SEG %) and the portion of each protein's sequence found to be present in high-exchange rate stretches of primary sequence (four or more rapidly exchanging contiguous residues; DXMS %) are given as a percentage of total residues. The primary location of the DXMS-identified rapidly-exchanging regions is indicated. The number of unique crystallization tests is indicated along with the number of tests showing crystal hits or crystals of sufficient size to mount for diffraction screening. The percentage of total tests that led to crystals is indicated. Those targets showing less than a 1% hit rate are considered poorly crystallizing. The number of crystals screened for diffraction and the best resolution are indicated where data are available.

TABLE 1

| Target | Structure | SEG % | DXMS % | Location | Crystallization | | | | Diffraction | |
| --- | --- | --- | --- | --- | --- | --- | --- | --- | --- | --- |
| | | | | | Screened | Hit | Mountable | % Crystallized | Screened | Resolution (Å) |
| TM0665 | 1J6N | 11.2 | 3.1 | | 1920 | 247 | 244 | 25.6 | 7 | 2.2 |
| TM1056 | pending | 17.7 | 0.0 | | 175 | 153 | 9.8 | 45 | 1.8 | |
| TM0064 | 1J5S | 3.0 | 1.1 | | 2880 | 114 | 146 | 9.0 | 31 | 1.8 |
| TM1464 | pending | 10.1 | 1.3 | | 2400 | 71 | 98 | 7.0 | 68 | 2.6 |
| TM1080 | 1O1X | 3.9 | 2.6 | | 2400 | 119 | 26 | 6.0 | 32 | 3.5 |
| TM0449 | 1KQ4 | 2.6 | 6.4 | | 1152 | 42 | 16 | 5.0 | 16 | 2.3 |

TABLE 1-continued

| Target | Structure | SEG % | DXMS % | Location | Crystallization | | | | Diffraction | |
| | | | | | Screened | Hit | Mountable | % Crystallized | Screened | Resolution (Å) |
|---|---|---|---|---|---|---|---|---|---|---|
| TM0486 | | 5.7 | 0.0 | | 3552 | 139 | 29 | 4.7 | 13 | 3.9 |
| TM0542 | pending | 9.3 | 2.9 | | 2592 | 47 | 49 | 3.7 | 56 | 2.8 |
| TM1733 | | 10.0 | 6.6 | internal | 1920 | 33 | 22 | 2.9 | 29 | 3.4 |
| TM1158 | 1O1Y | 2.5 | 2.6 | | 2880 | 32 | 39 | 2.5 | 62 | 2.2 |
| TM0269 | 1J6R | 2.8 | 4.0 | | 4608 | 55 | 33 | 1.9 | 11 | 2.1 |
| TM1764 | | 29.3 | n.d. | | 480 | 4 | 2 | 1.3 | 0 | |
| TM1816 | 1O13 | 11.0 | 17.7 | internal | 2016 | 2 | 21 | 1.1 | 9 | 2.0 |
| TM0505 | | 21.1 | 16.3 | internal | 3744 | 12 | 10 | 0.6 | 8 | 6.3 |
| TM0212 | | 21.3 | 0.0 | | 1152 | 5 | 1 | 0.5 | 1 | 8.6 |
| TM0320 | | 30.4 | 0.0 | | 1152 | 4 | 1 | 0.4 | 0 | |
| TM1171 | | 10.3 | 13.9 | C-term | 4 | 1 | 0.2 | 0 | | |
| D1 | | 16.4 | 5.9 | | 2880 | 41 | 33 | 2.6 | 0 | |
| D2 | | 16.5 | 5.9 | | 2880 | 66 | 9 | 2.6 | 16 | 2.3 |
| D3 | | 15.3 | 5.6 | | 24 | 10 | 1.8 | 0 | | |
| D4 | pending | 14.9 | 5.6 | | 1920 | 12 | 14 | 1.4 | 1 | 2.1 |
| TM1706 | | 17.9 | 11.5 | internal | 1440 | 3 | 0 | 0.2 | 0 | |
| TM1172 | | 11.5 | 3.5 | C-term | 3 | 1 | 0.2 | 0 | | |
| TM0913 | | 7.5 | 2.2 | | 4320 | 5 | 2 | 0.2 | 0 | |
| TM1079 | | 16.3 | 5.7 | internal | 1920 | 3 | 0 | 0.2 | 0 | |
| TM1773 | | 10.4 | n.d. | | 1440 | 1 | 1 | 0.1 | 0 | |
| TM0160 | | 15.5 | 12.1 | C-term | 2 | 1 | 0.1 | 0 | | |
| D3 | pending | 11.6 | 2.5 | | 1920 | 37 | 39 | 4.0 | 3 | 1.9 |
| TM0855 | | 9.1 | n.d. | | 1920 | 0 | 0 | 0.0 | 0 | |

Discussion

These studies have shown that DXMS analysis can reliably detect and localize disordered regions within an otherwise structured protein. Stability profiles were determined for 21 *T. maritima* proteins that had previously been subjected to crystallization studies (Table 1). Twelve proteins crystallized readily in >1% of the conditions tested. Four of the remaining nine poorly-crystallizing proteins had a high fraction (>10%) of their sequence in disordered regions suggesting this as a potential cause of the poor behavior. Most importantly, present instrumentation allowed determination of the DXMS-protein stability profiles at speeds matching the needs of HT Structural Genomics.

The methods of the present invention have also established that successful strategies to selectively delete disorder from protein constructs can be readily discerned from DXMS stability profiles. Furthermore, the present invention shows that DXMS can rapidly and reliably assess the fidelity of preservation of full-length structure in truncations. While several bioinformatic approaches to construct design can be used with well-characterized protein folds, DXMS-guided construct redesign offers a particular advantage in the study of proteins that have novel folds. DXMS data directly localizes disorder to specific amino acid residues in the target protein regardless of overall fold structure, allowing greatly refined truncation definition. Unlike NMR methods, which can also provide exchange data, DXMS requires only microgram amounts of soluble protein and data acquisition and analysis can be performed in a rapid timescale. In the present investigation, the total time elapsed for data acquisition and analysis (both fragmentation maps and deuteration study) was two weeks, and a total of 100 μg of each protein was used.

Finally, these results establish that DXMS stability profile-guided construct design can produce derivatives of poorly crystallizing proteins that crystallize and diffract well. In each of two attempts, the methods described herein succeeded in producing diffraction quality crystals of truncated constructs of *T. maritima* full-length proteins that had behaved poorly in several crystallization attempts, and have confirmed that these truncations preserved full-length exchange rate patterns, indicating that they had retained full-length structure with high fidelity. Taken together, these results indicate that DXMS is a valuable tool for structural genomics efforts.

Supplemental Material

Sample Processing for Establishment of Protein Fragmentation Probe Maps

Vials with frozen samples were stored at −80° C. until transferred to the dry ice-containing sample basin of the cryogenic autosampler module of the DXMS apparatus. Samples were individually melted at 0° C., then injected (45 ul) and pumped through an immobilized pepsin column (0.05% TFA, 250 ul/min, 16 seconds exposure to pepsin; 66 μl column bed volume, coupled to 20AL support from PerSeptive Biosystems at 30 mg/ml). Pepsin-generated fragments were collected onto a C18 HPLC column, eluted by a linear acetonitrile gradient (5 to 45% B in 30 minutes; 50 μl/min; solvent A, 0.05% TFA; solvent B, 80% acetonitrile, 20% water, 0.01% TFA), and effluent directed to the mass spectrometer with data acquisition in either MS1 profile mode or data-dependent MS2 mode. Mass spectrometric analyses used a Thermo Finnigan LCQ electrospray ion trap type mass spectrometer operated with capillary temperature at 200° C. or an electrospray Micromass Q-Tof mass spectrometer, as previously described (Hamuro, et al. J. Mol. Biol. 323:871-881 2002, Hamuro, et al. J. Mol. Biol. 4:703-714 2002, Woods-Jr., et al. Journal of Cellular Biochemistry 37:89-98 2001, Hamuro, et al. J. Mol. Biol. 327:1065-1076 2003, Woods-Jr. U.S. Pat. No. 6,599,707. 2003, Zawadzki, et al. Protein Sci 12:1980-90 2003, Englander, et al. Proc. Nat. Acad. Sci. 100:7057-7062 2003). The Sequest software program (Thermo Finnigan Inc) identified the likely sequence of the parent peptide ions. Tentative identifications were tested with specialized DXMS data reduction software developed in collaboration with Sierra Analytics, LLC, Modesto, Calif. This software searches MS1 data for scans containing each of the peptides, selects scans with optimal signal-to-noise, averages the selected scans, calculates centroids of isotopic envelopes, screens for peptide misidentification by comparing calculated and known centroids, then facilitates visual review of each averaged isotopic envelope allowing an assessment of "quality" (yield, signal/noise, resolution), and confirmation or correction of peptide identity and calculated centroid (Hamuro, et al. J. Mol. Biol. 323:871-881 2002, Hamuro, et al. J. Mol. Biol. 4:703-714 2002, Woods-Jr., et al. Journal of Cellular Biochemistry 37:89-98 2001, Hamuro, et al. J. Mol. Biol. 327:1065-1076 2003, Woods-Jr. U.S. Pat. No. 6,599,707. 2003, Zawadzki, et al. Protein Sci 12:1980-90 2003, Englander, et al. Proc. Nat. Acad. Sci. 100:7057-7062 2003).

On-exchange Deuteration of Proteins

After establishment of fragmentation maps for each protein, amide hydrogen exchange-deuterated samples of each of the 24 proteins were prepared and processed exactly as above, except that 5 ul of each protein stock solution was diluted with 15 ul of Deuterium Oxide ($D_2O$), containing 5 mM Tris, 150 mM NaCl, pD (read)7.0, and incubated for ten seconds at 0° C. on melting ice before quench and further processing. Data on the deuterated sample set were acquired in a single automated 30-hour run, and subsequent data reduction performed on the DXMS software. Corrections for loss of deuterium-label by individual fragments during DXMS analysis (after "quench") were made through measurement of loss of deuterium from reference protein samples that had been equilibrium-exchange-deuterated under denaturing conditions as previously described (Hamuro, et al. J. Mol. Biol. 323:871-881 2002, Hamuro, et al. J. Mol. Biol. 4:703-714 2002, Woods-Jr., et al. Journal of Cellular Biochemistry 37:89-98 2001, Hamuro, et al. J. Mol. Biol. 327:1065-1076 2003, Woods-Jr. U.S. Pat. No. 6,599,707. 2003, Zawadzki, et al. Protein Sci 12:1980-90 2003, Englander, et al. Proc. Nat. Acad. Sci. 100:7057-7062 2003). The total time elapsed for data acquisition and analysis (both fragmentation maps and deuteration study) was two weeks, and a total of 100 ug of each protein was used to complete the study. The personnel performing the data acquisition and reduction part of the study were unaware of the identity or crystallization histories of the proteins while data were being acquired and processed. For subsequent comparative analysis of the exchange rates of amide hydrogens within truncated protein constructs vs. their full-length forms, both proteins were contemporaneously on-exchanged as above, but quenched at varying times (10, 30, 100, 300, 1000, 3000, 10,000, and 30,000 seconds), and further processed as above, employing the fragmentation maps established for the fill-length protein.

Equipment Configuration

The equipment configuration consisted of electrically-actuated high pressure switching valves (Rheodyne), connected to two position actuators from Tar Designs Inc., Pittsburgh, as described previously (Hamuro, et al. J. Mol. Biol. 323:871-881 2002, Hamuro, et al. J. Mol. Biol. 4:703-714 2002, Woods-Jr., et al. Journal of Cellular Biochemistry 37:89-98 2001, Hamuro, et al. J. Mol. Biol. 327:1065-1076 2003, Woods-Jr. U.S. Pat. No. 6,599,707. 2003, Zawadzki, et al. Protein Sci 12:1980-90 2003, Englander, et al. Proc. Nat. Acad. Sci. 100:7057-7062 2003). A highly agent-modified Spectraphysics AS3000 autosampler, partially under external PC control, employed a robotic arm to lift the desired frozen sample from the sample well, then automatically and rapidly melted and injected the sample under precise temperature control (Hamuro, et al. J. Mol. Biol. 323:871-881 2002, Hamuro, et al. J. Mol. Biol. 4:703-714 2002, Woods-Jr., et al. Journal of Cellular Biochemistry 37:89-98 2001, Hamuro, et al. J. Mol. Biol. 327:1065-1076 2003, Zawadzki, et al. Protein Sci 12:1980-90 2003, Englander, et al. Proc. Nat. Acad. Sci. 100:7057-7062 2003). The autosampler basin was further thermally insulated and all but 20 vial positions were filled with powdered dry ice sufficient to keep samples colder than −45° C. for 18 hours. Four HPLC pumps (Shimadzu LC-10AD) were operated by a Shimadzu SCL-10A pump controller. One produced forward flow over the pepsin column, another backflushed the protease column after sample digestion (0.05% aqueous TFA), and two delivered solvents to a downstream HPLC column for gradient elution (A: 0.05% aqueous TFA; B; 80% acetonitrile, 20% water, 0.01% TFA; 1×50 mm C18 Vydac # 218MS5105, pH 2.3). Valves, tubing, columns and autosampler were contained within a refrigerator at 2.8° C., with pepsin and HPLC columns immersed in melting ice. The timing and sequence of operation of the DXMS apparatus fluidics were controlled by a personal computer running an in-house written LabView-based program, interfaced to solid-state relays (digital input/output boards, National Instruments), controlling pumps, valve actuators, and MS data acquisition.

EXAMPLE 2

Stability of a Two Repeat Fragment of Chicken Brain α-Spectrin Probed at High Resolution by Enhanced Hydrogen/Deuterium Exchange Mass Spectrometry (DXMS): Implications for the Molecular Mechanisms of Spectrin Elasticity Spectrin is a cytoskeletal protein involved in maintaining structural support and membrane elasticity. It includes an α-monomer of 21 tandem repeats, with each repeat composed of three well-formed, long antiparallel α-helices connected by short turns or loops, forming a "z"-shaped three-helix bundle (Grum, et al. Cell 98:523-35. 1999). It functions, in part, as an elastic molecule, demonstrating a distinctive "sawtoothed" compliance behavior, where tension remains within a relatively narrow range despite considerable lengthening. To better understand the molecular basis of this behavior, the structural stability of α-spectrin is determined herein, at near-individual amino acid scale, with enhanced methods of peptide amide hydrogen-deuterium exchange-mass spectrometry. The behavior of a two repeat construct (R1617) of chicken brain a spectrin ($16^{th}$-$17^{th}$ repeats) for which the three dimensional structure has been determined crystallographically was determined.

The construct was incubated in D2O-containing buffer for varying times, to allow "on-exchange", with solvent-accessibility-dependent incorporation of deuterium into peptide amides, and then exchange-"quenched", to effectively lock exchanged deuterium in place. The deuterium-labeled protein was then enzymatically fragmented into a large number of sequence-overlapping peptides, and further processed by LCMS to quantify deuterium exchanged onto each peptide. This data was then computationally processed into peptide amide-specific exchange rates employing novel algorithms and software described herein. The result was the generation of an amide hydrogen exchange-rate profile from which the relative thermodynamic stability or "energetic landscape" of the molecule could be assessed at the individual residue level.

Remarkably, each of the six long helices in the construct was not a uniformly stable structure, but demonstrated gradients in hydrogen exchange rates, with amides in the middle ¼ to ⅓ portions of each helix having slow exchange rates, progressively increasing to more than 1000 times faster rates towards the ends of the helices. Additionally, the COREX algorithm was used to computationally estimate the exchange rates for the repeat from its crystal structure, and found these results to be in close agreement with the experimentally determined exchange rate profile, confirming the presence of pronounced α-helix stability gradients. Comparable helix stability gradients were not present in five other proteins.

These findings support and extend previous models of α-spectrin behavior that propose conformational rearrangements involving stretch-induced helix-loop transitions, with migration of the short loop regions back and forth along the helices. Results suggest that if this "loop-migration" model is operative in α-spectrin, then the loops will likely migrate into progressively more stable regions of the α-helices as α-spectrin is stretched, storing mechanical energy. This energy can be recovered when the molecule relaxes, and the loop migrates back into less stable regions of the helices.

Introduction

The cytoskeleton of blood cells includes many components necessary for maintaining membrane structural integrity and allowing the cells to withstand the large stresses of traversing the circulatory system. It includes tetramers of the elastic protein α-spectrin, which consists of an α-monomer of 21 tandem repeats and a beta-monomer of 16 repeats. X-ray crystal structures of constructs composed of two such tandem repeats of the α-subunit reveal that each is composed of three well-formed, long antiparallel α-helices connected by short turns or loops, forming a "z"-shaped three-helix bundle (Grum, et al. Cell 98:523-35. 1999), with the tandem repeats connected by a short α-helical "linker" region.

While v plays a critical role in the reversible deformation of the membrane, the molecular basis of this behavior, particularly its dynamic aspects, are unclear. Investigation of cloned repeats using chemical and thermal denaturation as well as atomic force microscopy (AFM) have yielded important advances in the understanding of the physical and biomechanical properties of unfolding and refolding of repeating units as well as the function of α-spectrin as a whole. Force-extension curves from AFM studies of have demonstrated that v is a highly non-linear spring with substantial relatively small peak unfolding forces (20-50 pN) per repeating unit. Other studies have also indicated that these repeats unfold independently and/or in tandem (Law, et al. Biophys J 84:533-44. 2003, Rief, et al. J Mol Biol 286:553-61. 1999) with the presence of intermediates (Altmann, et al. Structure (Camb) 10:1085-96. 2002). In AFM experiments α-spectrin demonstrates a distinctive "sawtoothed" compliance behavior, where tension rises only gradually, and remains within a relatively narrow range despite considerable lengthening of the molecule.

Several models, based on crystallization and/or atomic force microscopy studies, have been proposed to account for α-spectrin's elasticity, including tension-induced bending of the linker regions, tension-induced unwrapping or melting of the ends of α-helices into elongated loops; and catastrophic unfolding of triple helical bundles, in which the sawtoothed compliance observed is attributed to multiple tandem bundles sequentially popping open with increased tension.

A fourth mechanism has been proposed in which there is a tension-induced end-to-end lengthening of the triple helical bundles, resulting from stretch-induced migration of the short loop regions along the α-helices, accomplished by relatively little change in the total amount of helix in each bundle (Grum, et al. Cell 98:523-35. 1999). Observations presented herein support and extend this model.

Evaluation of these, and other proposed mechanisms for α-spectrin elasticity would be facilitated by a detailed characterization of the thermodynamic stability or "energetic landscape" of the α-spectrin molecule. To this end, its structural stability was probed at the individual amino acid scale employing enhanced methods of peptide amide hydrogen-deuterium exchange 1 c-mass spectrometry, termed DXMS. Peptide amide hydrogens are not permanently attached to a protein, but continuously and reversibly interchange with hydrogen present in water. The chemical mechanisms of the exchange reactions are understood, and several well-defined factors can profoundly alter exchange rates (Englander, et al. Methods Enzymol. 232:26-42 1994, Englander, et al. Anal. Biochem. 147:234-244 1985, Englander, et al. Methods Enzymol. 26:406-413 1972, Englander, et al. Methods Enzymol. 49G:24-39 1978). One of the factors that determines the rate of exchange is the extent to which a particular exchangeable hydrogen is exposed (accessible) to water. The exchange reaction proceeds efficiently only when a particular peptide amide hydrogen is fully exposed to solvent. Peptide amide hydrogens that are freely accessible to water exchange at their maximal possible rate, with an average half-life of exchange of approximately one second at 0° C. and pH 7.0. (Molday, et al. Biochemistry 11:150 1972, Bai, et al. Proteins: Structure, Function, and Genetics 17:74-86 1993). The precise rate of exchange of a particular fully-solvated amide can vary more than thirty-fold from this average rate, depending upon the identity of the two amino acids flanking the amide bond. Exact exchange rates expected for fully solvent-exposed amide hydrogens can be reliably calculated from knowledge of the temperature, pH and primary amino acid sequence involved (Molday, et al. Biochemistry 11:150 1972, Bai, et al. Proteins: Structure, Function, and Genetics 17:74-86 1993).

In a structured protein, most peptide amide hydrogens exchange slower (up to $10^9$-fold slower) than the maximal, fully solvated exchange rate, as they are not efficiently exposed to solvent water. Protein structure is not static, but best considered as an ensemble of transiently unfolded states: the native state ensemble. Amide hydrogen exchange occurs only when a particular transient unfolding event fully exposes an amide to solvent. The ratio of exchange rates for a particular amide hydrogen, in the folded vs random coil states is referred to as the exchange protection factor, and directly reflects the free energy change in the atomic environment of that particular hydrogen between unstructured and structured states of the protein. In this sense, amide hydrogens can be treated as atomic-scale sensors of highly localized free energy change throughout a protein and the magnitude of free energy change reported from each of a protein's amides in a folded vs. unfolded state is precisely equal to -RT ln (protection factor) (Bai, et al. Methods Enzymol. 259:344 1995). In effect, each peptide amide's exchange rate in a folded protein (when measured) directly and precisely reports the protein's thermodynamic stability at the individual amino acid scale (Englander, et al. Methods Enzymol. 232:26-42 1994, Bai, et al. Methods Enzymol. 259:344 1995).

Deuterium exchange methodologies coupled with Liquid Chromatography Mass Spectrometry (LCMS), presently provide the most effective approach to perform hydrogen exchange studies of proteins larger than 30 kDa in size (Engen, et al. Analytical Chemistry 73:256A-265A 2001) (Engen, et al. Analytical Chemistry 73:256A-265A 2001, Hoofnagle, et al. Proceedings, National Academy of Sciences 98:956-961 2001, Resing, et al. J. Am Soc Mass Spectrom 10:685-702 1999, Mandell, et al. Anal. Chem. 70:39487-3995 1998, Mandell, et al. Proc Natl Acad Sci USA 95:14705-10. 1998, Mandell, et al. J. Mol. Biol. 306:575-589 2001, Kim, et al. J Am Chem Soc 123:9860-6. 2001, Kim, et al. Biochemistry 40:14413-21. 2001, Zhang, et al. Protein Sci 10:2336-45. 2001, Kim, et al. Protein Sci 11:1320-9. 2002, Peterson, et al. Biochem J 362:173-81. 2002, Yan, et al. Protein Sci 11:2113-24. 2002). Building upon the pioneering work Walter Englander and David Smith (Englander, et al. Protein Science 6:1101-9 1997, Engen, et al. Analytical Chemistry 73:256A-265A 2001, Smith, et al. J. Mass Spectrometry 32:135-146 1997), a number of improvements to their methodologies and experimental equipment that have significantly improved throughput, comprehensiveness, and resolution have been developed and implemented, collectively referred to as enhanced Deuterium Exchange-Mass Spectrometry (DXMS).

DXMS can be used to obtain sufficient information on the exchange behavior of a two repeat construct (R1617) of chicken brain α-spectrin ($16^{th}$-$17^{th}$ repeats) to allow construction of a peptide amide hydrogen exchange rate map at near single-amide resolution, from which the thermodynamic stability or "energetic landscape" of the molecule could be assessed at the individual residue level. Results demonstrate that the long α-helices within the tandem repeats are not uniformly stable structures, have marked gradients in stability. If the "loop-migration" model is operative in α-spectrin, then these gradients provide the mechanism by which mechanical energy is stored in the stretched α-spectrin molecule.

Increased Production of Overlapping Peptides of α-Spectrin Construct R1617

The ability to localize and quantify detailed hydrogen exchange behavior with DXMS is largely determined by the degree to which a densely overlapping set of peptides can be proteolytically generated from the deuterated protein prior to LCMS. Prior to deuterium on-exchange analysis, digestion of exchange-quenched, undeuterated R1617 was performed on samples made to 0, 0.5, 1.0, 2.0, and 4 M GuHCl, with the duration of proteolysis with solid-state pepsin being systematically varied, to determine optimum conditions for maximally overlapping fragmentation. At 0.5 M GuHCl and 250 ul/min flow rate over the pepsin column (66 ul bed volume), 114 high quality fragments were produced. A second, higher resolution fragmentation map was also obtained by employing these conditions, but with the addition of a *Aspergillis satoi* Fungal Protease XIII (FP XIII) column (66 ul bed volume) after the pepsin column, resulting in the generation of an additional 86 peptides. A comparison of the fragments generated by pepsin and pepsin plus FPXIII is shown in FIG. 9. A total of 200 fragments were obtained with the combination of the pepsin and fungal protease columns. Such extensive fragmentation and redundancy in the overlapping of peptides was essential to successful calculations of reliable exchange rates for each residue in the spectrin construct.

Once the optimal quench-compatible fragmentation conditions were established, the R1617 construct was incubated in 150 mM NaCl, 5 mM tris, pD (read) 7.0 containing 75% mole-fraction deuterated water at 22 degrees C. for times varying from 3 seconds to $3.4 \times 10^5$ seconds, and then aliquots exchange-quenched by making them to 0.5% formic acid, 0.5M GuHCl at 0 degrees C., followed by immediate cooling to and storage at −80 degrees C. Quenched, deuterated samples were then enzymatically fragmented, and subjected to LCMS under continued quench conditions as described herein. The deuterium content of each of the 200 peptides that had been generated from each sample was then calculated from the LCMS data, for all on-exchange times, employing specialized data reduction software and corrections for back-exchange (loss of deuterium from peptides after institution of "quench") as previously described.

Construction of a Low-resolution Exchange Rate Map for Spectrin R1617

Figure 10:
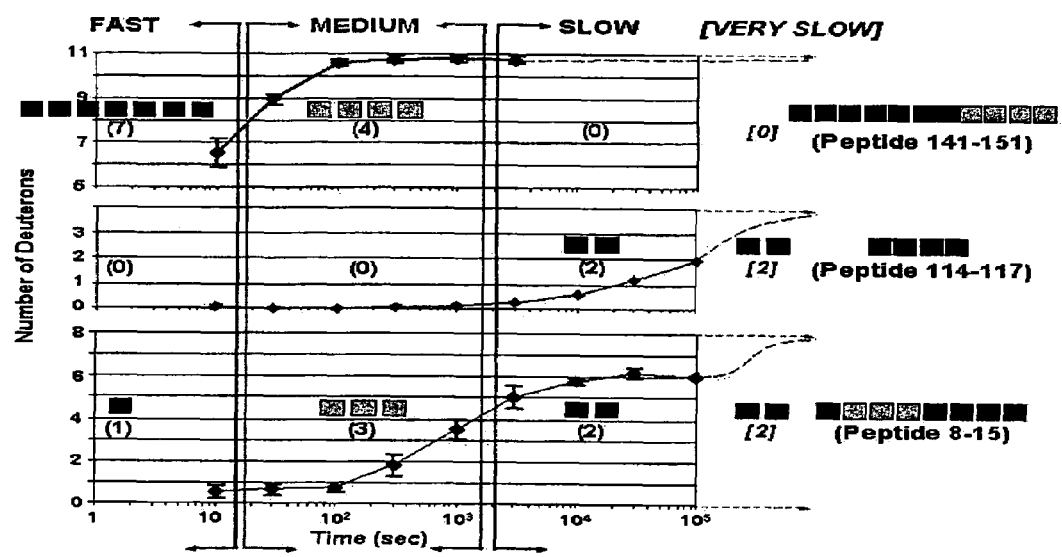
FIG. 10 shows the assignment of exchanging amides in spectrin R1617 into slow, medium, and fast-exchanging classes.

Plots of deuterium accumulation for each peptide vs on-exchange time were constructed from data obtained by analysis of 114 pepsin-only generated peptides, as shown in FIG. 10 for three representative peptides. The time axis was arbitrarily divided into three regions, (fast, medium, and slow-exchanging; FIG. 10) and the number of amides on each peptide that on-exchanged deuterium in the fast, medium and slow rate classes scored. The latter class was grouped with the very slow class unmeasured in the limited on-exchange times ($<10^5$ sec) used in this experiment; FIG. 10, italics). A map of rate-class vs construct sequence (FIG. 11B) was then constructed from this information, employing a strategy in which the (generally smaller) peptides containing one rate class were first placed in amino acid sequence register, followed by placement of peptides with two, and then three, rate classes, in a manner that required that placements of the three rate classes of amides in each peptide conform with the preceding placements. The resulting "α-Spectrin Consensus Rate Map" is indicated by the arrow in FIG. 11B.

This map demonstrated features that might reasonably be anticipated from the protein's structure: the short loops between the long α-helices were uniformly fast-exchanging (FIG. 11B, short horizontal bars below the consensus map) while substantial regions within the α-helices were much more slowly exchanging (the locations of the long α-helices are shown as light-blue bars below FIG. 11C). The map further indicated that substantial gradients in exchange rates were present within each α-helix, with slow-exchanging regions of helix gradually transitioning to fast exchanging-regions. Remarkably, these gradients in rates were not restricted to the ends of the helices, but occurred across most of their length. For example, helix B" was fast-exchanging for its N-terminal third, medium exchanging for its middle third, and slowly exchanging for its C-terminal third.

Construction of a High-resolution Exchange Rate Map for Spectrin R1617

To study these gradients in spectrin α-helix exchange rates at higher resolution, a computational method was developed for the deconvolution of aggregate, time-dependent peptide deuteration data, to specific exchange rates for each amide hydrogen within the native protein. This method, termed "High Resolution, residue-specific determination of amide hydrogen exchange rates from DXMS data" (HR-DXMS), employs an algorithm centered on use of a two-phase numerical technique, linear programming (LP) for an initial rate estimation followed by a nonlinear least squares fit (NLS). Essential to success of the method is the derivation and incorporation of residue-specific corrections for deuterium loss during "back-exchange" in contrast to the use of "peptide-average" loss corrections usually employed in hydrogen exchange data analysis. The method can also make use of additional hydrogen exchange data, obtained by systematically varying the duration of the usually deleterious "back-exchange", to allow resolution of individual amide rates within protein regions not sufficiently resolved by enzymatic fragmentation alone. A detailed description of the method, the validation studies that have been performed, and examples of the use of its implementing software are presented in Supplemental Material below.

FIG. 11C shows the results of application of HR-DXMS to the data from 200 deuterated spectrin 1617 construct fragments, obtained by the combined action of pepsin plus FP XIII. Results are expressed as the $DG_{exchange}$ (the difference in Gibbs free energy of exchange) between the folded and unfolded form of the protein, according to equation (7)

$$DG_{exchange,i} = -RT \ln(k_{ex,i}/k_{int,i}) \quad (7)$$

where $k_{ex,i}$ and $k_{int,i}$ are the experimental and intrinsic (random coil) exchange rates at amide i as determined from the intrinsic rates of random coil model peptides (Molday, et al. Biochemistry 11:150-8. 1972, Bai, et al. Proteins 17:75-86. 1993).

To facilitate comparison with the low resolution consensus rate map in FIGS. 11B and 11C is divided by two horizontal dashed lines that are placed at $DG_{exchange}$ values corresponding to the arbitrary rate divisions imposed in the generation of the approximate rate map (FIG. 10). There is considerable agreement between the results of the two methods and the computational approach resulted in a more finely detailed and less subjective description of the exchange rate distribution within the α-helices, clearly demonstrating the extensive exchange rate gradients that traverse the helices. The A' and A" helices have gradients with a stable central region that decreases in stability towards each end, while the B' and B" helices demonstrate more monotonic gradients with stable C-termini that gradually become less stable at the N-terminus. The tandem-repeat linker region, which, is seen to be an α-helix in the crystal structure, has a distinctly lower stability than the amides of the helices that immediately adjoin it, helix C' and A".

Calculation of the Hydrogen Exchange Rate Map of α-spectrin R1617 from its Crystallographically Determined Structure The experimentally determined exchange rate map for α-spectrin 1617 with purely computational estimates of hydrogen exchange rates that can be obtained with use of the COREX algorithm. COREX (implemented in the Fyrestar software of Redstorm Scientific, Houston Tex.), is a computational tool that utilizes the high-resolution structure of a protein as a template to generate a large ensemble of incrementally different conformational states. COREX represents proteins as ensembles of conformations rather than as discrete structures, and has been shown to predict amide hydrogen exchange rates with remarkable accuracy and precision when tested against available NMR-derived experimental data, suggesting that the calculated ensemble captures the general features of the actual ensemble, and thus provides a realistic physical description of proteins (Hilser, et al. Proteins 27:171-83 1997, Hilser, et al. J Mol Biol 262:756-72 1996, Hilser, et al. Proc Natl Acad Sci USA 95:9903-8 1998, Hilser Methods Mol Biol 168:93-116 2001). COREX was run in a sparse Monte Carlo mode against the structural coordinates of the α-spectrin R1617 construct and hydrogen exchange rate protection factors were calculated as described herein. FIG. 12B overlays the COREX-calculated and experimentally-determined protection factor maps deduced for α-spectrin R1617 by DXMS analysis. There is significant agreement in the overall pattern of stability between the experimental and computationally derived protection factor profiles, both confirming the α-spectrin α-helix stability gradients and cross-validating the ability of HR-DXMS to derive protection factor maps that substantially match those that can be obtained computationally by COREX analysis of known three dimensional structures.

The Substantial Gradients in Helix Stability are Uniquely Present in α-spectrin R1617

While it was anticipated that a few amides near the end of each helix (turn residues) might exchange faster than the bulk of the helix, the gradients in exchange rates, and corresponding gradients in helical stability, extended across most of the length of each the six α-helices in the two-repeat α-spectrin construct. To evaluate the significance of these stability gradients, the hydrogen exchange rates of α-helices within five other proteins was surveyed for which experimental measurements were available: horse cytochrome c, BPTI, SNASE, HEWL, and equine lysozyme (Milne, et al. Protein Sci 7:739-45. 1998, Radford, et al. Proteins 14:237-48 1992, Loh, et al. Biochemistry 32:11022-8 1993, Kim, et al. Biochemistry 32:9609-13 1993). Typically, the exchange rates of the first 4 amides of the N-termini of helices in these proteins could not be determined by NMR, indicating that exchange occurred too rapidly to be experimentally determined at the shortest time point experimentally accessible (generally 2 minutes). This is expected since the first 4 amino acids at the N-terminus of a typical α-helix (known as the N-cap residues) do not usually have robust cis-hydrogen bond acceptors. Amino acids interior to the N-cap residues in these proteins had typical free energies of hydration between 6-8 kcal/mole, values that were found only in the linker and most stable central portions of the helices in α-spectrin R1617. The N-terminus of the B" helix in R17 showed values well below 6 kcal/mole fully 15 residues into the helix.

These values indicate that substantial portions of the α-spectrin R1617 helices are much less stable under solution conditions than the comparable regions of the α-helices in the five comparison proteins. Although the conformational helix-loop transitions in the crystal structure are located in the BC loop of R17 it cannot be excluded that there may be structural differences in crystalline versus solution phases of R1617. Nevertheless, the asymmetric pattern of stability at the ends of the helices provides further support for potential conformational rearrangements in these regions.

Discussion

In this study, high-resolution protein stability profiles were derived for the prototypic α-spectrin two tandem-repeat R1617 by a novel experimental approach (HR-DXMS) and by use of the well-validated COREX algorithm operating on the 3-D structure of α-spectrin R1617. The two independently-derived profiles were highly concordant and demonstrated marked, unanticipated gradients in the stability of the several long α-helices in the construct. The discovery of these gradients has important implications for proposed mechanisms of α-spectrin elastic behavior.

Spectrin Elongation is Mediated by Tension-induced Catastrophic Unfolding

Atomic force microscopy measurements of α-spectrin constructs reveal that repeats abruptly unfold at forces of 20-50 pN (Law, et al. Biophys J 84:533-44. 2003). When several repeats are in tandem, the tension-length relationship exhibits a distinctive "sawtoothed" behavior in which tension gradually rises with increasing length until an abrupt drop in tension occurs, returning almost to baseline, followed immediately by repeated tension rise and collapse with continued elongation. The result is that the α-spectrin molecule can be elongated up to multiples of its resting length, with tension constrained to a constant, relatively narrow, range. The abrupt drops in tension have been attributed to catastrophic unfolding of individual repeats, and there is considerable evidence to support this model.

However, the mechanism responsible for the short-range rise in tension with each "sawtooth" is less clear. The force required to "snap open" the repeats is well above that typically found to be exerted on the α-spectrin molecule in simulations of membrane deformation, which are more in the range of 5-10 pN. Taken together, these observations indicate that the mechanisms that account for the rise in tension with each "sawtooth" are central to understanding α-spectrin's elasticity. Studies have indicated that repeats may undergo more subtle conformational changes that mediate elasticity in this 5-10 pN regime before catastrophic unfolding of the same or tandem repeats occurs with higher tension (Rief, et al. J Mol Biol 286:553-61. 1999, Altmann, et al. Structure (Camb) 10:1085-96. 2002).

α-Spectrin Elastic Behavior Requires Efficient Storage of Mechanical Energy

Models for α-spectrin elastic behavior should explain how mechanical energy is stored by tension-induced conformational change so as to allow efficient, low hysteresis recoil when tension is released. Models have been proposed in which tension induces gradual unwinding or melting of the ends of α-helical regions into elongated, relatively disordered loops (Altmann, et al. Structure (Camb) 10:1085-96. 2002, Paci, et al. Proc Natl Acad Sci USA 97:6521-6. 2000). In both catastrophic unfolding, and helix-melting models it is unclear how mechanical energy could be stored without undue hysteresis: the forces that mediate the non-covalent binding interactions within the structures of proteins operate over short distances and once the distances are exceeded, the forces in large part disappear. Once tension is released, entropic forces may allow reassembly of the unwrapped helical regions, but with resulting large losses in the mechanical energy that unwrapped them.

α-Spectrin Elasticity may be Mediated by Energy-storing Loop Migration

Crystal structures have been determined for two-repeat constructs consisting of the same sequence as α-spectrin R1617, but with small variations in the particular N- and C-terminal residues chosen to begin and end the construct: ie having differing "phases". These phase-differing constructs demonstrated discrete differences in their structures when crystallized (Grum, et al. Cell 98:523-35. 1999). These differences indicated that α-spectrin preferred to reduce its end-to-end distance (in the course of crystal-packing) by reorientation of the repeats by helix-loop-helix transitions that shifted the sequence-position of the short loops connecting helices without overall change in the amount of sequence in loop or helix: tension-induced loop migration (Grum, et al. Cell 98:523-35. 1999). This model is further supported by studies of the crystallized $16^{th}$ repeat of Drosophila α-spectrin which showed a conformational rearrangement of a loop region into a helix (Yan, et al. Science 262:2027-30 1993).

This model is particularly appealing, as it proposes that the tension-induced conformational changes do not substantially alter total amount of short-range binding interactions within the repeats: the fraction of sequence in loops vs helix remains constant, providing the opportunity for low-hysteresis conformational change. Results suggest that if this "loop-migration" model is operative in α-spectrin, then the loops will migrate into progressively more stable regions of the α-helices as α-spectrin is stretched, with reformation of less stable helix behind them, storing mechanical energy. This energy can be recovered when the molecule relaxes, and the loop migrates back into less stable regions of the helices, allowing reformation of the stable helical regions.

α-Spectrin Elasticity may be Mediated Through Linker-region Flexibility.

The linker between the $16^{th}$ and $17^{th}$ repeating units of R1617, and the linker-abutting sequence in each unit (helix C' and A") are present in the crystal structure as a single, very long uninterrupted α-helix. The phase-difference crystallization studies noted above also demonstrated that crystal packing could induce a slight bending of the linker region. This observation suggested that in solution, the linker region might be significantly more flexible than other α-helical regions of the molecule. The data support this inference, as it was found that a significant decrease in the $\Delta G_{exchange}$ (higher exchange rate) of 2-4 kcal/mol in the linker region when compared to the more stable helical regions flanking the linker, supporting the idea that the linker may be intrinsically less stable in solution, despite appearing as an α-helix in the crystal structure. It is unclear though whether this decrease in $\Delta G_{exchange}$ is due to enthalpic or entropic contributions at the linker region. Presumably the flanking helices, C' and A", are enthalpically more stable due to the hydrophobic packing of the triple helical bundle and are less vulnerable to the dynamic processes governing helical-coil transitions in single helices. The lower $\Delta G_{exchange}$ in the linker region is not due to the varying degree of amide solvent exposure if the linker exists in solution as an α-helix, amide hydrogens are efficiently hydrogen bonded with the carbonyls in the preceding turn. Only if the amide hydrogen bond is broken and the hydrogen is exposed to the solvent can exchange occur.

These exchanges in the linker region occur may occur via local or global unfolding. If the $\Delta G_{exchange}$ of the linker region were similar to the $\Delta G_{exchange}$ of the amides in the flanking helices, then global unfolding would be the likely mechanism. However, the decrease of 2-4 kcal/mol in the linker region indicates that predominately local unfolding is occurring there. Thus the helical linkers are unusually dynamic in solution, and likely exhibit a significantly increased flexibility relative to other parts of the molecule. Although the presence of an α-helix joining adjacent repeats may appear to be a "stiff" linkage, these results support the inference drawn from comparative analysis of differently "phase" structures, that under solution conditions, these linkers are dynamic structures that can provide significant configurational entropy for α-spectrin chains.

High Resolution DXMS

In the course of this study, novel methods ("HR-DXMS") were developed by which high quality amide hydrogen/deuterium mass spectrometry data can be computationally resolved into near single-amide resolution hydrogen exchange rate profiles for an entire protein construct. The method was validated by demonstrations of its ability to accurately deconvolute realistically-simulated raw DXMS fragmentation data, employing fragmentation densities, ranges of on-exchange times and data precision routinely obtained with DXMS analysis. It was further validated by demonstration of its ability to derive an exchange rate profile for α-spectrin R1617 that substantially matched that produced by analysis of the crystal structure of α-spectrin R1617 with the COREX algorithm. With this capability, HR-DXMS now rivals the resolution of NMR-based methods for amide hydrogen exchange rate measurement, with the substantial advantages of being able to measure even the fastest exchanging amides, and to do this with substantially larger proteins, and less material than is required for NMR approaches. The principal requirement for application of this method is that high quality, high fragment-density exchange data be obtained for the study protein. This is now readily available through application of the enhanced data acquisition methods ("DXMS") recently reported (Hamuro, et al. J. Mol. Biol. 323:871-881 2002, Hamuro, et al. J. Mol. Biol. 4:703-714 2002, Woods-Jr., et al. Journal of Cellular Biochemistry 37:89-98 2001, Hamuro, et al. J. Mol. Biol. 327:1065-1076 2003, Woods-Jr. U.S. Pat. No. 6,599,707. 2003, Zawadzki, et al. Protein Sci 12:1980-90 2003, Englander, et al. Proc. Nat. Acad. Sci. 100:7057-7062 2003).

There is a further, unique advantage of the HR-DXMS approach: The functional deuteration step of the analysis can be performed under conditions where the dynamic properties of the study protein can be directly manipulated, with experimental design limited only by the ingenuity of the investigator. For example, with the present α-spectrin study as a foundation, one can test the "loop migration" hypothesis, and other models for α-spectrin elasticity by performing comparative HR-DXMS studies with the deuteration step performed while the α-spectrin molecule is being progressively elongated, for example by shear stress fields generated by fluid flow or stirring. After induction of quench, exactly the same method of analysis that was employed in the present study would allow rigorous assessment of the several proposed mechanisms for α-spectrin elasticity.

The COREX algorithm was developed with the goal of representing the ensemble thermodynamic behavior of proteins in a computationally accessible manner. It scales well when implemented in a (massively) parallel manner, as opposed to typical molecular dynamics calculations. The amide hydrogen exchange-rate calculating ability of COREX was originally developed to allow validation of the stability profiles it generated by comparison with NMR-derived exchange rate measurements. The rate-calculating ability of COREX will play an important role in the manner in which HR-DXMS-derived protein stability profiles and exchange rate maps are interpreted and exploited. The close agreement between HR-DXMS and COREX-derived exchange rate profiles for α-spectrin R1617 has heightened this expectation. There are, however, minor portions of the COREX-derived profile that deviate from the experimental profile: the linker region and a portion of the C-terminal region of the molecule are shown to be more stable by COREX analysis than by HR-DXMS analysis. These differences may result from an inadequate sampling of states in the Monte Carlo mode employed.

Methods

Establishment of protein fragmentation maps. Thirty microliters of stock "exchange quench" solutions (0.8% formic acid, 0M/0.8M/1.6M/3.2M/6.4M GuHCl) was added to 20 ul of sample (final concentration 0.5% formic acid, 0M/0.05/1.0/2M/4M M GuHCl) containing 10-15 ug of protein in TBS, transferred to autosampler vials, and then frozen on dry ice within one minute after addition of quench solution. Vials with frozen samples were stored at −80 deg C. until transferred to the dry ice-containing sample basin of the cryogenic autosampler module of the DXMS apparatus. Samples were individually melted at 0 deg C., then injected (45 ul) and pumped through protease columns (0.05% TFA, 250 ul/min, 16 seconds exposure to protease). Proteolysis used immobilized pepsin (66 µl column bed volume, coupled to 20AL support from PerSeptive Biosystems at 30 mg/ml) or similarly immobilized *Aspergillus satoi* Fungal Protease XIII (20 mg/ml, 66 ul bed volume column). Protease-generated fragments were collected onto a C18 HPLC column, eluted by a linear acetonitrile gradient (5 to 45% B in 30 minutes; 50 µl/min; solvent A, 0.05% TFA; solvent B, 80% acetonitrile, 20% water, 0.01% TFA), and effluent directed to the mass spectrometer with data acquisition in either MS1 profile mode or data-dependent MS2 mode. Mass spectrometric analyses used a Thermo Finnigan LCQ electrospray ion trap type mass spectrometer operated with capillary temperature at 200° C. or an electrospray Micromass Q-Tof mass spectrometer, as previously described (Hamuro, et al. J. Mol. Biol. 323:871-881 2002, Hamuro, et al. J. Mol. Biol. 4:703-714 2002, Woods-Jr., et al. Journal of Cellular Biochemistry 37:89-98 2001, Hamuro, et al. J. Mol. Biol. 327:1065-1076 2003, Woods-Jr. U.S. Pat. No. 6,599,707. 2003, Zawadzki, et al. Protein Sci 12:1980-90 2003, Englander, et al. Proc. Nat. Acad. Sci. 100:7057-7062 2003). The Sequest software program (Thermo Finnigan Inc) was used to identify the likely sequence of the parent peptide ions. Tentative identifications were tested with specialized DXMS data reduction software developed in collaboration with Sierra Analytics, LLC, Modesto, Calif. This software searches MS1 data for scans containing each of the peptides, selects scans with optimal signal-to-noise, averages the selected scans, calculates centroids of isotopic envelopes, screens for peptide misidentification by comparing calculated and known centroids, then facilitates visual review of each averaged isotopic envelope allowing an assessment of "quality" (yield, signal/noise, resolution), and confirmation or correction of peptide identity and calculated centroid (Hamuro, et al. J. Mol. Biol. 323:871-881 2002, Hamuro, et al. J. Mol. Biol. 4:703-714 2002, Woods-Jr., et al. Journal of Cellular Biochemistry 37:89-98 2001, Hamuro, et al. J. Mol. Biol. 327:1065-1076 2003, Woods-Jr. U.S. Pat. No. 6,599,707. 2003, Zawadzki, et al. Protein Sci 12:1980-90 2003, Englander, et al. Proc. Nat. Acad. Sci. 100:7057-7062 2003).

On-exchange deuteration of proteins. After establishment of fragmentation maps amide hydrogen exchange-deuterated samples of R1617 were prepared and processed exactly as above, except that 5 ul of each protein stock solution was diluted with 15 ul of Deuterium Oxide (D2O), containing 5 mM Tris, 150 mM NaCl, pD (read) 7.0, and incubated at 22 degrees C. for $3, 10, 30, 100, 300, 10^3, 3\times10^3, 10^4, 2.5\times10^5, 3.4\times10^5$ seconds, at which time samples were supplemented with 30 ul of a quench solution (0.8% formic acid, 0.8M GuHCl) at 0 degrees C., and samples immediately frozen at −80 degrees C. until further processed as above. Data on the deuterated sample sets was acquired in a single automated 8-hour run, and subsequent data reduction performed on the DXMS data reduction software as previously described. Corrections for loss of deuterium-label by individual fragments during DXMS analysis (after "quench") were made through measurement of loss of deuterium from reference α-spectrin R1617 samples that had been equilibrium-exchange-deuterated under denaturing conditions, as previously described (Hamuro, et al. J. Mol. Biol. 323:871-881 2002, Hamuro, et al. J. Mol. Biol. 4:703-714 2002, Woods-Jr., et al. Journal of Cellular Biochemistry 37:89-98 2001, Hamuro, et al. J. Mol. Biol. 327:1065-1076 2003, Woods-Jr. U.S. Pat. No. 6,599,707. 2003, Zawadzki, et al. Protein Sci 12:1980-90 2003, Englander, et al. Proc. Nat. Acad. Sci. 100:7057-7062 2003). High Resolution, residue-specific determination of amide hydrogen exchange rates from DXMS data (HR-DXMS) was performed as described in Supplemental Material.

Equipment configuration. The equipment configuration consisted of electrically-actuated high pressure switching valves (Rheodyne), connected to two position actuators from Tar Designs Inc., Pittsburgh, as described previously (Hamuro, et al. J. Mol. Biol. 323:871-881 2002, Hamuro, et al. J. Mol. Biol. 4:703-714 2002, Woods-Jr., et al. Journal of Cellular Biochemistry 37:89-98 2001, Hamuro, et al. J. Mol. Biol. 327:1065 1076 2003, Woods-Jr. U.S. Pat. No. 6,599, 707. 2003, Zawadzki, et al. Protein Sci 12:1980-90 2003, Englander, et al. Proc. Nat. Acad. Sci. 100:7057-7062 2003). A highly agent-modified Spectraphysics AS3000 autosampler, partially under external PC control, employed a robotic arm to lift the desired frozen sample from the sample well, then automatically and rapidly melted and injected the sample under precise temperature control (Hamuro, et al. J. Mol. Biol. 323:871-881 2002, Hamuro, et al. J. Mol. Biol. 4:703-714 2002, Woods-Jr., et al. Journal of Cellular Biochemistry 37:89-98 2001. Hamuro, et al. J. Mol. Biol. 327:1065-1076 2003, Zawadzki, et al. Protein Sci 12:1980-90 2003, Englander, et al. Proc. Nat. Acad. Sci. 100:7057-7062 2003). The autosampler basin was further thermally insulated and all but 20 vial positions were filled with powdered dry ice sufficient to keep samples colder than −45° C. for 18 hours. Four HPLC pumps (Shimadzu LC-10AD) were operated by a Shimadzu SCL-10A pump controller. One produced forward flow over the pepsin column, another backflushed the protease column after sample digestion (0.05% aqueous TFA), and two delivered solvents to a downstream HPLC column for gradient elution (A: 0.05% aqueous TFA.; B; 80% acetonitrile, 20% water, 0.01% TFA; 1×50 mm C18 Vydac # 218MS5105, pH 2.3). Valves, tubing, columns and autosampler were contained within a refrigerator at 2.8° C., with pepsin and HPLC columns immersed in melting ice. The timing and sequence of operation of the DXMS apparatus fluidics were controlled by a personal computer running an in-house written LabView-based program, interfaced to solid-state relays (digital input/output boards, National Instruments), controlling pumps, valve actuators, and MS data acquisition (Hamuro, et al. J. Mol. Biol. 323:871-881 2002, Hamuro, et al. J. Mol. Biol. 4:703-714 2002, Woods-Jr., et al. Journal of Cellular Biochemistry 37:89-98 2001, Hamuro, et al. J. Mol. Biol. 327:1065-1076 2003, Woods-Jr. U.S. Pat. No. 6,599,707. 2003, Zawadzki, et al. Protein Sci 12:1980-90 2003, Englander, et al. Proc. Nat. Acad. Sci. 106:7057-7062 2003).

COREX Calculations of α-spectrin R1617 amide exchange rate protection factors. Fyrestar, operating the COREX algorithm, was installed on the Blue Horizon supercomputer at the San Diego Supercomputer Center, and run in a sparse Monte Carlo mode against the structural coordinates of the α-spectrin R1617 construct employing a COREX window size of 8 and a sampling of 1000 states per partition. This resulted in a sampling of 8000 states of the total 900 million possible. Hydrogen exchange rates and protection factors were calculated from the stability profile as previously described (Hilser, et al. Proteins 27:171-83 1997, Hilser, et al. J Mol Biol 262:756-72 1996, Hilser, et al. Proc Natl Acad Sci USA 95:9903-8 1998, Hilser Methods Mol Biol 168:93-116 2001).

Supplemental Material

Algorithm and Software for High Resolution, Residue-specific Determination of Amide Hydrogen Exchange Rates from DXMS Data: HR-DXMS There does not currently exist an algorithm that will reliably find a globally minimum value for an arbitrary non-linear function. A common numerical difficulty in non-linear optimization is the discovery of local optima which exhibit many of the properties of globally minimal points, but are not in fact globally minimal. All currently known algorithms for non-linear optimization are susceptible to the problem of incorrectly terminating at a local minimum; however, in the case of smooth and continuous objective functions, one can often ameliorate this problem by initializing the numerical optimization with a solution that is likely to be near the global minimum.

The following algorithm centers on use of a two-phase numerical technique, linear programming (LP) followed by nonlinear least squares (NLS). The computational problem is to determine the mass gain ("shifts") for each smallest segment of the protein's sequence (here termed "atomic unit" or AU) that is resolved by differences between each DXMS-generated overlapping fragments' sequence, at each time point measured in the experiment. Linear regression of the AU shifts was applied to determine a rate for each AU. The rates from the linear regression analysis of the shifts are then fed into the nonlinear least-squares technique as initial rates.

Linear Programming Method: Linear programming (LP) is a technique that optimizes an objective function subject to certain predefined linear constraints. Given a protein sequence P where $P_i$ denotes the i-th character of P, a fragment $f_{i,j}$ is simply a substring of P: $P_i$, $P_{i+1}$ . . . $P_j$. Fragments are generated by the protein digestion phase of the DXMS experiment, and are generally fixed for a given data analysis problem. A position k in the protein is covered by any fragment $f_{ij}$ when $i \leq k \leq j$. An AU is the largest consecutive substring whose positions are covered by the same set of fragments, and can not overlap. The concatenation of all AU generated by the fragments in an experiment will cover each position of P only once if, and only if, P is the union of all the fragments. Therefore the set of AU is determined entirely by the set of fragments generated by protein digestion. With the α-spectrin R1617 fragmentation map of 114 peptides there are 65 AU spanning 100% of the protein sequence with sizes ranging from 1 to 13 amides in length. By calculating the AU from the fragmentation pattern and knowing the mass shift of each AU at each time point we can calculate the mass shift, $d_{au}(t)$, for each AU as well as the corresponding error in the estimation. Note that if the fragmentation pattern produced 212 AU that would represent single amide coverage over the entire 212 amino acid sequence of α-spectrin R1617.

Therefore, A is the set of AU determined by F (the set of fragments). For each fragment f, where f is a subset of F, there exists a set of of AU whose positions are covered by f. For each AU, A(i), we define a variable $s_{i,t}$ that represents the mass shift of AU i at time t. For each fragment f, we define a variable $E_{f,t}$ which represents the experimental error in the mass shift measurement for fragment f at time t. The computational problem is to determine the mass gain ("shifts"), $s_{i,t}$, for each AU, A(i), at each time point measured in the experiment. FIG. 13A illustrates the definition of the AU for the first 15 amino acid segment of R1617. Atomic units (A1, A2 . . . A8) are defined by the set of fragments (f1, f2 . . . f2) and each fragment shift is the additive contribution of the calculated shifts for each AU, FIG. 13B. After determining the mass shift for each AU at each time point we apply linear regression of the AU's shifts to determine a rate for each AU. The rates so calculated represent average rates of exchange of all amide hydrogens within the AU and provide us with good initial starting rates to seed into our non-linear least squares fit.

Non-Linear Least Squares Fit: The exchange process in a protein of N amino acids can be approximated as N independent chemical reactions that each obey first-order reaction kinetics. In particular, if amino acid i has rate constant $k_{ex,i}$, then the amount of deuterium $D_i(t)$, at time t at position i is simply $$D_i(t) = 1 - e^{-k_{ex,i}t} \qquad 1.$$

The rate constant $k_{ex,i}$ is a function of pD temperature, protein sequence, and protein conformation. For a fragment f composed of n amides the amount of deuterium incorporated is $$D_{F(f),t} = S^n_{i=m}(1 - e^{-k_{ex,i}t}) \qquad 2.$$

where $D_{F(f),t}$ is the total amount of deuterium on fragment f starting at amino acid residue m through amino acid residue n at time t, and $k_{ex,i}$ is the exchange rate constant of amide i, where $m \leq i \leq n$. For the nonlinear least-squares technique the computational problem is to find rate constants that minimize the squared difference between the theoretical deuteration where $D_{off,i}(T)$ is the fraction of deuterium left on a deuterated amide given an off-exchange time of T, and $k_{int}$ is the intrinsic exchange rate of the amide under quench conditions (pH 2.3, 273K) calculated from known rates of model peptides from Bai and Englander (Molday, et al. Biochemistry 11:150-8. 1972, Bai, et al. Proteins 17:75-86. 1993). T represents the time upon quench to the time the fragment is analyzed in the mass spectrometer and is the sum of the fragment's retention time and the system lag time (SLT), the time between induction of exchange quench and sample loading onto the C18 column (2-5 min). Although the retention times for each fragment are readily determined, the SLT can be better approximated to a value which results in the least amount of error in the overall fit, as described below.

Equation 2 for the total deuterium on a fragment can be readily agent-modified to incorporate amide specific back exchange rate for every amide on that fragment by substitution of equation 4.

$$D_{corr,F(f),t} = S^n_{i=m} D_{off,i}(T)(1 - e^{-k_{ex,1}t}) \qquad 5.$$

Now $D_{corr,F(f),t}$ is the corrected total amount of deuterium for fragment f at time t taking into account amide specific back-exchange rates which are dependent on the fragments retention time in the system under quench conditions. Substituting $D_{corr,F(f),t}$ into equation 3 allows us to refit the exchange rates with the corrections automatically taken into account $$S^p_{f=1}[S^z_{t=1} D_{obs,F(f),t} - D_{corr,F(f),t})^2] = GE \qquad 6.$$

Validation studies. The success of the method relies on the extent of overlapping fragmentation, the number of sampled on-exchange time points, and the number of post-quench off exchange time points sampled. Simulation studies were performed to determine the overall performance of this approach when using values for these parameters that were readily achievable in the present study.

α-Spectrin R1617 construct simulations. Studies were performed to determine how accurately the HR-DXMS method could deconvolute input DXMS data, with a fragmentation intensity and number of on-exchange time points similar to those employed with the α-spectrin R1617 construct in the present study. An arbitrary exchange rate map for a hypothetical "Hyp R1617 protein" was generated that was approximately based on the rates calculated for α-spectrin R1617 by COREX analysis (FIG. 11C). Given these hypothetical rates, predicted deuteration levels for each of the same peptide fragment sequences (200 fragments) collected in the actual DXMS experiment with α-spectrin were generated, with and without incorporation of a normally-distributed random variable to simulate experimental and instrumental error. The HR-DXMS algorithm was used to simulate deuterated fragmentation data, and compared the resulting deconvoluted amide-specific determinations (expressed as the free energy of exchange; (FIG. 14) to the free energy of exchange profile of the "Hyp R1617 protein" used to generate the data (FIG. 14). There was a very good agreement between the two profiles when using simulated fragmentation data without error, which was only minimally degraded when a 20% error in peptide deuteration levels was added to the simulated data set prior to deconvolution. In our experience, peptide deuteration levels are typically measured with a precision of 5-10% in DXMS, due in large part to the reproducibility resulting from the extensive automation employed. Regions where individual amides considerably diverged can be observed by the lack of overlap between the blue and lavender colored lines (FIG. 14).

Horse cytochrome c. HR-DXMS was used to examine simulated DXMS deuterated fragment datasets based on published NMR-determined experimental hydrogen exchange rate data from horse cytochrome c (Milne, et al. Protein Sci 7:739-45. 1998). Residues where the rates of exchange had been too fast to be measurable in the NMR experiments were assigned arbitrary values. Since horse cytochrome c is 104 amino acids in length the same fragmentation pattern as that obtained for α-spectrin R1617 for the first 104 amino acid residues was used. FIG. 15 shows that the experimentally-determined exchange amide-specific free energy profile of exchange of cytochrome c agree closely with the HR-DXMS-deconvoluted rate profile of the simulated data.

An important necessity to proper behavior of the fitting algorithm is the imposition of upper and lower bounds during the nonlinear least squares fit. Since the slowest exchanging peptides reached 50% deuteration level at $10^5$ sec this corresponds to an average exchange rate on the order of $10^{-6}$/sec. Lower boundaries were set 2 orders of magnitude lower so as to not exclude the possibility that a single amide may show slower rates within a given peptide, with the exception of regions of the protein sequence that had peptides that were maximally deuterated at the 10 sec time point. With these peptides, the lower boundary of exchange was calculated at 0.92/sec, corresponding to 99.99% deuteration at 10 secs. The upper boundaries for the fit were set to the maximum exchange rates of each amide (Molday, et al. Biochemistry 11:150-8. 1972, Bai, et al. Proteins 17:75-86. 1993).

While the invention has been described and exemplified in sufficient detail for those skilled in this art to make and use it, various alternatives, modifications, and improvements should be apparent without departing from the spirit and scope of the invention. The present invention is well adapted to carry out the objects and obtain the ends and advantages mentioned, as well as those inherent therein.

The examples provided here are representative of preferred embodiments, are exemplary, and are not intended as limitations on the scope of the invention. Modifications therein and other uses will occur to those skilled in the art. These modifications are encompassed within the spirit of the invention.

The disclosure of all publications cited above are expressly incorporated herein by reference, each in its entirety, to the same extent as if each were incorporated by reference individually.

That which is claimed is:

1. A method for improving the chance of success of crystallizing a protein of interest or improving the quality of a crystallized protein of interest wherein said crystallized protein is to be used for crystallographic structural determination, said method comprising:
   a) comparing a first hydrogen-deuterium exchange mass spectrometry (DXMS) analysis of said protein of interest to a second DXMS analysis of said protein in order to identify agents and/or conditions which reduce the content of unstructured regions of said protein, wherein:
      (i) said first DXMS analysis identifies unstructured regions of said protein, and
      (ii) said second DXMS analysis is carried out in the presence of an agent and/or condition which potentially reduces the content of unstructured regions; and
   b) subjecting said protein to crystallization and structure determination in the presence of the identified agents and/or conditions which reduce the content of the unstructured regions thereof, thereby improving the quality of the protein crystal or improving the chance of success of crystallizing said protein.

2. A method according to claim 1, wherein said DXMS analysis comprises determining the quantity of deuterium or the rate of hydrogen-deuterium exchange, or both the quantity of deuterium and the rate of hydrogen-deuterium exchange, of a plurality of peptide amide hydrogens exchanged for said deuterium in a protein labeled by hydrogen exchange with deuterated water.

3. A method according to claim 2, wherein said determining the quantity of deuterium or the rate of hydrogen-deuterium exchange or both the quantity of deuterium and the rate of hydrogen-deuterium exchange comprises:
   (a) fragmenting said labeled protein into a plurality of fragments under slowed hydrogen exchange conditions;
   (b) identifying which fragments of said plurality of fragments are labeled with deuterium;
   (c) progressively degrading each fragment of said plurality of fragments to obtain a series of subfragments, wherein each subfragment of said series is composed of about 1-5 fewer amino acid residues than the preceding subfragment in the series; and
   (d) correlating the amount of deuterium associated with each subfragment with an amino acid sequence of said fragment from which said subfragment was generated, thereby determining the quantity of deuterium or the rate of hydrogen-deuterium exchange or both the quantity of deuterium and the rate of hydrogen-deuterium exchange of a plurality of peptide amide hydrogens exchanged for said deuterium in a protein labeled with a hydrogen exchange with deuterated water.

4. A method according to claim 3, wherein said fragmenting in step (a) comprises contacting said labeled protein with at least one acid stable endopeptidase.

5. A method according to claim 4, wherein said at least one acid stable endopeptidase is coupled to a support material.

6. A method according to claim 4, wherein said at least one acid stable endopeptidase is selected from the group consisting of pepsin, cathepsin D, newlase, *Aspergillus* proteases, thermolysin, protease type XIII, and combinations of any two or more thereof.

7. The method according to claim 4, wherein said at least one acid stable endopeptidase is pepsin.

8. A method according to claim 3, wherein said progressively degrading comprises contacting said fragments with at least one acid stable exopeptidase.

9. A method according to claim 8, wherein said acid stable exopeptidase is coupled to a support material.

10. A method according to claim 3, wherein said progressively degrading comprises contacting said fragments with at least one acid resistant carboxypeptidase.

11. A method according to claim 10, wherein said at least one acid resistant carboxypeptidase is selected from the group consisting of carboxypeptidase P, carboxypeptidase Y, carboxypeptidase W, carboxypeptidase C and combinations of any two or more thereof.

12. A method according to claim 3, wherein said fragmenting in step (a) comprises contacting said labeled protein with at least one acid stable endopeptidase selected from the group consisting of pepsin, newlase, cathepsin C, *Aspergillus* proteases, protease type XIII, thermolysin, and combinations of any two or more thereof.

13. A method according to claim 2, wherein said determining the quantity of deuterium or the rate of hydrogen-deuterium exchange or both the quantity of deuterium and the rate of hydrogen-deuterium exchange comprises:
(a) generating a population of sequence-overlapping fragments of said labeled protein by treatment with at least one endopeptidase under conditions of slowed hydrogen exchange, and then
(b) deconvoluting fragmentation data acquired from said population of sequence-overlapping endopeptidase-generated fragments.

14. A method according to claim 13, wherein said population of sequence-overlapping endopeptidase-generated fragments is generated by cleaving said protein with an endopeptidase selected from the group consisting of a serine endopeptidase, a cysteine endopeptidase, an aspartic endopeptidase, a metalloendopeptidase, a threonine endopeptidase, and combinations of any two or more thereof.

15. A method according to claim 13, wherein said at least one endopeptidase is coupled to a support material.

16. A method according to claim 13, wherein said at least one endopeptidase is pepsin.

17. A method according to claim 13, wherein said population of sequence-overlapping endopeptidase-generated fragments is generated by two or more endopeptidases used in combination.

18. A method according to claim 13, wherein said at least one endopeptidase is newlase or *Aspergillus* protease XIII.

19. A method according to claim 13, wherein said at least one endopeptidase is an acid-tolerant *Aspergillus* protease.

20. A method according to claim 13, wherein said population of sequence-overlapping endopeptidase-generated fragments is generated at a pH of about 1.8-3.4.

21. A method according to claim 20, wherein said population of sequence-overlapping endopeptidase-generated fragments is generated at a pH of about 2-3.

22. A method according to claim 21, wherein said population of sequence-overlapping endopeptidase-generated fragments is generated at a pH of about 2.0-2.5.

23. A method according to claim 21, wherein said population of sequence-overlapping endopeptidase-generated fragments is generated at a pH of about 2.5-3.0.

24. A method according to claim 13, wherein said population of sequence-overlapping endopeptidase-generated fragments is generated in less than five minutes.

25. A method according to claim 24, wherein said population of sequence-overlapping endopeptidase-generated fragments is generated in about one minute or less.

26. A method according to claim 25, wherein said population of sequence-overlapping endopeptidase-generated fragments is generated in about 40 seconds or less.

27. A method according to claim 13, wherein deconvoluting comprises:
comparing the quantity of deuterium and/or rate of exchange of hydrogen at a peptide amide hydrogen with deuterium on a plurality of endopeptidase fragments in said population of sequence-overlapping endopeptidase-generated fragments with the quantity of deuterium and/or rate of exchange of hydrogen at a peptide amide hydrogen on at least one other endopeptidase fragment in said population of sequence-overlapping endopeptidase-generated fragments,
wherein said quantities are corrected for back-exchange losses subsequent to the initiation of slowed exchange conditions in an amino acid sequence-specific manner.

28. A method according to claim 27, wherein labeled peptide amides are localized in an amino acid sequence-specific manner by measuring rates of exchange as a function of time under slowed exchange conditions.

29. A method according to claim 13, wherein said population of sequence-overlapping endopeptidase-generated fragments contains a plurality of sequence-overlapping fragments, wherein more than half of the members of said population have sequences that overlap other members of said population.

30. A method according to claim 13, wherein a majority of members of said population of sequence-overlapping endopeptidase-generated fragments is present in an analytically sufficient quantity to permit its further characterization.

31. A method according to claim 13, wherein determining the quantity and rate of exchange of peptide amide hydrogen (s) is carried out contemporaneously with generating a population of sequence-overlapping endopeptidase-generated fragments.

32. A method according to claim 13, further comprising determining off-exchange rates of labeled peptide amides under conditions of slowed hydrogen exchange and random-coil conditions from a plurality of fragments and fragment differences.

33. A method according to claims 3 or 13, wherein the presence and quantity of said deuterium on said fragments of said labeled protein is determined by measuring the mass of said fragments.

34. A method according to claim 33, wherein said measuring is performed using mass spectrometry.

35. A method according to claim 3 or claim 13, further comprising the use of conditions that effect protein denaturation under slowed exchange conditions prior to generation of said fragments.

36. A method according to claim 35, wherein said conditions comprise contacting said labeled protein with guanidine hydrochloride at a concentration of about 0.05-4 M.

37. A method according to claim 35, wherein said conditions comprise contacting said labeled protein first with guanidine thiocyanate at a concentration of about 1.5-4 M, followed by dilution into guanidine hydrochloride at a concentration of about 0.05-4 M.

38. A method according to claim 3 or 13, further comprising disrupting disulfide bonds in the labeled protein prior to generating said fragments.

39. A method according to claim 38, wherein said disrupting comprises contacting the labeled protein with a phosphine.

40. A method according to claim 1, wherein said protein is a protein that is resistant to crystallization or that forms crystals that do not diffract X-rays sufficient for structure determination.

* * * * *